(12) United States Patent
Danter et al.

(10) Patent No.: US 9,624,220 B2
(45) Date of Patent: Apr. 18, 2017

(54) COMPOUNDS AND METHOD FOR TREATMENT OF HIV

(71) Applicant: Critical Outcome Technologies Inc., London (CA)

(72) Inventors: Wayne Danter, London (CA); Clinton Threlfall, London (CA); Sylvain Guizzetti, Illkirch (FR); Julien Marin, Illkirch (FR)

(73) Assignee: Critical Outcome Technologies Inc., London (CA)

( * ) Notice: Subject to any disclaimer, the term of this patent is extended or adjusted under 35 U.S.C. 154(b) by 0 days.

(21) Appl. No.: 15/209,231

(22) Filed: Jul. 13, 2016

(65) Prior Publication Data

US 2016/0333010 A1    Nov. 17, 2016

Related U.S. Application Data

(62) Division of application No. 14/618,986, filed on Feb. 10, 2015, now Pat. No. 9,422,282, which is a division of application No. 13/638,597, filed as application No. PCT/CA2011/000357 on Apr. 1, 2011, now Pat. No. 8,987,272.

(60) Provisional application No. 61/320,223, filed on Apr. 1, 2010.

(51) Int. Cl.
| *C07D 471/04* | (2006.01) |
| *C07D 239/36* | (2006.01) |
| *C07D 239/40* | (2006.01) |
| *C07D 239/42* | (2006.01) |
| *C07D 413/04* | (2006.01) |
| *C07D 239/47* | (2006.01) |
| *C07D 239/557* | (2006.01) |
| *C07D 239/56* | (2006.01) |
| *C07D 487/04* | (2006.01) |

(52) U.S. Cl.
CPC ......... *C07D 471/04* (2013.01); *C07D 239/36* (2013.01); *C07D 239/40* (2013.01); *C07D 239/42* (2013.01); *C07D 239/47* (2013.01); *C07D 239/557* (2013.01); *C07D 239/56* (2013.01); *C07D 413/04* (2013.01); *C07D 487/04* (2013.01)

(58) Field of Classification Search
CPC .................................................... C07D 471/04
See application file for complete search history.

(56) References Cited

U.S. PATENT DOCUMENTS

| 3,239,539 A | 3/1966 | Bartlett et al. |
| 3,250,791 A | 5/1966 | Webster et al. |
| 3,671,639 A | 6/1972 | Sasse et al. |
| 4,463,077 A | 7/1984 | Matsuura et al. |
| 4,537,844 A | 8/1985 | Hashimoto |
| 4,593,027 A | 6/1986 | Winklemann et al. |
| 4,619,878 A | 10/1986 | Hashimoto |
| 4,748,160 A | 5/1988 | Bennion et al. |
| 4,927,843 A | 5/1990 | Teitz |
| 4,977,051 A | 12/1990 | Ohno et al. |
| 4,978,670 A | 12/1990 | Rector et al. |
| 4,985,433 A | 1/1991 | Secrist, III et al. |
| 4,985,434 A | 1/1991 | Secrist, III et al. |
| 5,008,265 A | 4/1991 | Secrist, III et al. |
| 5,008,270 A | 4/1991 | Secrist, III et al. |
| 5,023,334 A | 6/1991 | Rector et al. |
| 5,135,928 A | 8/1992 | Reiter et al. |
| 5,155,110 A | 10/1992 | Connor et al. |
| 5,189,039 A | 2/1993 | Niwas et al. |

(Continued)

FOREIGN PATENT DOCUMENTS

| CA | 2060843 | 9/1922 |
| CA | 1250292 | 2/1989 |

(Continued)

OTHER PUBLICATIONS

Vippagunta et al. (2000).*
Wolff et al. (1976).*
International Search Report for PCT/CA2011/000357, dated Jun. 13, 2011, 10 pages.
EESR mailed in EP 11761876.9 on Jul. 15, 2014.
Agrawal et al., "Potential Antitumor Agents. 11 Inhibitors of Alkaline Phosphatase, an Enzyme Involved in the Resistance of Neoplastic Cell to 6-Thiopurines", 1974, Journal of Medicinal Chemistry, vol. 17, No. 9, pp. 934-938.

(Continued)

*Primary Examiner* — Paul V Ward
(74) *Attorney, Agent, or Firm* — Dilworth IP LLC

(57) ABSTRACT

The invention relates to a compound of Formulae I and/or II:

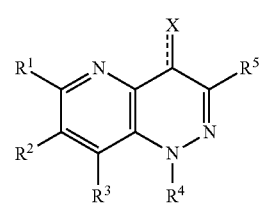

Formula I

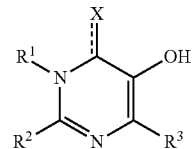

Formula II and/or a pharmaceutically-acceptable salt, hydrate, solvate, tautomer, optical isomer, E-isomer, Z-isomer, or combination thereof; X is selected from Se, N—OH, NH, $NO_2$, CN, N—CN, N=O, O or S, and the remaining substituents are described herein; and a composition thereof. The invention also relates to a method of administration thereof; and use thereof to treat HIV.

20 Claims, 2 Drawing Sheets

(56) References Cited

U.S. PATENT DOCUMENTS

| | | |
|---|---|---|
| 5,196,291 A | 3/1993 | Okada et al. |
| 5,292,756 A | 3/1994 | Duggan et al. |
| 5,328,914 A | 7/1994 | Hocquaux et al. |
| 5,334,748 A | 8/1994 | Buckley et al. |
| 5,344,836 A | 9/1994 | Hamanaka et al. |
| 5,358,946 A | 10/1994 | Wilde |
| 5,409,930 A | 4/1995 | Spada et al. |
| 5,441,847 A | 8/1995 | Fukawa et al. |
| 5,480,883 A | 1/1996 | Spada et al. |
| 5,521,184 A | 5/1996 | Zimmermann |
| 5,543,520 A | 8/1996 | Zimmermann |
| 5,604,210 A | 2/1997 | Nagaoka et al. |
| 5,612,340 A | 3/1997 | Zimmermann |
| 5,618,829 A | 4/1997 | Takayanagi et al. |
| 5,646,153 A | 7/1997 | Spada et al. |
| 5,656,643 A | 8/1997 | Spada et al. |
| 5,710,158 A | 1/1998 | Myers et al. |
| 5,714,493 A | 2/1998 | Myers et al. |
| 5,721,238 A | 2/1998 | Heiker et al. |
| 5,736,534 A | 4/1998 | Arnold |
| 5,750,088 A | 5/1998 | Sworin et al. |
| 5,760,041 A | 6/1998 | Wissner et al. |
| 5,763,470 A | 6/1998 | Tang et al. |
| 5,795,889 A | 8/1998 | Spada et al. |
| 5,798,451 A | 8/1998 | Von Deyn et al. |
| 5,872,272 A | 2/1999 | Yano et al. |
| RE36,256 E | 7/1999 | Spada et al. |
| 5,932,574 A | 8/1999 | Baker |
| 5,948,819 A | 9/1999 | Ohtsuka et al. |
| 5,958,935 A | 9/1999 | Davis et al. |
| 5,977,146 A | 11/1999 | Muller et al. |
| 5,985,894 A | 11/1999 | Clemence et al. |
| 6,057,320 A | 5/2000 | Spada et al. |
| 6,069,134 A | 5/2000 | Roth et al. |
| 6,103,728 A | 8/2000 | Tang et al. |
| 6,127,374 A | 10/2000 | Bridges |
| 6,153,617 A | 11/2000 | Bridges |
| 6,156,617 A | 12/2000 | Saitoh |
| 6,169,091 B1 | 1/2001 | Cockerill et al. |
| 6,174,889 B1 | 1/2001 | Cockerill et al. |
| 6,180,636 B1 | 1/2001 | Traxler et al. |
| 6,184,377 B1 | 2/2001 | Gao |
| 6,207,669 B1 | 3/2001 | Cockerill et al. |
| 6,235,746 B1 | 5/2001 | Davis et al. |
| 6,251,911 B1 | 6/2001 | Bold et al. |
| 6,268,391 B1 | 7/2001 | Dickerson et al. |
| 6,352,168 B1 | 3/2002 | Lin |
| RE37,650 E | 4/2002 | Myers et al. |
| 6,391,874 B1 | 5/2002 | Cockerill et al. |
| 6,420,560 B1 | 7/2002 | Numerof et al. |
| 6,432,963 B1 | 8/2002 | Hisamichi et al. |
| 6,525,072 B1 | 2/2003 | Tang et al. |
| 6,528,509 B1 | 3/2003 | Hale et al. |
| 6,538,002 B1 | 3/2003 | Finke et al. |
| 6,562,818 B1 | 5/2003 | Bridges |
| 6,600,037 B1 | 7/2003 | Davis et al. |
| 6,635,641 B2 | 10/2003 | Bender et al. |
| 6,723,726 B1 | 4/2004 | Cockerill et al. |
| 6,828,320 B2 | 12/2004 | Cockerill et al. |
| 6,949,639 B1 | 9/2005 | Hovinen et al. |
| 7,052,870 B2 | 5/2006 | Sabatini et al. |
| 7,138,416 B2 | 11/2006 | Sankaranarayanan |
| 7,175,844 B2 | 2/2007 | King |
| 7,202,367 B2 | 4/2007 | Cellier et al. |
| 8,034,815 B2 | 10/2011 | Danter et al. |
| 8,138,191 B2 | 3/2012 | Danter |
| 8,367,675 B2 | 2/2013 | Danter et al. |
| 8,420,643 B2 | 4/2013 | Danter et al. |
| 8,580,792 B2 | 11/2013 | Danter |
| 2001/0021717 A1 | 9/2001 | Potter et al. |
| 2001/0027205 A1 | 10/2001 | Camden |
| 2001/0041964 A1 | 11/2001 | Grass et al. |
| 2001/0044451 A1 | 11/2001 | Fraley et al. |
| 2001/0047007 A1 | 11/2001 | Fraley et al. |
| 2001/0047364 A1 | 11/2001 | Proctor |
| 2001/0049092 A1 | 12/2001 | Ekins et al. |
| 2001/0051628 A1 | 12/2001 | Huang et al. |
| 2002/0010550 A1 | 1/2002 | Grass et al. |
| 2002/0012641 A1 | 1/2002 | Voorhees et al. |
| 2002/0013334 A1 | 1/2002 | Robl et al. |
| 2002/0013662 A1 | 1/2002 | Grass et al. |
| 2002/0014408 A1 | 2/2002 | Schroeder |
| 2002/0018988 A1 | 2/2002 | Klinck et al. |
| 2002/0028779 A1 | 3/2002 | High et al. |
| 2002/0028826 A1 | 3/2002 | Robl et al. |
| 2002/0042423 A1 | 4/2002 | Richert et al. |
| 2002/0061901 A1 | 5/2002 | Robl et al. |
| 2002/0072526 A1 | 6/2002 | Fraley et al. |
| 2002/0086791 A1 | 7/2002 | Iglesia et al. |
| 2002/0115858 A1 | 8/2002 | Zimmermann et al. |
| 2002/0147214 A1 | 10/2002 | Cockerill et al. |
| 2002/0151540 A1 | 10/2002 | Lai et al. |
| 2003/0087881 A1 | 5/2003 | Bridges |
| 2003/0125343 A1 | 7/2003 | Gambacorti-Passerini et al. |
| 2003/0130286 A1 | 7/2003 | Denny et al. |
| 2003/0153755 A1 | 8/2003 | Moffat et al. |
| 2003/0176396 A1 | 9/2003 | Shea et al. |
| 2003/0181495 A1 | 9/2003 | Lai et al. |
| 2003/0212269 A1 | 11/2003 | Davis et al. |
| 2003/0236413 A1 | 12/2003 | Cellier et al. |
| 2004/0092747 A1 | 5/2004 | Bender et al. |
| 2004/0102453 A1 | 5/2004 | Buerger et al. |
| 2004/0171032 A1 | 9/2004 | Baker et al. |
| 2004/0204477 A1 | 10/2004 | Moll et al. |
| 2004/0224968 A1 | 11/2004 | Seidelmann et al. |
| 2004/0235786 A1 | 11/2004 | Orr |
| 2004/0235798 A1 | 11/2004 | Murthi et al. |
| 2005/0010017 A1 | 1/2005 | Blakely et al. |
| 2005/0014169 A1 | 1/2005 | Latham et al. |
| 2005/0131022 A1 | 6/2005 | Player et al. |
| 2005/0192884 A1 | 9/2005 | Raines |
| 2006/0019831 A1 | 1/2006 | Reinhard et al. |
| 2006/0052361 A1 | 3/2006 | Miyazaki et al. |
| 2006/0217426 A1 | 9/2006 | Eto et al. |
| 2007/0197495 A1 | 8/2007 | Chibale |
| 2007/0280928 A1 | 12/2007 | Buck et al. |
| 2008/0004274 A1 | 1/2008 | Diaz et al. |
| 2008/0171744 A1 | 7/2008 | Danter et al. |
| 2011/0152281 A1 | 6/2011 | Danter et al. |
| 2012/0077820 A1 | 3/2012 | Danter et al. |
| 2012/0195887 A1 | 8/2012 | Danter |

FOREIGN PATENT DOCUMENTS

| | | |
|---|---|---|
| CA | 2109975 | 5/1994 |
| CA | 2553242 | 8/2005 |
| CA | 2584179 | 4/2006 |
| CN | 1224005 | 7/1999 |
| CN | 1891701 | 1/2007 |
| CN | 1907970 | 2/2007 |
| DE | 3237649 | 4/1984 |
| DE | 4207400 | 9/1993 |
| DE | 04400451 | 7/1994 |
| EP | 106 284 | 10/1983 |
| EP | 142 740 | 10/1984 |
| EP | 225 726 | 11/1986 |
| EP | 00172031 | 5/1988 |
| EP | 361 645 | 6/1989 |
| EP | 0329108 | 8/1989 |
| EP | 0 420 005 | 9/1990 |
| EP | 0 452 848 | 4/1991 |
| EP | 0425282 | 5/1991 |
| EP | 512 420 | 4/1992 |
| EP | 554 856 | 2/1993 |
| EP | 580 374 | 7/1993 |
| EP | 00571857 | 12/1993 |
| EP | 0600 832 | 6/1994 |
| EP | 0631179 | 12/1994 |
| EP | 722 937 | 1/1996 |
| EP | 00727701 | 8/1996 |
| EP | 807 580 | 5/1997 |
| EP | 00902028 | 3/1999 |
| EP | 00807850 | 10/2000 |
| EP | 01103549 | 5/2001 |

(56) References Cited

FOREIGN PATENT DOCUMENTS

| | | |
|---|---|---|
| EP | 01325921 | 7/2003 |
| FR | 2013371 | 4/1970 |
| FR | 2879194 | 6/2006 |
| GB | 1026401 | 4/1966 |
| GB | 1231783 | 5/1971 |
| GB | 2304471 | 3/1997 |
| GB | 2357971 | 7/2001 |
| JP | 56-095161 | 8/1981 |
| JP | 59088468 | 5/1984 |
| JP | 60184254 | 9/1985 |
| JP | 3093767 | 4/1991 |
| JP | 05058894 | 3/1993 |
| JP | 1993241264 | 9/1993 |
| JP | 06-247990 | 9/1994 |
| JP | 1995114195 | 5/1995 |
| JP | 7219256 | 8/1995 |
| JP | 9328463 | 12/1997 |
| JP | 07-072571 | 3/1999 |
| JP | 11080131 | 3/1999 |
| JP | 11133545 | 5/1999 |
| JP | 2000143636 | 5/2000 |
| JP | 2001172217 | 6/2001 |
| JP | 2006-181940 | 7/2006 |
| JP | 2006181940 | 7/2006 |
| JP | 2008-088107 | 4/2008 |
| WO | WO 86/04582 | 8/1986 |
| WO | WO 91/06548 | 5/1991 |
| WO | WO 92/03421 | 3/1992 |
| WO | WO 92/06076 | 4/1992 |
| WO | WO 92/08464 | 5/1992 |
| WO | WO 93/02091 | 2/1993 |
| WO | WO 93/21187 | 10/1993 |
| WO | WO 94/18959 | 9/1994 |
| WO | WO 95/23796 | 2/1995 |
| WO | WO 95/17423 | 6/1995 |
| WO | WO 95/27693 | 10/1995 |
| WO | WO 96/05818 | 2/1996 |
| WO | WO 96/09294 | 3/1996 |
| WO | WO 96/14295 | 5/1996 |
| WO | WO 96/37472 | 11/1996 |
| WO | WO 97/00894 | 1/1997 |
| WO | WO 97/02238 | 1/1997 |
| WO | WO 97/03069 | 1/1997 |
| WO | WO 97/13760 | 4/1997 |
| WO | WO 98/08492 | 3/1998 |
| WO | WO 98/55448 | 12/1998 |
| WO | WO 99/09016 | 2/1999 |
| WO | WO 99/18102 | 4/1999 |
| WO | WO 99/62486 | 12/1999 |
| WO | WO 00/09126 | 2/2000 |
| WO | WO 00/18737 | 4/2000 |
| WO | WO 00/18740 | 4/2000 |
| WO | WO 00/50032 | 8/2000 |
| WO | WO 00/61186 | 10/2000 |
| WO | WO 00/74702 | 12/2000 |
| WO | WO 00/74742 | 12/2000 |
| WO | WO 01/12227 | 2/2001 |
| WO | WO 01/16271 | 3/2001 |
| WO | WO 01/34585 | 5/2001 |
| WO | WO 01/47899 | 7/2001 |
| WO | WO 01/53274 | 7/2001 |
| WO | WO 01/25220 | 9/2001 |
| WO | WO 01/64650 | 9/2001 |
| WO | WO 01/64825 | 9/2001 |
| WO | WO 01/64828 | 9/2001 |
| WO | WO 01/64994 | 9/2001 |
| WO | WO 01/66709 | 9/2001 |
| WO | WO 01/70741 | 9/2001 |
| WO | WO 02/22597 | 3/2002 |
| WO | WO 02/30931 | 4/2002 |
| WO | WO 02/49413 | 6/2002 |
| WO | WO 02/068574 | 9/2002 |
| WO | WO 02/068577 | 9/2002 |
| WO | WO 02/070541 | 9/2002 |
| WO | WO 02/083126 | 10/2002 |
| WO | WO 03/004489 | 1/2003 |
| WO | WO 03/051276 | 6/2003 |
| WO | WO 03/062204 | 7/2003 |
| WO | WO 03/070241 | 8/2003 |
| WO | WO 03/093297 | 11/2003 |
| WO | WO 2004/004725 | 1/2004 |
| WO | WO 2004/011456 | 2/2004 |
| WO | WO 2004/019933 | 3/2004 |
| WO | WO 2004/063147 | 7/2004 |
| WO | WO 2004/066725 | 8/2004 |
| WO | WO 2004/069801 | 8/2004 |
| WO | WO 2004/076640 | 9/2004 |
| WO | WO 2004/080492 | 9/2004 |
| WO | WO 2004/085382 | 10/2004 |
| WO | WO 2004/099371 | 11/2004 |
| WO | WO 2005/010017 | 2/2005 |
| WO | WO 2005/012252 | 2/2005 |
| WO | WO 2005/023183 | 3/2005 |
| WO | WO 2005/039489 | 5/2005 |
| WO | WO 2005/046604 | 5/2005 |
| WO | WO2005061490 | 7/2005 |
| WO | WO 2005/073189 | 8/2005 |
| WO | WO 2005/073216 | 8/2005 |
| WO | WO 2005/073217 | 8/2005 |
| WO | WO 2005/087211 | 9/2005 |
| WO | WO 2005/107463 | 11/2005 |
| WO | WO 2005/116039 | 12/2005 |
| WO | WO 2006/009754 | 1/2006 |
| WO | WO 2006/009765 | 1/2006 |
| WO | WO 2006/063863 | 6/2006 |
| WO | WO 2006/069080 | 6/2006 |
| WO | WO 2006/069807 | 7/2006 |
| WO | WO 2006/081425 | 8/2006 |
| WO | WO 2006/088919 | 8/2006 |
| WO | WO 2006/095542 | 9/2006 |
| WO | WO 2006/127379 | 11/2006 |
| WO | WO 2006/128129 | 11/2006 |
| WO | WO 2006/128172 | 11/2006 |
| WO | WO 2006/130462 | 12/2006 |
| WO | WO 2007/000432 | 1/2007 |
| WO | WO 2007/037898 | 4/2007 |
| WO | WO 2007/050980 | 5/2007 |
| WO | WO 2007/060404 | 5/2007 |
| WO | WO 2007/106503 | 9/2007 |
| WO | WO 2008/083491 | 7/2008 |
| WO | WO 2008/148074 | 12/2008 |
| WO | WO 2009/079797 | 7/2009 |
| WO | WO 2010/089993 | 8/2010 |

OTHER PUBLICATIONS

Akashi et al. (2008) Br J Cancer 98: 749-755, "Enhancement of the antitumor activity of ionising radiation by nimotuzumab, a humanized monoclonal antibody to the epidermal growth factor receptor, in non-small cell lung cancer cell lines of differing epidermal growth factor receptor status".
Akeakanat et al. (2007) Biochem Biophys Res Commun 362: 330-333, "Rapamycin regulates the phosphorylation of rictor." Abstract.
Alessi et al. (1997) Curr Biol 7: 261-269, "Characterization of a 3-phosphoinositide-dependent protein kinase which phosphorylates and activities protein kinase Balpha" abstract.
Alessi et al. (1997) Curr Biol 7: 776-789, "3-Phosphoinositide-dependent protein kinase-1 (PDKI): structural and functional homology with the *Drosophila* DSTPK61 kinase" abstract.
Al-Shahrour et al. (2007) Nucleic Acids Research 35:w91-w96, "FatiGO1: a functional profiling tool for genomic data. Integration of functional annotation, regulatory motifs and interaction data with microarray experiments".
Altomare et al. (2004) Oncogene 23: 5853-5857, "AKT and mTOR phosphorylation is frequently detected in ovarian cancer and can be targeted to disrupt ovarian tumor cell growth" abstract.
Altomare et al. (2005) Oncogene 24: 7455-7464, "Perturbations of the AKT signaling pathway in human cancer" abstract.
Ananthanarayanan et al. (2007) J Biol Chem 282: 36634-36641, "Live-cell molecular analysis of Akt activation reveals roles for activation loop phosphorylation" abstract.

(56) References Cited

OTHER PUBLICATIONS

Anderson et al., "Some Heterocyclic Thiosemicarbazones", Oct. 1951, Journal of the American Chemical Society, vol. 73, p. 4967-4968.
Andes et al. (2002) International Journal of Antimicrobial Agents, 19:261-268, "Animal model pharmacokinetics and pharmacodynamics: a critical review".
Andrews et al. (1990) Cancer Communications 2(2):93-100, "Rapid emergence of acquired cis-Diamminedichloroplatinum(II) Resistance in an in vivo model of human ovarian carcinoma".
Attoub et al. (2002) Cancer Research 62:4879-4883, "The c-kit tyrosine kinase inhibitor STI571 for colorectal cancer therapy".
Bain et al. (1997) Polyhedron 16(5):855-862, Synthetic and spectroscopic investigations of.
Banker et al, (2002) Journal of Pharmaceutical Sciences 92(5):967-974, "Development and validation of a 96-well equilibrium dialysis apparatus for measuring plasma protein binding".
Bastos et al., (2005) Tetrahedron, vol. 61, p. 7045-7053, "Structural analyses of 4-benzoylpyridine thiosemicarbazone using NMR techniques and theoretical calculations".
Bauer (1963) British Journal of Experimental Pathology, 44, 233-42. "The Chemotherapy of Ectromelia Infection with Isatin B-Dialkylthiosemicarbazones".
Beeram et al, (2005) J Clin Onco 23: 6771-6790, "Raf: a strategic target for therapeutic development against cancer" abstract.
Bellacosa et al. (2005) Adv Cancer Res 94: 29-86, "Activation of AKT kinases m cancer: implications for therapeutic targeting" abstract.
Beraldo et al., (2003) Journal of Molecular Structure, vol. 645, p. 213-220"Structural studies and spectral characteristics of 4-benzoylpyridine thiosemicarbazone and N(4')-phenyl-4-benzoylpyridine thiosemicarbazone".
Bernhardt et al. (2003) Journal of Biological Inorganic Chemistry pp. 866-880, "Cytotoxic iron chelators: characterization of the structure, solution chemistry and redox activity of ligands and iron complexes of the di-2-pyridyl ketone isonicotinoyl hydrazone (HPKIH) analogues" http://dx.doi.org/I0.1007 /s00775-003-0486-z.
Bernhardt et al (2008) Journal of Biological Inorganic Chemistry 13:107-119, "Tuning the antiproliferative activity of biologically active iron chelators: characterization of the coordination chemistry and biological efficacy of 2-acetylpyridine and 2-benzoylpyridine hydrazone ligands".
Berns et al. (2007) Cancer Cell 12:395-402, "A Functional Genetic Approach Identifies the PI3K Pathway as a Major Determinant of Trastuzumab Resistance in Breast Cancer".
Bjornsson et al, (2003) Drug Metabolism and Disposition 31:815-832, "The conduct of in vitro and in vivo drug-drug interaction studies: a pharmaceutical research and manufacturers of america (phrma) perspective".
Bjornsti et al. (2004) Nat Rev Cancer 4: 335-348 Ref ID: 15-4, "The TOR pathway: a target for cancer therapy" abstract.
Bolen (1993) Oncogene 8:2025-2031, "Nonreceptor tyrosine protein kinases".
Bondar et al. (2002) Mol Cancer Ther 1: 989-997, "Inhibition of the phosphatidylinositol 3'-kinase-AKT pathway induces apoptosis in pancreatic carcinoma cells in vitro and in vivo" abstract.
Bose et al. (2009) Exp Cell Res 315: 649-658, "The ErbB kinase domain: structural perspectives into Kinase activation and inhibition" abstract.
Bowery et al. (2005) Current Opinion in Pharmacology 5(4):341-448, "Cancer/Immunomodulation".
Braun (1978) Monalshefte fur Chemie 109:63-71, "4,5•Diacylpyidazine. Synthese and Umsetzung zu 1,4-Diaryl-bzw. 1,4-Dialkyl-pyridazino[4,5-d]pyridazinen" English Abstract.
Braun et al. (2008) Clin Cancer Res 14: 2249-2252, "Targeting Ras in myeloid leukemias" abstract.
Braun et al., "4,5-Diacylpyridazine: Synthese und Umsetzung zu 1,4-Diaryl-bzw. 1,4-Dialkyl-pyridazino [4,5-d] pyridazinen" 1978, Monatshefte fur Chemie 109, pp. 63-71.

Britten et al. (1999) Cancer Research 59:1049-1053, "Enhanced antitumor activity of 6-hydroxymethylacylfulvene in combination with irinotecan and 5-fluorouracil in the HT29 human colon tumor xenograft model".
Brognard et al. (2001) Cancer Res 61: 3986-3997, "Akt/protein kinase B is constitutively active in non-small cell lung cancer cells and promotes cellular survival and resistance to chemotherapy and radiation" abstract.
Brunn et al. (1996) The EMBO Journal 15(19):5256-5267, "Direct inhibition of the signaling functions of the mammalian target of rapamycin by the phosphoinositide 3-kinase inhibitors, wortmannin and LV294002".
Buck et al. (2006) Mol Cancer Ther 5: 2676-2684, "Rapamycin synergizes with the epidermal growth factor receptor inhibitor erlotinib in non-small-cell lung, pancreatic, colon, and breast tumors" abstract.
Byrn et al., Solid-State Chemistry of of Drugs, 516 (2nd ed., 1999). "Hydrates are a subset of solvates wherein the solvent is water", id. at 233-247, pp. 233-234.
Canadian Intellectual Property Office acting as International Searching Authority, International Search Report and Written Opinion prepared Mar. 2, 2009 for International Application No. PCT/CA2008/002293, 12 pages.
Canadian Intellectual Property Office acting as International Searching Authority, International Search Report prepared Apr. 28, 2008 for International Application No. PCT/CA2008/000045, 5 pages.
Canadian Intellectual Property Office acting as International Searching Authority, International Search Report prepared Sep. 22, 2009 and Written Opinion prepared Oct. 28, 2009 for International Application No. PCT/CA2009/00I004, 15 pages.
Canadian Intellectual Property Office acting as International Searching Authority, Written Opinion of the International Searching Authority prepared Apr. 28, 2008 for International Application No. PCT/CA2008/000045, 6 pages.
Caron et al. (2005) Mol Cancer Ther 4: 257-270, "Activated forms of H-RAS and K-RAS differentially regulate membrane association of PI3K, PDK-1, and AKT and the effect of therapeutic kinase inhibitors on cell survival" abstract.
CAS Registry No. 76780-41-1, 2 pages.
CAS Registry No. 868364-38-9, Nov. 18, 2005.
CAS Registry No. 868364-43-6, Nov. 18, 2005.
CAS Registry No. 901285-15-2, Aug. 15, 2006.
CAS Registry No. 901329-97-3, Aug. 15, 2006.
CAS Registry No. 901348-18-3, Aug. 15, 2006.
CAS Registry No. 901349-50-6, Aug. 15, 2006.
CAS Registry No. 901360-08-5, Aug. 15, 2006.
CAS Registry No. 901391-84-2, Aug. 15, 2006.
CAS Registry No. 903180-32-5, Aug. 22, 2006.
CAS Registry No. 903274-24-8, Aug. 26, 2006.
CAS Registry No. 91189-95-6, Nov. 16, 1984.
CAS Registry No. 500300-93-6, Mar. 24, 2003.
CAS Registry No. 518299-22-4, May 21, 2003.
CAS Registry No. 519151-42-9, May 23, 2003.
CAS Registry No. 549530-64-5, Jul. 17, 2003.
CAS Registry No. 732257-35-1, Aug. 25, 2004.
CAS Registry No. 732992-68-6, Aug. 26, 2004.
CAS Registry No. 733793-43-6, Aug. 27, 2004.
CAS Registry No. 802269-45-0, Dec. 23, 2004.
CAS Registry No. 847046-07-5, Mar. 23, 2005.
CAS Registry No. 852401-92-4, Jun. 16, 2005.
CAS Registry No. 852401-95-7, Jun. 16, 2005.
Castagnola et al. (2005) Biochim Biophys Acta 1756: 115-125, "Mutant KRAS, chromosomal instability and prognosis in colorectal cancer" abstract.
Castillo et al, (2004) Cancer Res 64: 2782-2792, "Preferential inhibition of Akt and killing of Akt-dependent cancer cells by rationally designed phosphatidylinositol ether lipid analogues."
Castro-Carpeno et al. (2008) Clin Transl Onco/1 0: 6-13. "EGFR and colon cancer: a clinical view" abstract.
Cespedes et al. (2006) Carcinogenesis 27: 2190-2200, "K-ras Asp12 mutant neither interacts with Raf, nor signals through Erk and is less tumorigenic than K-ras Val12" abstract.

(56) References Cited

OTHER PUBLICATIONS

Chadha et al. (2006) Ann Surg Oncol 13: 933-939, "Activated Akt and Erk expression and survival after surgery in pancreatic carcinoma" abstract.
Chau et al. (2,009) Br J Cancer 100:1704-1719, "Treatment in advanced colorectal cancer: what, when and how?" abstract.
CHEMCATS record, CAS Registry No. 903274-24-8, 903180-32-5, 901391-84-2, 901360-35-8, 901360-08-5, 901349-50-6 01348-18-3, 901329-97-3, 901285-15-2, 847046-07-5, 802269-45-0, 733793-43-6, 732992-68-6, 732257-35-1, 519151-42-9, 501650-12-0, 500300-93-6 (10 pages).
Chen et al. (2001) J Biol Chem 276: 31858-31862, "Regulation of Akt/PKB activation by tyrosine phosphorylation" abstract.
Cheng et al. (1992) Proc Natl Acad Sci U S A 89: 9267-9271, "AKT2, a putative oncogene encoding a member of a subfamily of protein-serine/threonine kinases, is amplified in human ovarian carcinomas" abstract.
Cheng et al. (1996) Proc Natl Acad Sci U S A 93: 3636-364:1, "Amplification of AKT2 in human pancreatic cells and inhibition of AKT2 expression and tumorigenicity by antisense RNA" abstract.
Cheng et al. (2005) Oncogene 24: 7482-7492, "The Akt/PKB pathway: molecular target for cancer drug discovery" abstract.
Chiang et al. (2007) Trends in Molecular Medicine 13:433-442, "Targeting the mTOR signaling network in cancer".
Chiang et al. (2007) Trends in Molecular Medicine 13:433-442 "Targeting the inTOR signaling network in cancer" abstract.
Chou et al. (1983) Trends in Pharm Sci 4:450-454, "Analysis of combined drug effects: a new look at a very old problem".
Chou (2006) Pharmacol Rev 58:621-681, "Theoretical Basis, Experimental Design, and Computerized Simulation of Synergism and Antagonism in Drug Combination Studies".
Choudhary et al. (1998) Journal of the Indian Chemical Society, 75, 392-394, "Structural Aspects of Morpholine-N-thiohydrazone Complexes with sonic Bivalent Metals".
Clark et al, (2002) Mol Cancer Ther 1: 707-717, "Constitutive and inducible Akt activity promotes resistance to chemotherapy, trastuzumab, or tamoxifen in breast cancer cells" abstract.
Copp et al. (2009) Cancer Res 69: 1821-1827, "TORC-specific phosphorylation of mammalian target of rapamycin (mTOR): phospho-Ser2481 is a marker for intact mTOR signaling complex 2" abstract.
Cully et al. (2006) Nature 6:184-192, "Beyond PTEN mutations: the PI3K pathway as an integrator of multiple inputs during tumorigenesis".
Dacie, S. (2008) Adv Anat Pathol 15: 241-247, "EGFR assays in lung cancer" abstract.
Datta et al. (1999) Genes Dev 13: 2905-2927, "Cellular survival: a play in three Akts" abstract.
Dannis et al. (1970) Bull. Soc. Chim. Fr., No. 6:2289-2291, "Semicarbazones et thiosemicarbazones N-4 substituees de l'isatine".
de Gunzburg, J. (1999) Cell Bioi Toxicol 15: 345-358, "Proteins of the Ras pathway as novel potential anticancer therapeutic targets" abstract.
Decaudin (2005) Int. J. Cancer 113:849-856, "In vivo efficacy of STI571 in xenografted human small cell lung cancer alone or combined with chemotherapy".
Defeo-Jones et al. (2005) Mol Cancer Ther 4:271-279, "Tumor cell sensitization to apoptotic stimuli by selective inhibition of specific Akt/PKB family members" abstract.
DeGraffenried et al. M (2004) Ann Oncol 15: 1510-1516, "Reduced PTEN expression in breast cancer cells confers susceptibility to inhibitors of the PI3 kinase/Akt pathway" abstract.
Deramaudt T, Rustgi AK (2005) Biochim Biophys Acta 1756:97-101, "Mutant KRAS in the initiation of pancreatic cancer".
Dierks et al. (2001) Drug Metabolism and Disposition 29:23-29, "A method for the simultaneous evaluation of the activities of seven major human drug-metabolizing cytochrome P450S using an in vitro cocktail of probe substrates and fast gradient liquid chromatography tandem mass spectrometry".

Dobashi et al. (2009) Cancer 115: 107-118, "Critical and diverse involvement of Akt/mammalian target of rapamycin signaling in human lung carcinomas" abstract.
Doody et al. (2007) Mol Cancer Ther 6: 2642-2651, "Inhibitory activity of cetuximab on epidermal growth factor receptor mutations in non-small cell lung cancers" abstract.
Dowling et al, (2009) BioDrugs 23: 77-91, "Current status and challenges associated with targeting mTOR for cancer therapy" abstract.
Downward, J. (2003) Nat Rev Cancer 3: 11-22, "Targeting RAS signalling pathways in cancer therapy" abstract.
Du K, Tsichlis PN (2005) Oncogene 24: 7401-7409, "Regulation of the Akt kinase by interacting proteins" abstract.
Duca et al., (1952) Antibiotics and Chemotherapy, 11(1):16-20, "Studies in Experimental Tuberculosis In Vitro and In Vivo Activities of Thiosemicarbazones".
Dwivedi et al. (1995) J. Indian Chem, Soc. 72:403-405, "Donor Behaviour of some Motpholine-N-thiohydrazoneswith some Bivalent Metal Ions".
Dziadulewicz et al. (2001) Bioorganic and Medicinal Organic Letters, 11, 705-709, "Design of Non-Peptide $CCK_2$ and $NK_1$ Peptidomimetics Using 1-(2-Nitrophenyl)thiosemicarbazide as a Novel Common Scaffold".
Easmon et al., "Pyridazines 47,1 the Configuration of Novel Thiosemicarbazone Derivatives of Pyridazinecarbaldehydes and Alkyl Pyridazinyl Ketones", 1989, Heterocycles, vol. 29, No. 7, pp. 1399-1408.
Easmon et al., "Synthesis and Antiviral Activity of Thiosemicarbazone Derivatives of Pyridazinecarbaldehydes and Alkyl Pyridazinyl Ketones", 1989, Arzneim-Forsch/Drug Res. 39 (II), No. 10.
El Rayes et al. (2006) Cancer Res 66: 10553-10559, "Potentiation of the effect of erlotinib by genistein in pancreatic cancer: the role of Akt and nuclear factor-kappaB" abstract.
Eliel et al. (1994) A Wiley-Interscience Publication: Stereochemistry of Organic Compounds, ch.14: 1119-1190, "Chirality in molecilles devoid of chiral centers".
Ellis et al, (2000) Cell Signal 12: 425-434, "The importance of being K-Ras" abstract.
Engelman et al. (2008) Clin Cancer Res 14: 2895-2899, "Mechanisms of acquired resistance to epidermal growth factor receptor tyrosine kinase inhibitors in non-small cell lung cancer" abstract.
Engelman et al. (2008) Nat Med 14: 1351-1356, "Effective use of PI3K and MEK inhibitors to treat mutant Kras G 12D and PIK3CA H1047R murine lung cancers" abstract.
Engelman, JA (2009) Nat Rev Cancer 9: 550-562, "Targeting PI3K signalling in cancer: opportunities, challenges and limitations" abstract.
Europe Application No, 08700510.4-2:117 Examination Report mailed Feb. 22, 2012.
EP Examination for EP Application No. 09797322.6 dated Sep. 10, 2012, 7 pages.
EP Examination for EP Application No. 08700510.4 dated Jan. 16, 2013, 5 pages.
European Supplemental Search Report for EP Application No. 09797322 mailed Dec. 20, 2011.
Fakih M (2008) Curr Treat Options Oncol 9: 357-374, "The role of targeted therapy in the treatment of advanced colorectal cancer" abstract.
Feldman et al, (2009) PLoS Biol 7:e38, "Active-site inhibitors of mTOR target rapamycin-resistant outputs of mTOR,C1 and mTORC2" abstract.
Fischer et al. (2007) Cancer Treat Rev 33: 391-406, "Targeting receptor tyrosine kinase signalling in small cell lung cancer (SCLC): what have we learned so far?" abstract.
Fotiadou et al. (2007) Mol Cell Biol 27: 6742-6755, "Wild-type NRas and KRas perform distinct functions during transformation" abstract.
Franke et al (2003) Oncogene 22: 8983-8998, "PI3K/Akt and apoptosis: size matters" abstract.
Franke et al. (2006) The American Journal of Human. Genetics 78: 1011-1025, "Reconstruction of a functional human gene network, with an application for prioritizing positional candidate genes".

(56) References Cited

OTHER PUBLICATIONS

French et al. (1966) J Med Chem 9(4):585-589, "The carcinostatic activity of thiosemicarhazones of formyl heteroaromatic compounds. III. Primary correlation".

Friday et al. (2005) Biochim Riophys Acta 1756: 127-144, "K-ras as a target for cancer therapy" abstract.

Fukui et al. (2008) Gen Thorac Cardiovasc Surg 56: 97-103, "Mutations in the epidermal growth factor receptor gene and effects of EGFR-tyrosine kinase inhibitors on lung cancers" abstract.

Furukawa, T. (2008) J Gastroenterol 43: 905-911, "Molecular targeting therapy for pancreatic cancer: current knowledge and perspectives from bench to bedside".

Gadducci et al. (2008) Gynecol Endocrinol 24: 239-249, "Molecular target therapies in endometrial cancer: from the basic research to the clinic" abstract.

Garassino et al. (2009) Anticancer Res 29: 2691-2701, "Biological and clinical features in predicting efficacy of epidermal growth factor receptor tyrosine kinase inhibitors: a systematic review and meta-analysis" abstract.

Gazdar, AF (2009) Oncogene 28 Suppl1: S24-S31, "Activating and resistance mutations of EGFR in non-small-cell lung cancer: role in clinical response to EGFR tyrosine kinase inhibitors" abstract.

Granville et al. (2006) Clin Cancer Res 12(3):679-689, "Handicapping the race to develop inhibitors of the phosphoinositide 3-Kinase/Akt/Mammalian target of rapamycin pathway".

Gres et al (1998) Pharmaceutical Research 15(5):726-733, "Correlation between oral drug absorption in humans, and apparent drug permeability in TC-7 cells, a human epithelial intestinal cell line: comparison with the parental caco-2 cell line".

Gridelli et al. (2008) Oncologist 13: 139-147, "The potential role of mTOR inhibitors in non-small cell lung cancer".

Guerrero et al. (2002) FASEB J 16: 1642-1644, "Codon 12 and codon 13 mutations at the K-ras gene induce different soft tissue sarcoma types in nude mice" abstract.

Guertin et al. (2007) Cancer Cell 12: 9-22, "Defining the role of mTOR in cancer" abstract.

Gururaja et al. (2006) Clin Cancer Res 12(12)3831-3842, "R-253 disrupts microtubule networks in multiple tumor cell lines".

Guzeloglu et al. (2004) Biol Reprod 71: 714-721, "In vivo and in vitro regulation of Akt activation in human endometrial cells is estrogen dependent" abstract.

Hartmann et al. (2006) Clin Cancer Res 12: 3019-3027, "Phosphatidylinositol 3'-kinase/AKT signaling is activated in medulloblastoma cell proliferation and is associated with reduced expression ofPTEN" abstract.

Hay, N. (2005) Cancer Cell 8: 179-183, "The Akt-mTOR tango and its relevance to cancer".

Heinemann et al. (2009) Cancer Treat Rev 35:262-271, "Clinical relevance of EGFR- and KRAS-status in colorectal cancer patients treated with monoclonal antibodies directed against the EGFR" abtract.

Heinisch et al. (1972) Journal fur Prakt. Chemie. Band 314, 682-698, "Synthesis und Struktur substituierter Isatinthiosemicarbazone und -isothiosemicarbazone".

Heinisch et al., "Symhesen und Reaktionen von Pyridazinderviaten", 1973, Monatshefte fur Chemie 104, pp. 1372-1382.

Helfrich et al. (2006) Clin Cancer Res 12: 7117-7125, "Antitumor activity of the epidermal growth factor receptor (EGFR) tyrosine kinase inhibitor gefitinib (ZD1839, Iressa) in non-small cell lung cancer cell lines correlates with gene copy number and EGFR mutations but not EGFR protein levels" abstract.

Hennessy et al. (2005) Nat Rev Drug Discov 4: 988-1004, "Exploiting the PI3K/AKT pathway for cancer drug discovery" abstract.

Hennessy et al. (2005) Nat Rev Drug Discov 4: 988-1004, "Exploiting the PI3K/AKT pathway for cancer drug discovery".

Hirsch et al. (2006) J Clin Oncol 24: 5034-5042, "Molecular predictors of outcome with gefitinib in a phase III placebo-controlled study in advanced non-small-cell lung cancer" abstract.

Ho Sui et al. (2005) Nucleic Acids Research 33(10)3154-3164, "oPOSSUM: identification of over-epresented transcription factor binding sites in co-expressed genes".

Holland et al. (2000) Nat Genet 25: 55-57, "Combined activation of Ras and Akt in neural progenitors induces glioblastoma formation in mice" abstract.

Roulston, RS (2001) Mol Pathol 54: 206-214, "What we could do now: molecular pathology of colorectal cancer" abstract.

Huang et al (2004) Cancer Res 64: 5355-5362, "Dual-agent molecular targeting of the epidermal growth factor receptor (EGFR): combining anti-EGFR antibody with tyrosine kinase inhibitor" abstract.

Huang et al. (2006) Mol Cell Proteomics 5: 1045-1053, "Interdomain conformational changes in Akt activation revealed by chemical cross-linking a d tandem mass spectrometry" abstract.

Huang et al. (2009) Biochem Soc Trans 37: 217-222, "A complex interplay between Akt, TSC2 and the two mTOR complexes" abstract.

Huang et al. (2009) J Formos Med Assoc 108: 180-194, "Induction of Akt activity by chemotherapy confers acquired resistance" abstract.

Hynes et al. (2009) Curr Opin Cell Biol 21: 177-184, "ErbB receptors and signaling pathways in cancer" abstract.

Ikeda et al. (2007) Pathol Int 57: 268-275, "Correlation between EGFR gene mutation pattern and Akt phosphorylation in pulmonary adenocarcinomas" abstract.

International Search Report for International Application No. PCT/US2005/021253 mailed Mar. 29, 2006.

Itoh et al. (2002) Cancer 94: 3127-3134, "Phosphorylation of Akt/PKB is required for suppression of cancer cell apoptosis and tumor progression in human colorectal carcinoma" abstract.

Izzard et al. (1999) Cancer Research 59:2581-2586, "Competitive and noncompetitive inhibition of the DNA-dependent protein kinase".

Jacinto et al, (2006) Cell 127: 125-137, "SINI/MIPI maintains rictor-mTOR complex integrity and regulates Akt phosphorylation and substrate specificity" abstract.

Janmaat et al. (2003) Clin Cancer Res 9: 2316-2326, "Response to epidermal growth factor receptor inhibitors in non-small cell lung cancer cells: limited antiproliferative effects and absence of apoptosis associated with persistent activity of extracellular signal-regulated kinase or Akt kinase pathways" abstract.

Janmaat et al. (2006) Int J Cancer 118: 209-214, "Enhanced cytotoxicity induced by gefitinib and specific inhibitors of the Ras or phosphatidyl inositol-3 kinase pathways in non-small cell lung cancer cells" abstract.

Janne, PA (2008) Lung Cancer 60 Suppl 2; S3-S9, "Challenges of detecting EGFR T790M in gefitinib/erlotinib-resistant tumours" abstract.

Jetzt et al. (2003) Cancer Res 63: 6697-6706, "Adenoviral-mediated expression of a kinase-dead mutant of Akt induces apoptosis selectively in tumor cells and suppresses tumor growth in mice" abstract.

Ji et al. (2007) J Biol Chern 282: 14048-14055, "Oncogenic KRAS activates hedgehog signaling pathway in pancreatic cancer cells" abstract.

Jiang et al. (2000) Mol Cell Biol 20: 139-148, "The phosphoinositide 3-0H kinase/AKT2 pathway as a critical target for farnesyltransferase inhibitor-induced apoptosis" abstract.

Jiang et al. (2008) Drug Resist Updat 11: 63-76, "Role of inTOR in anticancer drug resistance: perspectives for improved drug treatment" abstract.

Jiang et al. (2009) Adv Cancer Res 102: 19-65, "PI3K/PTEN signaling angiogenesis and tumorigenesis" abstract.

Jiang et al. (2009) Cancer 115: 3609-3617, "Assessment of K-ras mutation: a step toward personalized medicine for patients with colorectal cancer" abstract.

Jimeno et al. (2009) Cancer J 15: 110-113, "KRAS mutations and susceptibility to cetuximab and oanitumumab in colorectal cancer" abstract.

(56) References Cited

OTHER PUBLICATIONS

Jimeno et al. (2009) J Clin Oncol 27: 1130-1136, "KRAS mutations and sensitivity to epidermal growth factor receptor inhibitors in colorectal cancer: practical application of patient selection" abstract.
John et al. (2009) Oncogene 28 Suppl 1: S14-S23, "Overview of molecular testing in non-small-cell lung cancer: mutational analysis, gene copy number, protein expression and other biomarkers of EGFR for the prediction of response to tyrosine kinase inhibitors" abstract.
Joshi et al., "Organic Pesticides. Part XIII. Synthesis of Some New Fluoro-ketones and their Thiosemicarbazones", 1963, Journal ofindian Chemical Society, vol. 40, No. 1, p. 42-44.
Kalinowski et al., "Design, Synthesis, and Characterization of Novel Iron Chelators: Structure-Activity Relationships of the 2-Benzoylpyridine Thiosemicarbazone Series and Their 3-Nitrobenzoyl Analogues as Potent Antitumor Agents", 2007, J. Med. Chem., 50, pp. 3716-3729.
Kandasamy et al. (2002) Cancer Res 62: 4929-4937, "Role of the phosphatidylinositol 3'- kinase/PTEN/Akt kinase pathway in tumor necrosis factor-related apoptosis-inducing ligand-induced apoptosis in non-small cell lung cancer cells" abstract.
Kang et al. (2008) Int J. Gynecol Cancer 18: 1339-1343, "Mutual exclusiveness between PIK3CA and KRAS mutations in endometrial carcinoma" abstract.
Kim et al. (2002) J Biochem Mol Biol 35: 106-115, "Akt: versatile mediator of cell survival and beyond" abstract.
Kimura et al. (2007) Cancer Sci 98: 12751280, "Antibody-dependent cellular cytotoxicity of cetuximab against tumor cells with wild-type or mutant epidermal growth factor receptor" abstract.
Klein et al. (2009) Curr Opin Cell Bioi 21 : 185-193, "Targeting the EGFR and the PKB pathway in cancer" abstract.
Kobayashi et al. (2005) N Engl J Med 352: 786792, "EGFR mutation and resistance of non-small-cell lung cancer to gefitinib" abstract.
Konstantinopoulos et al. (2007) Nat Rev Drug Discov 6: 541-555, "Post-translational modifications and regulation of the RAS superfamily of GTPases as anticancer targets" abstract.
Krause et al (2005) New England Journal of Medicine 353(2): 172-187 "Tyrosine kinases as targets for cancer therapy".
Kurman et al. (2008) Int J Gynecol Pathol 27: 151-160, "Pathogenesis of ovarian cancer: lessons from morphology and molecular biology and their clinical implications" abstract.
Labisbal et al. (2000) Polyhedron, 19, 1255-1262, "Spectral and structural studies of metal complexes of isatin 3-hexamethyleneiminylthiosemicarbazone prepared electrochemically".
Ladanyi et al. (2008) Mod Pathol 21 Suppl 2: S16-S22, "Lung adenocarcinoma: guiding EGFR-targeted therapy and beyond" abstract.
Laurent-Puig et al. (2008) Curt Opin Onco/20: 454-458, "Lessons from Tarceva in pancreatic cancer: where are we now, and how should future trials be designed in pancreatic cancer?" abstract.
Laurent-Puig et al. (2009) Clin Cancer Res 15: 1133-1139, "Mutations and response to epidermal growth factor receptor inhibitors" abstract.
le Coutre et al. (1999) Jrnl National Cancer Institute 91(2): 163-168, In vivo eradication of human BCR/ABL-Positive leukemia cells with an ABL kinase inhibitor.
Lee et al., A Polynucleotide Segment Rich in Adenylic Acid in the Rapidly-Labeled Polyribosomal RNA Component of Mouse Sarcoma 180 Ascites Cells, Proc. Nat. Acad. Sci. USA, Vol, 68, (1971), 1331-1335.
Lee et al. (2005) Clin Cancer Res 11: 6065-607-4, "Response of non-small cell lung cancer cells to the inhibitors of phosphatidylinositol 3-kinase/Akt- and MAPK kinase 4/c-Jun NH2-terminal kinase pathways: an effective therapeutic strategy for lung cancer" abstract.
Lee et al. (2008) Int J Cancer 122: 2380-2384, "Aktl inhibition by RNA interference sensitizes human non-small cell lung cancer cells to cisplatin" abstract.
Legrier et al. (2007) Cancer Res 67: 11300-11308, "Targeting protein translation in human non-small cell lung cancer via combined MEK and mammalian target of rapamycin suppression" abstract.
Lev et al. (2005) Clinical Cancer Research 11:306-314, "Inhibition of platelet-derived growth factor eceptor signaling restricts the growth of human breast cancer in the bone of nude mice".
Lievre et al. (2006) Cancer Res 66(8):3992-3995, "KRAS mutation status is predictive of response to cetuximab therapy in colorectal cancer".
Lin et al. (2005) Br J Cancer 93: 1372-1381, "Elevated phosphorylation and activation of PDK-1/AKT pathway in human breast cancer" abstract.
Linardou et al. (2008) Lancet Oneol 9: 962-972, "Assessment of somatic k-RAS mutations as a mechanism associated with resistance to EGFR-targeted agents: a systematic review and meta-analysis of studies in advanced non-small-cell lung cancer and metastatic colorectal cancer" abstract.
Liscovitch et al. (2002) Drugs 5(4):349-355, "Cancer multidrug resistance: A review of recent drug discovery research".
Lister et al. (1970) Journal of the Chemical Society, 1313-1315, "Potentially Chemotherapeutic Purine Analogues, Part V. Some Hydrazone Derivatives of Pyrazole-4,5-diones and their Cyclisation to Pyrazolo [3,4-e][1,2,4]triazines".
Liu et al. (2007) Clin Cancer Res 13: 67886795, "Relationship of EGFR mutations, expression, amplification, and polymorphisms to epidermal growth factor receptor inhibitors in the NCI60 cell lines." abstract.
Liu et al. (2008) PLoS One 3: e2850, "K-ras/PI3K-Akt signaling s essential for zebrafish hematopoiesis and angiogenesis" abstract.
Liu et al, (2009) Nat Rev Drug Discov 8: 627-644, "Targeting the phosphoinositide 3-kinase pathway in cancer" abstract.
LoPiccolo et al. (2008) Drug Resist Updat 11: 32-50, "Targeting the PI3K/Akt/mTOR pathway: effective combinations and clinical considerations" abstract.
Mahoney et al. (2009) Br J Cancer 100: 370-375, "LKBI/KRAS mutant lung cancers constitute a genetic subset of NSCLC with increased sensitivity to MAPK and mTOR signalling inhibition" abstract.
Manning et al. (2007) Cell 129: 1261-1274 Ref ID: 125, "AKT/PKB signaling: navigating downstream" abstract.
Manning (2009) Biochem Soc Trans 37:217-222, "A complex interplay between Akt, TSC2 and the two mTOR complexes" abstract.
MAPK Antibody is used to control for loading and specificity of PTEN siRNA (data obtained from Cell Signaling Technology website, http://www.cellsignal.eom/produets/6251.html) 3 pages.
Martelli et al. (2006) Leukemia 20: 911-928, "Phosphoinositide 3-kinase/Akt signaling pathway and its therapeutical implications for human acute myeloid leukemia" abstract.
Massion et al. (2004) Am J Respir Crit Care Med 170: 1088-1094, "Early involvement ofthe phosphatidylinositol 3-kinase/Akt pathway in lun_g cancer pro_gression" abstract.
Masure et al. (1999) Eur J Biochem 265: 353-360, "Molecular cloning, expression and characterization of the human serine/threonine kinase Akt-3" abstract.
McCubrey et al. (2008) Adv Enzyme Regul 48: 113-135, "Alteration of Akt activity increases chemotherapeutic drug and hormonal resistance in breast cancer yet confers an achilles heel by sensitization to targeted therapy" abstract.
McNeill (1973) Antimicrobial Agents and Chemotherapy 4(2):105-108, "Inhibitio of granulocyte-macrophage colony formation in vitro by substituted isatinthiosemicarbazones".
McNeill, "Inhibition of Granulocyte-Macrophage Colony Formation In Vitro by Substituted Isatin Thiosemicarbazones", Aug. 1, 1973, vol. 4, No. 2, pp. 105-108.
Memmott (2009) Cell Signal 21: 656-664, "Akt-dependent and -independent mechanisms of mTOR regulation in cancer" abstract.
Meric-Bernstam et al. (2009) J Clin Oncol 27: 2278-2287, "Targeting the mTOR signaling network for cancer therapy" abstract.

(56) References Cited

OTHER PUBLICATIONS

Minaguchi et al. (2007) Cancer Lett 248: 112-122, "Combined phospho-Akt and PTEN expressions associated with post-treatment hysterectomy after conservative progestin therapy in complex atypical hyperplasia and stage Ia, G1 adenocarcinoma of the endometrium" abstract.
Miller III, et al., "The Cytotoxicity of Copper(II) Complexes of 2-Acetyl-Pyridyl-N-Substituted Thiosemicarbazones", 1998, Anticancer Research 18, pp. 4131-4140.
Missbach (1996) Journal of Biological Chemistry 271, 13515-13522, "Thiazolidine Diones, Specific Ligands of the Nuclear Receptor Retinoid Z Receptor/Retinoid Acid Receptor-related Orphan Receptor α with Potent Antiarthritic Activity".
Monks et al. (1991) National Cancer Institute 83(11)757-766, "Feasibility of a high-flux anticancer drug screen using a diverse panel of cultured human tumor cell lines".
Montgomery et al., Inhibition of solid Tumors by Nitrosoureas, I. Lewis Lung Carcinoma. J. Med. Chem., (1977), vol. 20, No. 2, 291-295.
Morgan et al. (1983), International Journal of Applied Radiation and Isotopes, 34(11), 1501-1504, "Synthesis of $[1-^{14}C]$ 1,2-Cyclohexanedione bis(4-diethylenoxythiosemicarbazone) and Preliminary Biodistribution Studies of this Potential Antitumor Agent".
Morgensztern et al. (2005) Anticancer Drugs 16: 797-803, "PI3K/Akt/mTOR pathway as a target for cancer therapy" abstract.
Nelson et al. (2007) Prostate Cancer Prostatic Dis 10: 331-339, "Inhibition of Akt pathways in the treatment of prostate cancer".
Normanno et al. (2006) Gene 366: 2-16, "Epidermal growth factor receptor (EGFR) signaling in cancer" abstract.
Noske et al. (2007) Cancer Lett 246: 190-200, "Specific inhibition of AKT2 by RNA interference esults in reduction of ovarian cancer cell proliferation: increased expression of AKT in advanced ovarian cancer" abstract.
NSC No. 84442-R, National Cancer Institute, 5 pages.
O'Sullivan et al. (1963), Chemotherapia, 7, 17-26, "A Study of the Chemotherapeutic Activity of satin B-4',4'-Dialkylthiosemicarbazones a_gainst Ectromelia Infection".
O'Sullivan et al. (1963), International Congress of chemotherapy, (1), 879-883, "A Study ofIsatin—Thiosemicarbazone Derivatives in Relation to the Cytopathic Changes Produced by Type 1 and Type 2 Poliovirus on Embryonic Rabbit Kidney Cells in Tissue-Culture".
Oehler-Janne et al, (2008) Biochem Biophys Res Commun 375: 399-404, "Temperature sensitivity of phospho-Ser(473)-PKB/AKT" abstract.
Okudela et al. (200-4) Am J Pathol 164: 9:1-100, "K-ras gene mutation enhances motility of immortalized airway cells and lung adenocarcinoma cells via Akt activation: possible contribution to non-invasive expansion of lung adenocarcinoma" abstract.
Ono et al. (2006) Clin Cancer Res 12: 7242-7251, "Molecular mechanisms of epidermal growth factor receptor (EGFR) activation and response to gefitinib and other EGFR-targeting drugs" abstract.
Pacifici et al. (1992) Clin Pharmacokinetics 23(6):449-468, "Methods of determining plasma and tissue binding of drugs. Pharmacokinetic consequences" abstract.
Pandyra et al. (2007) Jrnl Pharmacology and Experimental Therapeutics 322(1): 123-132, "Combination silencer RNA (siRNA) targeting Bcl-2 antagonizes siRNA against thymidylate synthase in human tumor cell lines".
Pao et al. (2005) PLoS Med 2: e73, "Acquired resistance of lung adenocarcinomas to gefitinib or erlotinib is associated with a second mutation in the EGFR kinase domain" abstract.
Pao, W (2006) Cancer Chemother Pharmacol 58 Suppl: s11-s15, "Defining clinically relevant molecular subsets of lung cancer" abstract.
Papadimitrakopoulou et al. (2006) J Thorac Oncol 1: 749-751, "The Akt/mTOR and mitogen-activated protein kinase pathways in lung cancer therapy" abstract.
Parikh et al. (2007) Cancer Res 67: 7139-7146, "Oncogenic NRAS, KRAS, and HRAS exhibit different leukemogenic potentials in mice" abstract.

Pectasides, et al., "Systemic therapy in metastatic or recurrent endometrial cancer", Mar. 3, 2007, Cancer Treatment Reviews, Saunders, US, vol. 33, No. 2, pp. 177-190.
Peterson et al. (2000) Jrnl Biological Chemistry 275(10):7416-7423, FKBP12-Rapamycin-associated protein (FRAP) autophosphorylates at serine 2481 under translationally repressive conditions.
Plesec et al. (2009) Adv Anat Pathol 16: 196-203. "KRAS mutation testing in colorectal cancer" abstract.
Plowman et al. (1994) DN&P 7(6):334-339, "Receptor tyrosine kinases as targets for drug intervention".
Prakash, et al., Effect of a-Difluoromethylornithine, an Enzyme-activated Irreversible Inhibitor of Ornithine Decarboxylase, on L1210 Leukemia in Mice, Cancer Res. 38 (1978), 3059-3062.
Prakash et al. (1989) Indian Drugs 27(2), 106-110, "Synthesis and Screening of N-Morpholino/Piperidino Thiosemicarbazones as Potential Antimicrobial Agents".
Pretlow et al. (2005) Biochim Biophys Acta 1756: 83-96, "Mutant KRAS in aberrant crypt foci (ACF): initiation of colorectal cancer?" abstract.
Raponi et al. (2008) Curr Opin Pharmacol 8: 413-418, "KRAS mutations predict response to EGFR inhibitors" abstract.
Rhodes et al. (2005) Nature Biotechnology 23(8):951-959, "Probabilistic model of the human protein-protein interaction network".
Riely et al. (2009) Proc Am Thorne Soc 6: 201-205, "KRAS mutations in non-small cell lung cancer" abstract.
Riely, GJ (2008) J Thorac Oncol 3: S146-S149, "Second-generation epidermal growth factor receptor tyrosine kinase inhibitors in non-small cell lung cancer" abstract.
Riely, GJ (2008) Lung Cancer 60 Suppl 2: S19-S22, "The use of first-generation tyrosine kinase inhibitors in patients with NSCLC and somatic EGFR mutations" abstract.
Riondel et al. (1988) Anticancer Research 8:387-390, "Antineoplastic activity of two taxol derivatives on an ovarian tumor xenografted into nude mice".
Rong et al. (2001) J Med Chem 44: 898-908, "Molecular modeling studies of the Akt PH domain and its interaction with phosphoinositides" abstract.
Rosner et al, (2008) Mutat Res 659: 284-292, "The mTOR pathway and its role in human genetic diseases" abstract.
Rosti et al. (2006) Ann Oncol 17 Suppl 5: v99-102, "Chemotherapy advances in small cell lung cancer" abstract.
Ruggeri et al. (1998) Mol Carcinog 21: 81-86, "Amplification and overexpression of the AKT2 oncogene in a subset of human pancreatic ductal adenocarcinomas" abstract.
Ruggero et al. (2005) Oncogene 24: 7426-7434, "The Akt of translational control" abstract.
Rusinov et al., "New reaction of 3,6-bis(2-pyridyl)-1,2,4,5-tetrazine with anhydro base of 1,2,3-trimethylquinoxalinium and intramolecular aminolysis of the resulting azomethine", 1981. (abstract).
Sabatini, DM (2006) Nat Rev Cancer 6: 729-734, "mTOR and cancer: insights into a complex. relationship" abstract.
Saif et al. (2009) Clin Adv Hematol Onco/7: 45-53, 64, "K-ras mutations in colorectal cancer: a practice changing discovery" abstract.
Sambuy et al. (2005) Cell Biology and Toxicology 21:1-26, "The Caco-2 cell line as a model of the intestinal barrier: influence of cell and culture-related factors on Caco-2 cell functional characteristics".
Sarbassov et al, (2004) Current Biology 14:1296-1302, "Rictor, a novel binding partner of mTOR, defines a rapamycin-insensitive and raptor-independent pathway that regulates the cytoskeleton".
Sarbassov et al. (2005) Science 307: 1098-1101, "Phosphoylation and regulation of Akt/PKB by the rictor-mTOR complex" abstract.
Schneider et al. (2003) Mol Cancer 2: 15, "Genetic alterations in pancreatic carcinoma" abstract.
Schubbert et al. (2007) Nat Rev Cancer 7: 295-308, "Hyperactive Ras in developmental disorders and cancer" abstract.
Scripture et al. (2006) Nature 6:546-558, "Drug interactions in cancer therapy".
Sebille (1990) Fundam Clin Pharmacol 4(S2): 151s-161s, "Methods of drug protein binding determinations".

(56) References Cited

OTHER PUBLICATIONS

Seeliger et al. (2007) Cancer Metastasis Rev 26: 6111-621, "Role of mTOR in solid tumor systems: a therapeutical target against primary tumor growth, metastases, and angiogenesis" abstract.
Seleem et al. (2002) Journal of the Serbian Chemical Society, 67(4), 243-256, "Thermodynamics of complexation of isatin-3-thiosemicarbazone (HIT) and other related derivatives with some metal ions".
Sequence Listing for International Application No. PCT/US2005/021253.
Sequist et al. (2008) Annu Rev Med 59:429-442, "EGFR tyrosine kinase inhibitors in lung cancer: an evolving story" abstract.
Sequist, LV (2008) J Thorac Oncol 3: S143-S145, "First-generation epidermal growth factor receptor tyrosine kinase inhibitors in EGFR mutation: positive non-small cell lung cancer patients" abstract.
Several mutations that abolish PI3-K activity have been described and are catalogued in the human protein mutation database MutDB (http://mutdb.org/) 1 page.
Shaw et al, (2006) Nature 441: 424-430, "Ras, PI(3)K and mTOR signalling controls tumour cell growth" abstract.
She et al. (2008) PLoS One 3: e3065, "Breast tumor cells with PI3K mutation or HER2 amplification are selectively addicted to Akt signaling" abstract.
Sherman et al. (2007) BMC Bioinformatics 8:426-436, "DAVID Knowledgebase: a gene-centered database integrating heterogeneous gene annotation resources to facilitate high-throughput gene functional analysis".
Shridhar et al. (1987) Indian journal of Chemistry 26B:596-598, "Synthesis & antiparasitic activity of some new 1-(6/7-Nitrobenzoxazin-3-yl)-4-substituted-3-thiosemicarbazides & 4-Disubstituted 3-(6-Acetylbenzoxazin3-one)thiosemicarbazones".
Shtilbans et al. (2008) Ann Diagn Pathol 12: 153-160, "Current overview of the role of Akt in cancer studies via applied immunohistochemistry" abstract.
Siegel-Lakhai et al. (2005) Oncologist 10: 579-589, "Current knowledge and future directions of the selective epidermal growth factor receptor inhibitors erlotinib (Tarceva) and gefitinib (Iressa)" abstract.
Simone (1996) Cecil Textbook of Medicine, 20th Edition 1:1004-1010, "Part XIV Oncology: 154 Introduction".
Smakman et al. (2005) Biochim Biophys Acta 1756: 103-114, "Control of colorectal metastasis formation by K-Ras" abstract.
Spano et al. (2008) Crit Rev Oncol Hematol 66: 21-30, "Potential predictive markers of response to EGFR-targeted therapies in colorectal cancer" abstract.
Steelman et al. (2008) Leukemia 22: 686-707, "Contributions of e Raf/MEK/ERK, PI3K/PTEN/Akt/mTOR and Jak/STAT pathways to leukemia" abstract.
Steiner et al. (2007) Clin Cancer Res 13: 1540-1551, "Tumor growth inhibition with cetuximab and chemotherapy in non-small cell lung cancer xenografts expressing Wild-type and mutated epidermal growth factor receptor" abstract.
Stintzing et al. (2009) Dtsch Arztebllnt 106: 202-206, "The treatment of colorectal carcinoma with monoclonal antibodies: the importance of KRAS mutation analysis and EGFR status" abstract.
Strimpakos et al (2009) Cancer Treat Rev 35: 148-159, "The role of mTOR in the management of solid tumors: an overview" abstract.
Suda et al. (2009) J Thorac Oncol 4: 1-4, "N(4)-substituted isatin thiosemicarbazones and their copper(II) complexes" EGFR T790M mutation: a double role in lung cancer cell survival? abstract.
Sugimoto et al., "Activation of Dithiocarbamate by 2-Halothiazolium Salts", 1988, J. Org. Chem., 53, pp. 2263-2267.
Supplementary European Search Report for European Application No. 08865722 mailed Feb. 9, 2012.
Suzuki et al., Preparation of diphenylmethylimine derivatives as antiinflammatories, *antitumors, and lipoxygenase and cyclooxygenase inhibitors, 1987 (abstract).
Szakacs et al. (2006) Nature Reviews Drug Discovery 5:219-234, "Targeting multidrug resistance in cancer".
Szakacs et al. (2008) Drug Discovery Today 13(9/10):379-393, "The role of ABC transporters in drug absorption, distribution, metabolism, excretion and toxicity (ADME-Tox)".
Tang et al. (2006) Oncol Rep 15: 855-859, "PTEN sensitizes epidermal growth factor-mediated proliferation in endometrial carcinoma cells" abstract.
Teachey et al. (2009) Br J Haematol 145: 569-580, "Mammalian target of rapamycin inhibitors and their potential role in therapy in leukaemia and other haematological malignancies" abstract.
Testa et al. (2005) Oncogene 24: 7391-7393, "AKT signaling in normal and malignant cells" abstract.
The intersection of common genes was determined using Gene Venn (http://mcbc.usm.edu/genevenn/genevenn.htm) 1 page.
Tomida et al. (2005) Cancer Sci 96: 63-68, "Throwing new light on lung cancer pathogenesis: updates on three recent topics" abstract.
Tzeng et al, (2007) J Surg Res 143; 20-26, "EGFR genomic gain and aberrant pathway signaling in pancreatic cancer patients" abstract.
Undevia et al. (2005) Nature Reviews 5:447-458, "Pharmacokinetic variability of anticancer agents".
Uramoto et al. (2007) Br J Cancer 96: 857-863, "Which biomarker predicts benefit from EGFR-TKI treatment for patients with lung cancer?" abstract.
Van den Bongard et al. (2000) Clinical Pharmacokinetics 39(5):345-367, "Pharmacokinetically Guided Administration of Chemotherapeutic Agents" abstract.
Vanhaesebroeck et al. (2000) Biochem J 346 Pt 3: 561-576, "The PI3K-PDK1 connection: more than just a road to PKB" abstract.
Varughese et al. (1984) Drugs under Experimental and Clinical Research 10(2), 67-7-4, "A Biodistribution Study of 1-$^{14}$C-1,2-Cyclohexanedione Bis(4-Diethylenoxythiosemicarbazone ), A Potential Antitumour Agent".
Venkatakrishnan et al. (2001) J Clin Pliarmacol 41: 1149-1179. "Human drug metabolism andthe cytochromes P450: application and relevance of in vitro models".
Vippagunta et al (2001).
Vivanco et al. (2002) Nat Rev Cancer 2: 489-501, "The phosphatidylinositol 3-Kinase AKT pathway in human cancer" abstract.
Walther et al, (2009) Nat Rev Cancer 9: 489-499, "Genetic prognostic and predictive markers in colorectal cancer" abstract.
Wang et al. (2008) Cancer Res 68: 7409-7418, "Enhancing mammalian target of rapamycin (mTOR)-targeted cancer therapy by preventing mTOR/raptor inhibition-initiated, mTOR/rictor-independent Akt activation" abstract.
Wang et al., "Preparation of heteroaryl substituted hydrazinecarbothioamide compounds for treatment of cancer", 2007 (abstract).
Weng et al. (2009) Cancer Lett 273: 257-265, "Implication of the Akt2/survivin pathway as a critical target in paclitaxel treatment in human ovarian cancer cells" abstract.
West et al., "Copper(II) complexes of 2-formyl-, 6-methyl-2-formyl- and 2-benzoylpyridine N(4)-(2-methylpyridinyl)-,N (4)-(2-ethylpyridinyl)-and N(4)-methyl(2-ethylpyridinyl) thiosemicarbazones", 1996, Transition Met. Chem., 21, pp. 289-295.
West et al., "Copper(II) complexes of 2-formyl-, 2-acetyl- and 2-benzoylpyridine N(4)-o-, N(4)-m-, N(4)-p-chlorophenylthiosenticarbazones", 1996, Transition Met. Chem., 21, pp. 52-57.
West et al., "Copper(II) complexes of 2-formyl-, 2-acetyl- and 2-benzoy-pyridine N(4)-phenyl-, N(4)-o-methoxyphenyl-, N(4)-p-methoxy-phenyl- and N(4)-p-nitrophenylthiosemicarbazones", 1996, Transition Met. Chem., 211, pp. 213-218.
Winkelmann et al. (1987) Drug Res 37(1):647-661, "Antimalarial and Anticoccidial Activity of 3-Aryl-7-chloro-3,4-dihydroacridine-1 ,9-(2H, 1OH)-diones".
Wolber et al. (2006) Methods in Enzymology 410:28-57, "the agilent in situ-synthesized in microarray platform".
Wong, KK (2008) Lung Cancer 60 Suppl 2: S10-S18, "Searching for a magic bullet in NSCLC: the role of epidermal growth factor receptor mutations and tyrosine kinase inhibitors".
Yamamoto et al. (2008) Cancer Res 68: 6913-6921, "PIK3CA mutations and copy number gains in human lung cancers" abstract.

(56) References Cited

OTHER PUBLICATIONS

Yang et al. (2002) Nat Struct Biol 9. 940-944, "Crystal structure of an activated Akt/protein kinase B ternary complex with GSK3-peptide and AMP-PNP" abstract.
Yap et al. (2008) Curr Opin Pharmacol 8: 393-412, "Targeting the PI3K-AKT-mTOR pathway: progress, pitfalls, and promises" abstract.
Yuan et al. (2000) Oncogene 19: 2324-2330, "Frequent activation of AKT2 and induction of apoptosis Dy inhibition of phosphoinositide-3-0H kinase/Akt pathway in human ovarian cancer" abstract.
Yuan et al. (2004) Blood 104:1450-1458, "Novel di-2-pyridyl-derived iron chelators with marked and selective antitumor activity: in vitro and in vivo assessment".
Zhang et al. (2005) Proc Natl Acad Sci U S A 102: 14605-14610, "Identification of K-ras as the major regulator for cytokine-dependent Akt activation in erythroid progenitors in vivo" abstract.
Zhang et al, (2007) J Med Genet 44: 166-172, "Somatic mutations of the epidermal growth factor receptor and non-small-cell lung cancer" abstract.
Zhang et al. (2007) Nat Med 13: 1114-1119, "Molecular imaging of Akt kinase activity" abstract.
Zhou (2008) Xenobiotica 38(7-8):802-832, "Structure, function and regulation of P-glycoprotein and its clinical relevance in drug disposition".
Zwick et al (2002) Trends in Molec Medicine 8(1): 17-23, "Receptor tyrosine kinases as targets for anticancer drugs" abstract.
J. Easmon et al., 39 Arzneimittel-Forschung, 1196-1201 (1989).
F.A. French et al. 17 Journal of Medicinal Chemistry, vol. 17, No. 2, 172-181 (1974).
N. F. Smith et al., Molecular Cancer Therapeutics, 6, 428-440 (2007).
B.A. Chabner et al., Chemotherapy of Neoplastic Diseases, Neoplastic Agents in, Goodman & Oilman's: The Pharmacological Basis of Therapeutics 1315-1403, 1315 (L. L. Brunton et al., eds. 11th ed. 2006).
R. Merriman et al., 49 Cancer Research 4509-4516, 4510, col. 1(1989).
Corrigan, Salt Forms, 3477-3487 (2007).
LC. Anderson et al., 56 Cancer Research, 715-718 (1996).
R.L. Merriman et al., 40 Cancer Research, 4509-4516, 4514, col. 2(1989).
M. Traynor et al., "Drugs of Today", 40(8), 697-710, 698 (2004)

S. Cannistra et al., Ovarian Cancer, Fallopian Tube Carcinoma and Peritoneal Carcinoma in, 2 Cancer Principles & Practice of Oncology 1568 (V.T. DeVita, Jr. et al. eds., 8th ed., 2008).
M. Kobel etal., PLoS Medicine, 5 (12) 1749-1760, 1749 (2008).
A.J. Tiltman, Best Practice & Research Clinical Obstretics & Gynaecology, 485-500, 19(4) (2005).
J. L. Razier, Journal of Neuro-Oncology, 74(1), 77-86. (2005).
R.G.W. Verhaak et al., Cancer Cell 17(1), 1-24 (2010).
K. Libutti, Colon Cancer in, 1Cancer Principles & Practice of Oncology 1232, 1243 (V.T. DeVita, Jr. et al. eds., 8th ed., 2008).
L. Pusztai, Histopathologic and Molecular Markers of Prognosis and Response to Therapy, in Breast Therapy, 324, 326-328 (Kelly K. Hunt et al., ed., 2nd ed., 2008).
D. Scheinberg et al., Management of Acute Luekemias, in 2 Cancer Principles & Practice of Oncology, 2008-2120 (V.T. DeVita, Jr. et al. eds., 7th ed., 2005).
D. Druker et al., Chronic Myelogenous Leukemia, in 2 Cancer Pinciples & Practice of Oncology, 2121 (V. T. DeVita, Jr. et al. eds., 7th ed. 2005).
S. O'Brien et al., Chronic Lymphoid Leukemias, in 2 Cancer Principles & Practice of Oncology, 2133-2143 (V.T. DeVita, Jr. et al. eds., 7th ed.. 2005).
S. Fader! et al., Myelodysplastic Syndromes, in 2 Cancer Principles & Practices of Oncology 2144-2154 (V.T. DeVita, Jr. et al. eds., 7th ed., 2005).
F.F. De Arruda, et al., Int. J. Radiation Oncology Bioi. Physc., 64(2) 363-373 (2006).
C. Bastian, Genetic Progression, in From Melanocytesto Melanoma the Progression to Malignancy 197, 201 (VJ. Hearing et al, eds, 2006).
T. Carling et al., Thyroid Tumors in, 2 Cancer Principles & Practice of Oncology 1503 (V.T. DeVita, Jr. et al., eds., 8th eds, 2008).
A.J. Rustgi, Molecular Biology of the Esophagus and Stomach, in 1Cancer Principles of Practice of Oncology 989-993, 991 (V.T. DeVita Jr. et al. eds., 8th eds., 2008).
K. Odunsi et al, Molecular Biology of Gynecological Cancers, in 2 Cancer Principles & Practice of Onocolgy 1487, 1492 (V.T. DeVita Jr. et al. eds., 8th eds., 2008).
C. Abad-Zapatero. Drug Discovery Today, 1-8 (2010).
Y. Song et al.. Cancer a Conceptual Framerwork in, 1 Cancer Principles & Practice of Oncology 1, 5-6 (V.T. DeVita,Jr et al, eds., 8th ed., 2008).
K.P. Olive et al., Clinical Research 12, 5277-5287 (2006).
Tsai et al., 105 PNAS 3041-3046, 3041 (2008).
J.A. Montgomery et al., 20 Journal of Medicinal Chemistry, 291-295 (1977).

\* cited by examiner

COMPOUNDS AND METHOD FOR TREATMENT OF HIV

This application is a division of U.S. application Ser. No. 14/618,986 filed Feb. 10, 2015, now allowed, which is a division of U.S. application Ser. No. 13/638,597 filed May 7, 2013, now U.S. Pat. No. 8,987,272, which is a national phase filing under 35 U.S.C. §371 of International Application No. PCT/CA2011/000357 filed Apr. 1, 2011, which claims the benefit of provisional U.S. Application No. 61/320,223, filed Apr. 1, 2010.

FIELD OF THE INVENTION

The present invention relates generally to therapeutic compounds and compositions, as well as methods for treatment of HIV.

BACKGROUND OF THE INVENTION

Human immunodeficiency viruses (HIV) are lentiviruses from the family of retroviridae. Transmission is initiated by the passage of HIV across the mucosal barrier of sexual organs or placenta when exposed to infectious body fluids such as semen, vaginal secretions, or blood.

HIV, particularly the strains known as HIV type-1 (HIV-1) and type-2 (HIV-2) viruses, is the etiological agent of the complex disease that includes progressive destruction of the immune system AIDS (acquired immune deficiency syndrome) and degeneration of the central and peripheral nervous system. A common feature of retrovirus replication is the action of integrase, a viral enzyme that inserts the viral genome into the DNA of the mammal cell. Since integration is a vital step in retroviral replication, blocking it can halt further spread of the virus.

Toxicity or undesirable side effects of the common drugs for treating HIV infection, e.g., AZT or HIV protease inhibitors, are incompatible with their antiviral activity when used at an effective pharmaceutical concentration. Thus, there is still a need in the art for alternative compounds for treating HIV.

SUMMARY OF THE INVENTION

In an aspect, there is provided a compound of Formula I:

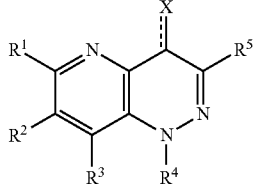

Formula I and/or a pharmaceutically-acceptable salt, hydrate, solvate, tautomer, optical isomer, E-isomer, Z-isomer, or combination thereof;

X is selected from Se, N—OH, NH, $NO_2$, CN, N—CN, N═O, O or S, wherein:

when X is Se, N—OH, NH, or N—CN, ⸺ is a double bond, and $R^1$, $R^2$, $R^3$, $R^4$ and $R^5$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

when X is selected from $NO_2$, CN or N═O, ⸺ is a single bond, and $R^1$, $R^2$, $R^3$, $R^4$ and $R^5$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and when X is O or S, ⸺ is a double bond, $R^1$, $R^2$, $R^3$, and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and $R^5$ is —(C═O)$NR^6R^7$ or

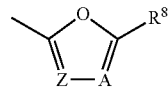

wherein $R^6$ and $R^7$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and wherein Z and A are each independently selected from $CR^9$ or N, and $R^8$ and $R^9$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another aspect, $R^1$, $R^2$, $R^3$, and $R^4$ are each independently selected from H, halo, hydroxyl, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, amino, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In a further aspect, $R^1$, $R^2$, $R^3$, and $R^4$ are each independently selected from H or substituted or unsubstituted alkyl. In another aspect, X is selected from Se, N—OH, NH, $NO_2$, CN, N—CN, or N═O; and $R^5$ is selected from H, a substituted or unsubstituted hydrocarbon group, a substituted or unsubstituted heterogeneous group, a substituted or unsubstituted aromatic group, or a substituted or unsubstituted heteroaromatic group. In yet another aspect, $R^5$ is —(C═O)Y and Y is selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. In still another aspect, Y is selected from H, a substituted or unsubstituted hydrocarbon group, a substituted or unsubstituted heterogeneous group, a substituted or unsubstituted aromatic group, or a substituted or unsubstituted heteroaromatic group. In another aspect, the —(C═O)Y is —(C═O)NR$^6$R$^7$ and R$^6$ and R$^7$ are each independently selected from H or the substituted or unsubstituted hydrocarbon group. In another aspect, the substituted or unsubstituted hydrocarbon group is selected from a substituted or unsubstituted alkyl group. In another aspect, the substituted or unsubstituted alkyl group is a substituted or unsubstituted alkylaryl or a substituted or unsubstituted alkylheteroaryl. In another aspect, the substituted or unsubstituted alkylaryl is a substituted or unsubstituted alkylphenyl, wherein the phenyl group is substituted with a halo group.

In a further aspect, R$^5$ is —(C═O)OR$^6$ and R$^6$ is selected from H or a substituted or unsubstituted hydrocarbon group. In another aspect, R$^6$ is selected from a substituted or unsubstituted alkyl group. In yet another aspect, R$^6$ is H. In another aspect, R$^1$, R$^2$, R$^3$, and R$^4$ are each independently selected from a substituted or unsubstituted alkylaryl. In another aspect, the substituted or unsubstituted alkylaryl is a substituted or unsubstituted alkylphenyl, wherein the phenyl group is substituted with a halo group. In another aspect, the compound is selected from:

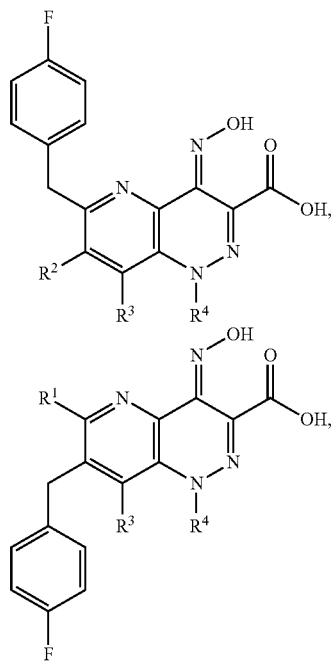

and/or a pharmaceutically-acceptable salt, hydrate, solvate, tautomer, optical isomer, E-isomer, Z-isomer, or combination thereof.

In another aspect, X is selected from Se, N—OH, NH, or N═O. In another aspect, X is O or S; and R$^6$ and R$^7$ are each independently selected from H or the substituted or unsubstituted hydrocarbon group. In another aspect, the substituted or unsubstituted hydrocarbon group is selected from a substituted or unsubstituted alkyl group. In yet another aspect, the substituted or unsubstituted alkyl group is a substituted or unsubstituted alkylaryl or a substituted or unsubstituted alkylheteroaryl. In another aspect, the substituted or unsubstituted alkylaryl is a substituted or unsubstituted alkylphenyl, wherein the phenyl group is substituted with a halo group. In another aspect, the halo group is selected from bromo, chloro, fluoro or iodo.

In another aspect, the compound is selected from:

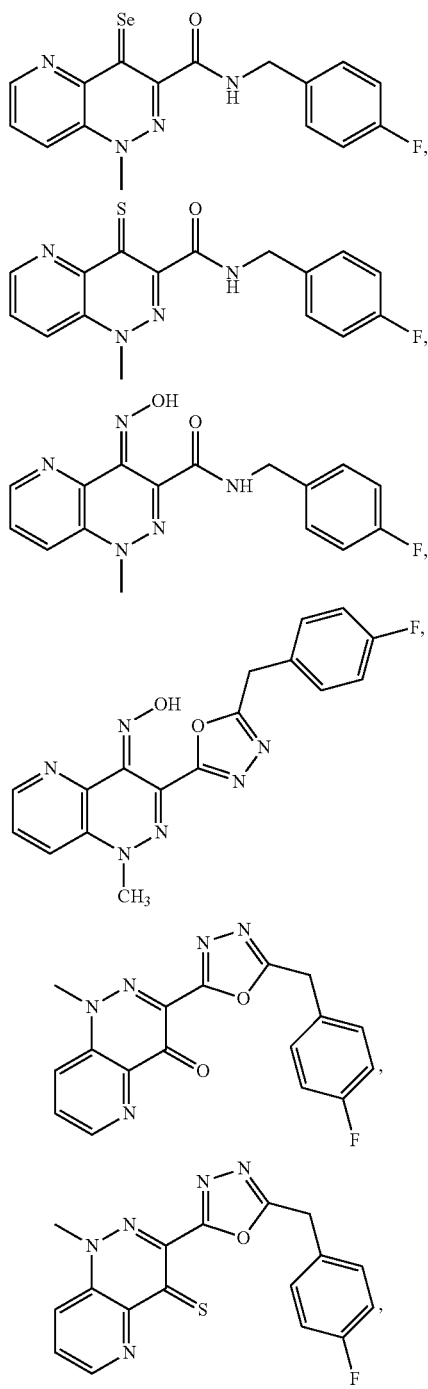

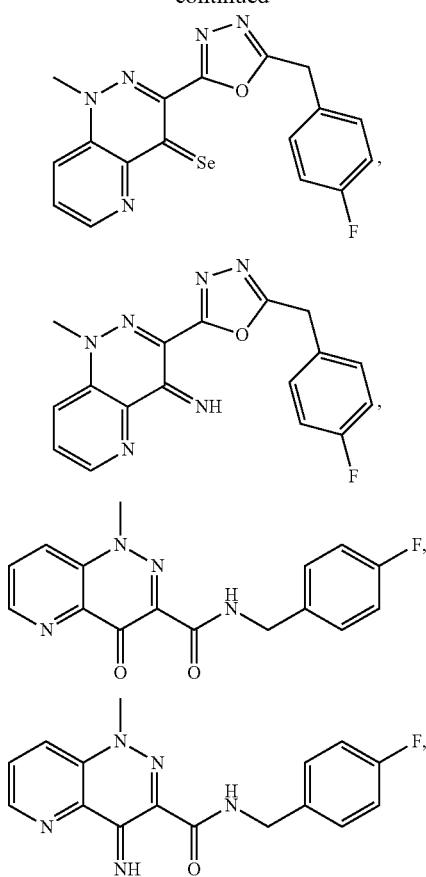

and/or a pharmaceutically-acceptable salt, hydrate, solvate, tautomer, optical isomer, E-isomer, Z-isomer, or combination thereof.

In another aspect, X is selected from Se, N—OH, NH, or N—CN; and $R^5$ is selected from H, a substituted or unsubstituted hydrocarbon group, a substituted or unsubstituted heterogeneous group, a substituted or unsubstituted aromatic group, or a substituted or unsubstituted heteroaromatic group. In another aspect, $R^5$ is selected from a substituted or unsubstituted aromatic group, or a substituted or unsubstituted heteroaromatic group. In another aspect, $R^5$ is a substituted or unsubstituted heteroaromatic group. In another aspect, $R^5$ is

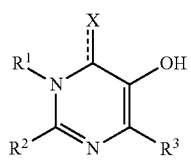

wherein Z and A are each independently selected from $CR^9$ or N, and $R^8$ and $R^9$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. In another aspect, X is O or S and $R^5$ is the

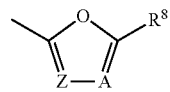

wherein Z and A are each independently selected from $CR^9$ or N, and $R^8$ and $R^9$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. In yet another aspect, at least one of Z and A is N. In another aspect, both Z and A are N. In another aspect, $R^8$ is a substituted or unsubstituted hydrocarbon group. In another aspect, $R^8$ is selected from a substituted or unsubstituted alkyl group. In another aspect, the substituted or unsubstituted alkyl group is a substituted or unsubstituted alkylaryl or a substituted or unsubstituted alkylheteroaryl. In another aspect, the substituted or unsubstituted alkylaryl is a substituted or unsubstituted alkylphenyl, wherein the phenyl group is substituted with a halo group. In another aspect, the halo group is selected from bromo, chloro, fluoro or iodo.

In yet another aspect, the compound is selected from:

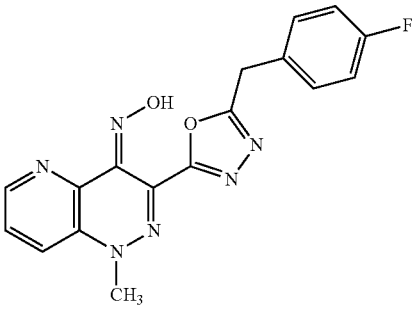

and/or a pharmaceutically-acceptable salt, hydrate, solvate, tautomer, optical isomer, E-isomer, Z-isomer, or combination thereof.

In still another aspect, there is provided a compound of Formula II:

Formula II and/or a pharmaceutically-acceptable salt, hydrate, solvate, tautomer, optical isomer, E-isomer, Z-isomer, or combination thereof;

X is selected from Se, N—OH, NH, $NO_2$, CN, N—CN, N=O, O or S, wherein:
when X is Se, N—OH, NH, N—CN, or S, ----- is a double bond, and
$R^1$, $R^2$, and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

when X is selected from $NO_2$, CN or N=O, ⋯ is a single bond, and $R^1$, $R^2$, and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and when X is O, ⋯ is a double bond, $R^1$ and $R^2$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and $R^3$ is

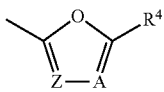

wherein Z and A are each independently selected from $CR^{10}$ or N, and $R^4$ and $R^{10}$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another aspect, $R^1$ and $R^2$ are each independently selected from H, halo, hydroxyl, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, amino, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl. In yet another aspect, $R^1$ and $R^2$ are each independently selected from H or substituted or unsubstituted alkyl. In another aspect, X is selected from Se, N—OH, NH, $NO_2$, CN, N—CN, N=O, or S; and $R^3$ is selected from H, a substituted or unsubstituted hydrocarbon group, a substituted or unsubstituted heterogeneous group, a substituted or unsubstituted aromatic group, or a substituted or unsubstituted heteroaromatic group. In another aspect, $R^3$ is selected from a substituted or unsubstituted aromatic group, or a substituted or unsubstituted heteroaromatic group. In another aspect, $R^3$ is a substituted or unsubstituted heteroaromatic group. In still another aspect, $R^3$ is

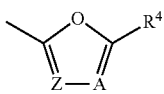

wherein Z and A are each independently selected from $CR^{10}$ or N, and $R^4$ and $R^{10}$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. In another aspect, X is O. In another aspect, at least one of Z and A is N. In another aspect, both Z and A are N. In another aspect, $R^4$ is a substituted or unsubstituted hydrocarbon group. In another aspect, $R^4$ is selected from a substituted or unsubstituted alkyl group. In another aspect, the substituted or unsubstituted alkyl group is a substituted or unsubstituted alkylaryl or a substituted or unsubstituted alkylheteroaryl. In another aspect, the substituted or unsubstituted alkylaryl is a substituted or unsubstituted alkylphenyl, wherein the phenyl group is substituted with a halo group. In another aspect, the halo group is selected from bromo, chloro, fluoro or iodo. In another aspect, X is selected from Se, N—OH, NH, N—CN, or S; and $R^3$ is selected from H, a substituted or unsubstituted hydrocarbon group, a substituted or unsubstituted heterogeneous group, a substituted or unsubstituted aromatic group, or a substituted or unsubstituted heteroaromatic group. In another aspect, $R^3$ is —(C=O)Y and Y is selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. In still another aspect, Y is selected from H, a substituted or unsubstituted hydrocarbon group, a substituted or unsubstituted heterogeneous group, a substituted or unsubstituted aromatic group, or a substituted or unsubstituted heteroaromatic group. In another aspect, the —(C=O)Y is —(C=O)$NR^8R^9$ and $R^8$ and $R^9$ are each independently selected from H or the substituted or unsubstituted hydrocarbon group. In another aspect, the substituted or unsubstituted hydrocarbon group is selected from a substituted or unsubstituted alkyl group. In another aspect, the substituted or unsubstituted alkyl group is a substituted or unsubstituted alkylaryl or a substituted or unsubstituted alkylheteroaryl. In another aspect, the substituted or unsubstituted alkylaryl is a substituted or unsubstituted alkylphenyl, wherein the phenyl group is substituted with a halo group. In another aspect, the compound is selected from:

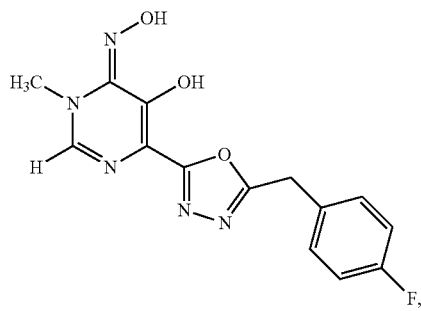

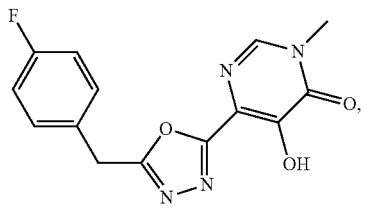

-continued

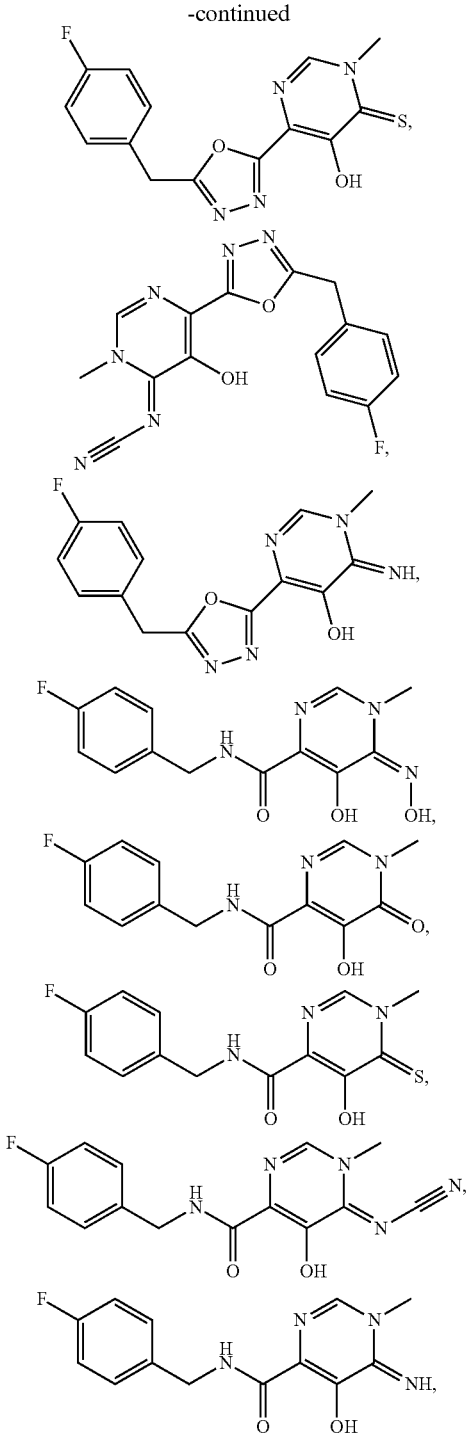

and/or a pharmaceutically-acceptable salt, hydrate, solvate, tautomer, optical isomer, E-isomer, Z-isomer, or combination thereof.

In another aspect, wherein the compound above is an HIV integrase inhibitor.

In another aspect, there is provided a pharmaceutical composition comprising the compound above, and/or a pharmaceutically-acceptable salt, hydrate, solvate, tautomer, optical isomer, E-isomer, Z-isomer, or combination thereof, optionally with a pharmaceutically acceptable carrier or diluent. In another aspect, there is provided the pharmaceutical composition in combination with at least one other anti-HIV agent.

In another aspect, there is provided a method for the treatment of HIV in a mammal comprising administering to said mammal an anti-HIV effective treatment amount of the compound above, and/or a pharmaceutically-acceptable salt, hydrate, solvate, tautomer, optical isomer, E-isomer, Z-isomer, or combination thereof, optionally with a pharmaceutically acceptable carrier or diluent.

In another aspect, there is provided a method for salvage therapy in the treatment of HIV in a mammal comprising administering to said mammal an anti-HIV effective treatment amount of a compound above, and/or a pharmaceutically-acceptable salt, hydrate, solvate, tautomer, optical isomer, E-isomer, Z-isomer, or combination thereof, optionally with a pharmaceutically acceptable carrier or diluent. In another aspect, the mammal is human. In another aspect, the method further comprises co-administering at least one other anti-HIV agent in combination and/or in alternation with the compound.

In yet another aspect, there is provided a use of an anti-HIV effective treatment amount of the compound above, and/or a pharmaceutically-acceptable salt, hydrate, solvate, tautomer, optical isomer, E-isomer, Z-isomer, or combination thereof, optionally with a pharmaceutically acceptable carrier or diluent, in the manufacture of a medicament for the treatment of HIV in a mammal.

In another aspect, there is provided a use of an anti-HIV effective treatment amount of the compound above, and/or a pharmaceutically-acceptable salt, hydrate, solvate, tautomer, optical isomer, E-isomer, Z-isomer, or combination thereof, optionally with a pharmaceutically acceptable carrier or diluent, in the manufacture of a medicament for salvage therapy in the treatment of HIV in a mammal.

In another aspect, there is provided a use of an anti-HIV effective treatment amount of the compound above, and/or a pharmaceutically-acceptable salt, hydrate, solvate, tautomer, optical isomer, E-isomer, Z-isomer, or combination thereof, optionally with a pharmaceutically acceptable carrier or diluent, for the treatment of HIV in a mammal.

In another aspect, there is provided a use of an anti-HIV effective treatment amount of the compound above, and/or a pharmaceutically-acceptable salt, hydrate, solvate, tautomer, optical isomer, E-isomer, Z-isomer, or combination thereof, optionally with a pharmaceutically acceptable carrier or diluent, for salvage therapy in the treatment of HIV in a mammal.

In another aspect, the mammal is human. In another aspect, the use further comprises use of at least one other anti-HIV agent in combination and/or in alternation with the compound.

In yet another aspect, there is provided a method for making the compound of Formula III:

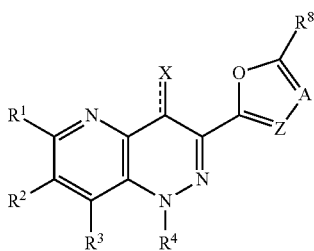

Formula III and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N=O, O or S, wherein:

when X is selected from Se, N—OH, NH, N—CN, O or S, ---- is a double bond, when X is selected from NO$_2$, CN or N=O, ---- is a single bond, R$^1$, R$^2$, R$^3$, and R$^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and Z and A are each independently selected from CR$^9$ or N, and R$^8$ and R$^9$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein the method comprises:

a) reacting a compound of Formula VII with an amine of NH$_2$AHC(O)R$^8$ to form an intermediate of Formula VIII:

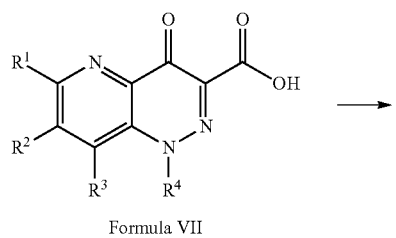

Formula VII

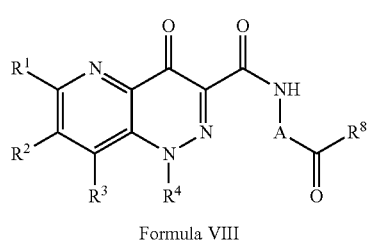

Formula VIII b) reacting the intermediate of Formula VIII with base to yield Formula III, whereby X is oxygen;

c) reacting Formula III, whereby X is oxygen, under conditions to replace the oxygen of the carbonyl group with any X group defined herein to form the compounds of Formula III. In yet another aspect, wherein c) comprises reacting Formula III, whereby X is oxygen, with NH$_2$OH to form the compound of Formula III, wherein X is N—OH.

In another aspect, there is provided a method for making the compound of Formula IV:

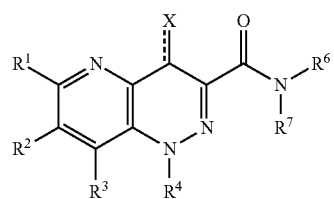

Formula IV and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N=O, O or S, wherein:

when X is Se, N—OH, NH, or N—CN, ---- is a double bond, when X is selected from NO$_2$, CN or N=O, ---- is a single bond, when X is O or S, ---- is a double bond, R$^1$, R$^2$, R$^3$, and R$^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and wherein R$^6$ and R$^7$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein the method comprises:

a) reacting a compound of Formula VII with an amine of NHR$^6$R$^7$ to form an intermediate of Formula IX:

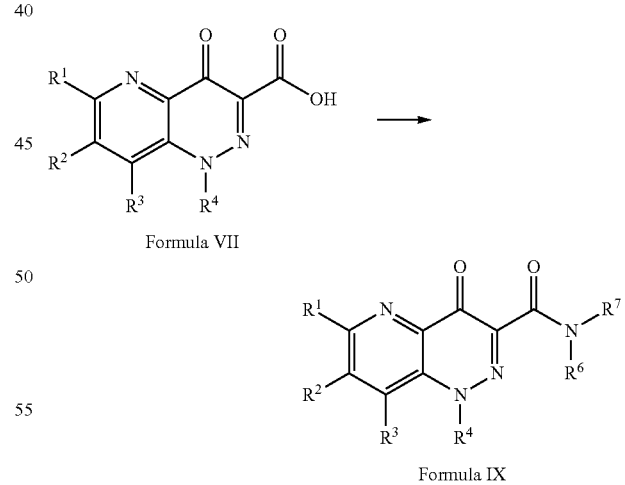

Formula VII

Formula IX b) reacting the intermediate of Formula IX under conditions to replace the oxygen of the carbonyl group in the ring with any X group defined herein to form the compound of Formula IV. In another aspect, wherein b) comprises reacting Formula IX with NH$_2$OH to form the compound of Formula IV, wherein X is N—OH.

In yet another aspect, there is provided a method for making the compound of Formula V:

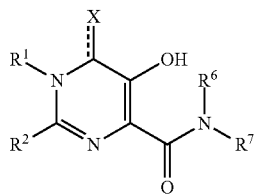

Formula V and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N═O, O or S, wherein:

when X is Se, N—OH, NH, N—CN, or S, ▬▬▬ is a double bond, and when X is selected from NO$_2$, CN or N═O, ▬▬▬ is a single bond, R$^1$ and R$^2$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and wherein R$^6$ and R$^7$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein the method comprises:

a) reacting a compound of Formula XII with an amine of NHR$^6$R$^7$ to form an intermediate of Formula XIII:

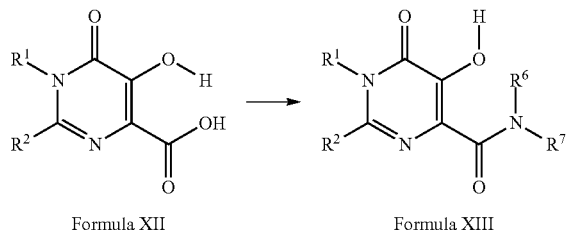

Formula XII        Formula XIII b) reacting the intermediate of Formula XIII under conditions to replace the oxygen of the carbonyl group in the ring with any X group defined herein to form the compound of Formula V. In yet another aspect, wherein b) comprises reacting Formula XIII with NH$_2$OH to form the compound of Formula V, wherein X is N—OH.

In another aspect, there is provided a method for making the compound of Formula VI:

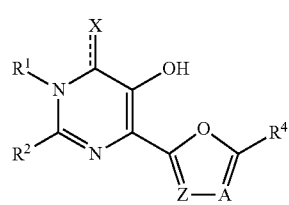

Formula VI and/or a pharmaceutically-acceptable salt, hydrate, solvate, tautomer, optical isomer, E-isomer, Z-isomer, or combination thereof;

X is N—OH and ▬▬▬ is a double bond,

R$^1$ and R$^2$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and wherein Z and A are each independently selected from CR$^{10}$ or N, and R$^4$ and R$^{10}$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein the method comprises:

a) reacting a compound of Formula X, whereby R is a benzyl group, with an amine of NH$_2$AHC(O)R$^4$ to form an intermediate of Formula XI:

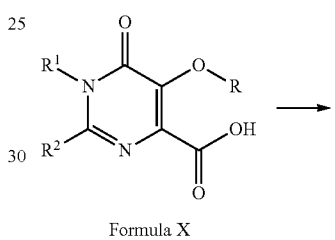

Formula X

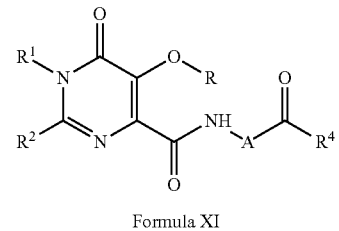

Formula XI b) reacting the intermediate of Formula XI with base to yield Formula VI, whereby X is oxygen;

c) reacting Formula VI, whereby X is oxygen, with Lawesson's reagent, to yield Formula VI, whereby X is sulfur;

d) reacting Formula VI, whereby X is sulfur and R is a benzyl group, with NH$_2$OCH$_2$Ar, to yield Formula VI, whereby X is N—O—CH$_2$Ar; and e) reducing Formula VI, whereby X is N—O—CH$_2$Ar, to yield Formula VI, whereby X is N—OH and R is a H.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Certain embodiments of the present invention will now be described more fully with reference to the accompanying drawings.

DETAILED DESCRIPTION

Figure 1:
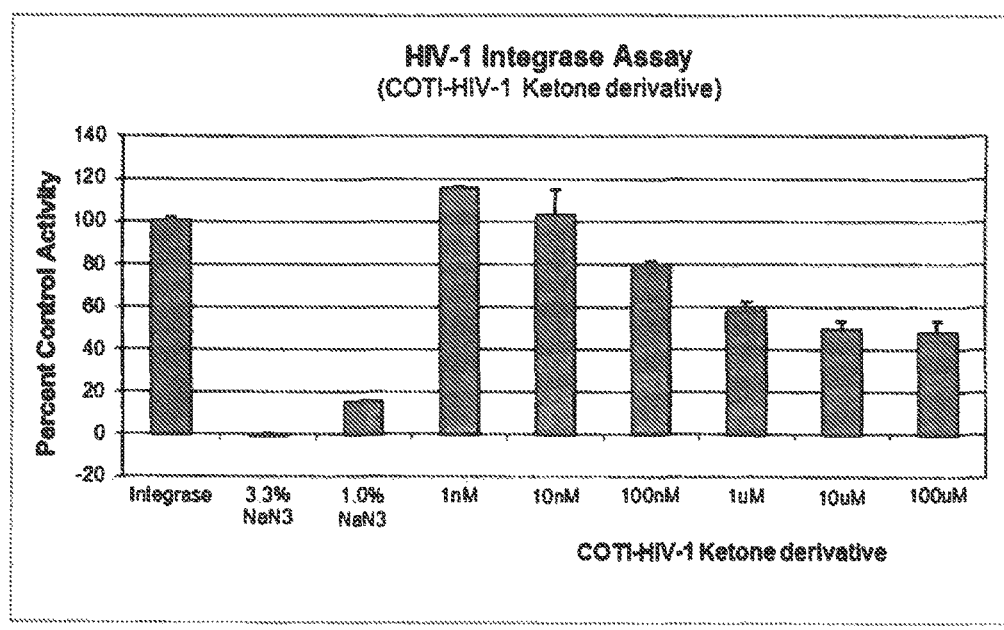
FIG. 1 shows a graph of the effect of COTI-HIV1Doxo in an HIV-1 integrase assay.

The present invention is directed to new compounds, compositions comprising such compounds, a method of administration thereof, and use thereof to treat HIV. The compounds of this invention may function as inhibitors of HIV integrase.

DEFINITIONS

When describing the compounds, compositions, methods and uses of this invention, the following terms have the following meanings unless otherwise indicated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The compounds of the present invention may have asymmetric centers, chiral axes, and chiral planes (as described, for example, in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, E isomers, and Z isomers, being included in the present invention. In addition, the compounds disclosed herein may exist as tautomers and both tautomeric forms are intended to be encompassed by the scope of the invention, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are mono-haloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch.

Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C=O)—O—.

The term "carbonyl group", whether used alone or with other terms, such as "aminocarbonyl group", denotes —(C=O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N, N-dimethyl-aminoethyl, N, N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The present invention includes pharmaceutically acceptable salts, solvates and prodrugs of the compounds of the invention and mixtures thereof.

The terms "comprising", "having" and "including", and various endings thereof, are meant to be open ended, including the indicated component but not excluding other elements.

A compound of the invention is represented by a compound of Formula I:

Formula I

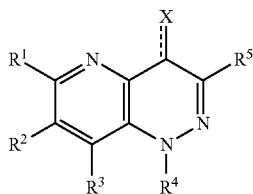

and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N=O, O or S, wherein:

when X is Se, N—OH, NH, or N—CN, ---- is a double bond, and $R^1$, $R^2$, $R^3$, $R^4$ and $R^5$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

when X is selected from NO$_2$, CN or N=O, ---- is a single bond, and $R^1$, $R^2$, $R^3$, $R^4$ and $R^5$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and when X is O or S, ---- is a double bond, $R^1$, $R^2$, $R^3$, and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and $R^5$ is —(C=O)NR$^6$R$^7$ or

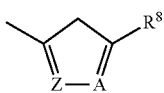

wherein $R^6$ and $R^7$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and wherein Z and A are each independently selected from CR$^9$ or N, and $R^8$ and $R^9$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

A compound of the invention is also represented by a compound of Formula II:

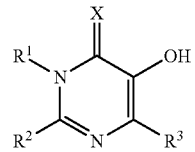

Formula II and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N=O, O or S, wherein:

when X is Se, N—OH, NH, N—CN, or S, ---- is a double bond, and $R^1$, $R^2$, and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

when X is selected from NO$_2$, CN or N=O, ---- is a single bond, and $R^1$, $R^2$, and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and when X is O, ---- is a double bond, $R^1$ and $R^2$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and $R^3$ is

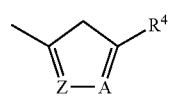

wherein Z and A are each independently selected from CR$^{10}$ or N, and $R^4$ and $R^{10}$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In one embodiment, there is provided a compound represented by a compound of Formula III:

Formula III

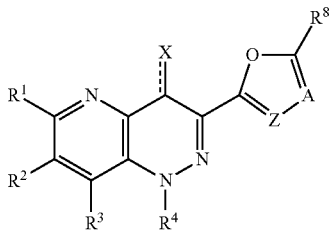

and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N═O, O or S, wherein:

when X is selected from Se, N—OH, NH, N—CN, O or S, ----- is a double bond, when X is selected from NO$_2$, CN or N═O, ----- is a single bond, $R^1$, $R^2$, $R^3$, and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and Z and A are each independently selected from $CR^9$ or N, and $R^8$ and $R^9$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, or a substituted or unsubstituted aromatic group, or a substituted or unsubstituted heteroaromatic group.

In another embodiment, both Z and A are N and $R^8$ is a substituted or unsubstituted hydrocarbon group. In a more specific embodiment, $R^8$ is selected from a substituted or unsubstituted alkyl group, such as a substituted or unsubstituted alkylaryl or a substituted or unsubstituted alkylheteroaryl. More specifically, the substituted or unsubstituted alkylaryl is a substituted or unsubstituted alkylphenyl, wherein the phenyl group is substituted with a halo group such as a 4-fluorobenzyl group. $R^1$, $R^2$, $R^3$, and $R^4$ may be specifically H or substituted or unsubstituted alkyl groups.

In a further embodiment, there is provided a compound represented by a compound of Formula IV:

Formula IV

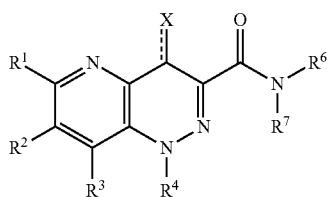

and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N═O, O or S, wherein:

when X is Se, N—OH, NH, or N—CN, ----- is a double bond, when X is selected from NO$_2$, CN or N═O, ----- is a single bond, when X is O or S, ----- is a double bond, $R^1$, $R^2$, $R^3$, and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and wherein $R^6$ and $R^7$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another embodiment, $R^6$ and $R^7$ are each independently selected from a substituted or unsubstituted alkyl group. The substituted or unsubstituted alkyl group may be a substituted or unsubstituted alkylaryl or a substituted or unsubstituted alkylheteroaryl. More specifically, the substituted or unsubstituted alkylaryl is a substituted or unsubstituted alkylphenyl, wherein the phenyl group is substituted with a halo group such as a 4-fluorobenzyl group. $R^1$, $R^2$, $R^3$, and $R^4$ may be specifically H or substituted or unsubstituted alkyl groups.

Specific embodiments include, without being limited thereto, compounds such as:

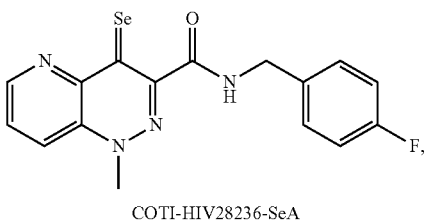

COTI-HIV28236-SeA

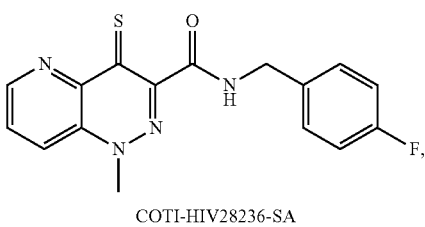

COTI-HIV28236-SA

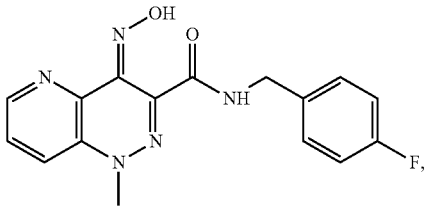

COTI-HIV28236

-continued

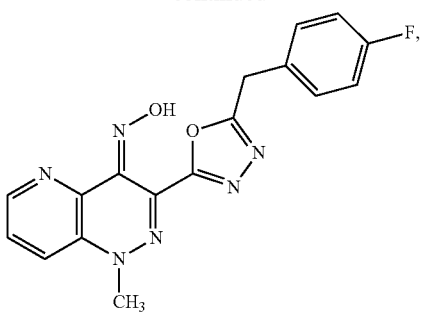

COTI-HIV28233 (COTI-HIV1oxime)

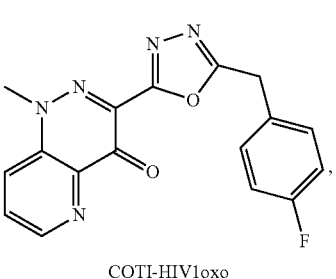

COTI-HIV1oxo

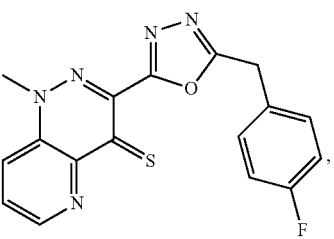

COTI-HIV1thio

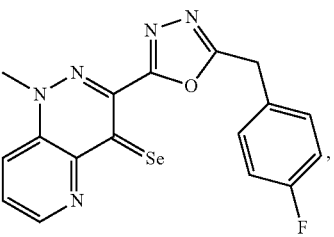

COTI-HIV1Se

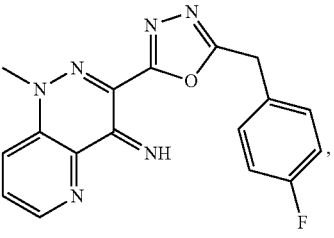

COTI-HIV1imine

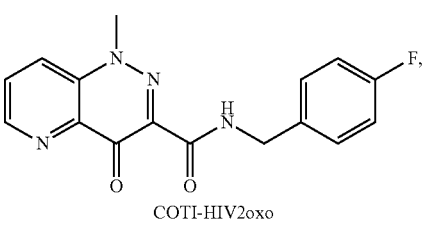

COTI-HIV2oxo

-continued

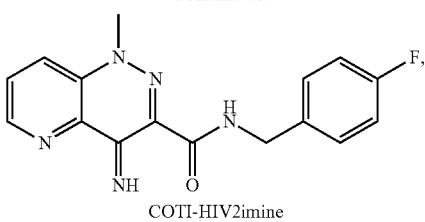

COTI-HIV2imine and/or a pharmaceutically-acceptable salt, hydrate, solvate, tautomer, optical isomer, E-isomer, Z-isomer, or combination thereof.

In a further embodiment, there is provided a compound represented by a compound of Formula IVA:

Formula IV

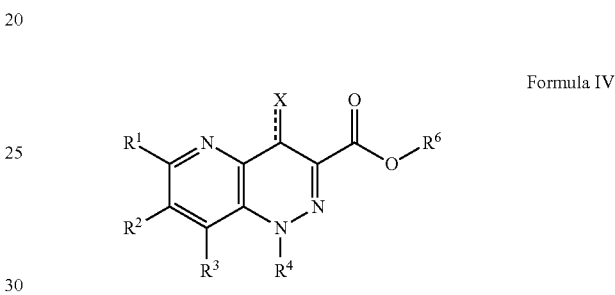

and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N=O, O or S, wherein:

when X is Se, N—OH, NH, or N—CN, ----- is a double bond, when X is selected from NO$_2$, CN or N=O, ----- is a single bond, when X is O or S, ----- is a double bond, $R^1$, $R^2$, $R^3$, and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and wherein $R^6$ is selected from H, halo, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another embodiment, $R^6$ is selected from a substituted or unsubstituted alkyl group. In yet another embodiment, $R^6$ is H. In another embodiment, $R^1$, $R^2$, $R^3$, and $R^4$ are each independently selected from a substituted or unsubstituted alkylaryl. In another embodiment, the substituted or unsubstituted alkylaryl is a substituted or unsubstituted alkylphenyl, wherein the phenyl group is substituted with a halo group.

In a further embodiment, the compound is selected from:

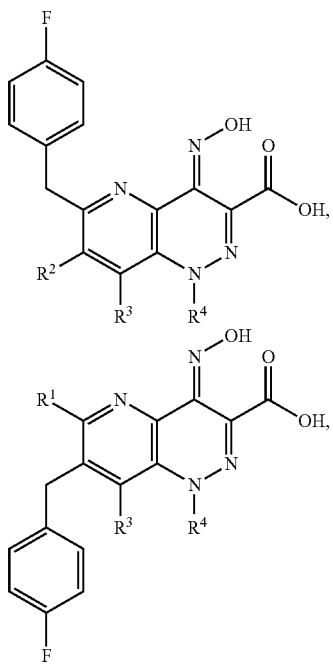

and/or a pharmaceutically-acceptable salt, hydrate, solvate, tautomer, optical isomer, E-isomer, Z-isomer, or combination thereof.

In yet another embodiment, there is provided a compound represented by a compound of Formula V:

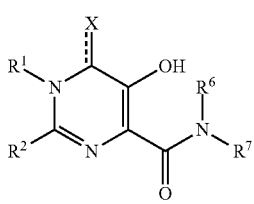

Formula V and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N=O, O or S, wherein:

when X is Se, N—OH, NH, N—CN, or S, ----- is a double bond, and when X is selected from NO$_2$, CN or N=O, ----- is a single bond, $R^1$ and $R^2$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and wherein $R^6$ and $R^7$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another embodiment, $R^6$ and $R^7$ are each independently selected from a substituted or unsubstituted alkyl group. The substituted or unsubstituted alkyl group may be a substituted or unsubstituted alkylaryl or a substituted or unsubstituted alkylheteroaryl. More specifically, the substituted or unsubstituted alkylaryl is a substituted or unsubstituted alkylphenyl, wherein the phenyl group is substituted with a halo group such as a 4-fluorobenzyl group. $R^1$ and $R^2$ may be specifically H or substituted or unsubstituted alkyl groups.

In another embodiment, there is provided a compound of Formula VI:

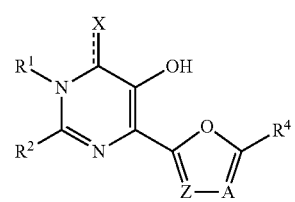

Formula VI and/or a pharmaceutically-acceptable salt, hydrate, solvate, tautomer, optical isomer, E-isomer, Z-isomer, or combination thereof;

X is selected from Se, N—OH, NH, NO$_2$, CN, N—CN, N=O, O or S, wherein:

when X is Se, N—OH, NH, N—CN, O or S, ----- is a double bond, when X is selected from NO$_2$, CN or N=O, ----- is a single bond, $R^1$ and $R^2$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and wherein Z and A are each independently selected from $CR^{10}$ or N, and $R^4$ and $R^{10}$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another embodiment, both Z and A are N and $R^4$ is a substituted or unsubstituted hydrocarbon group. In a more specific embodiment, $R^4$ is selected from a substituted or unsubstituted alkyl group, such as a substituted or unsubstituted alkylaryl or a substituted or unsubstituted alkylheteroaryl. More specifically, the substituted or unsubstituted alkylaryl is a substituted or unsubstituted alkylphenyl, wherein the phenyl group is substituted with a halo group such as a 4-fluorobenzyl group. $R^1$ and $R^2$ may be specifically H or substituted or unsubstituted alkyl groups.

Specific embodiments include, without being limited thereto, compounds such as:

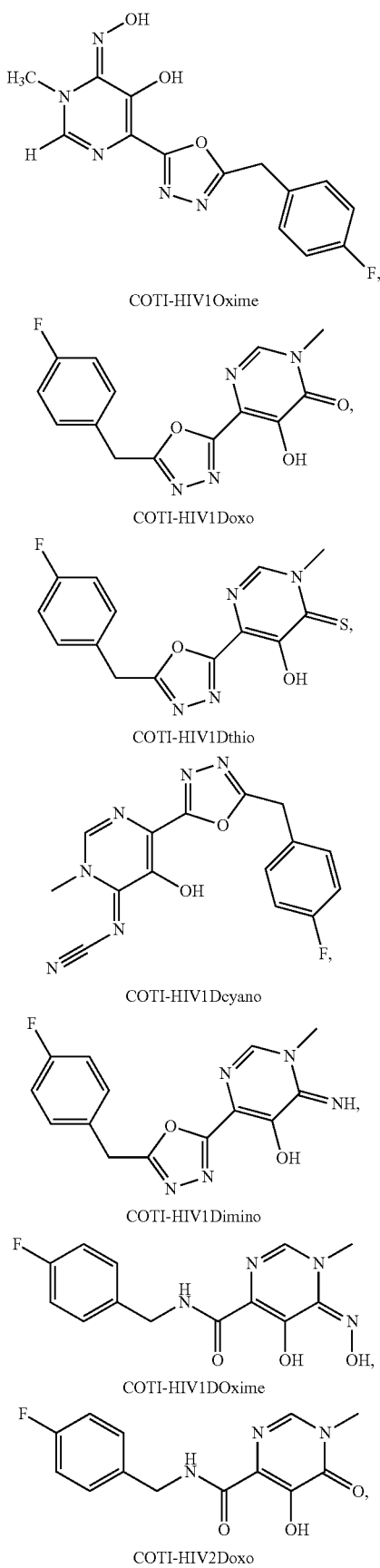

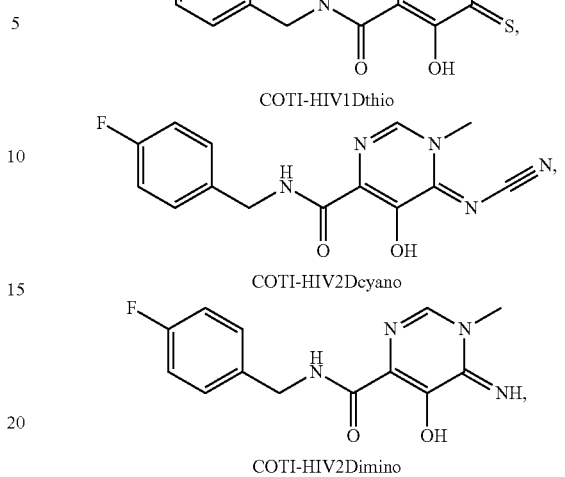

-continued and/or a pharmaceutically-acceptable salt, hydrate, solvate, tautomer, optical isomer, E-isomer, Z-isomer, or combination thereof.

The compounds of this invention may be prepared by employing reactions and standard manipulations that are known in the literature or exemplified herein.

The compounds of Formula III described herein can be prepared as follows:

a) reacting a compound of Formula VII with an amine of $NH_2AHC(O)R^8$ to form an intermediate of Formula VIII:

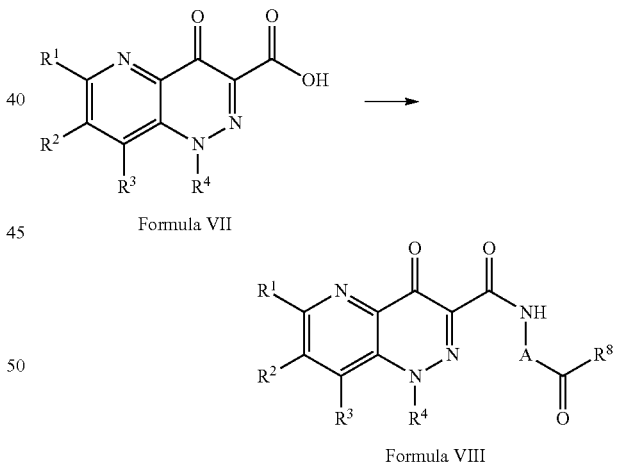

b) reacting the intermediate of Formula VIII with base to yield Formula III, whereby X is oxygen;

c) reacting Formula III, whereby X is oxygen, with $NH_2OH$ (or under conditions to replace the oxygen of the carbonyl group in the ring with any X group mentioned herein (e.g. Se, S, etc.)) to form the compounds of Formula III.

The compounds of Formula IV described herein can be prepared as follows:

a) reacting a compound of Formula VII with an amine of $NHR^6R^7$ to form an intermediate of Formula IX:

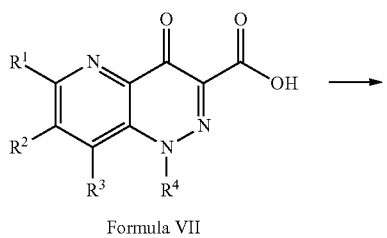

Formula VII

[Structure: Formula IX]

Formula IX b) reacting the intermediate of Formula IX with NH₂OH (or under conditions to replace the oxygen of the carbonyl group in the ring with any X group mentioned herein (e.g. Se, S, etc.)) to form the compound of Formula IV.

The compounds of Formula V described herein can be prepared as follows:

a) reacting a compound of Formula XII with an amine of NHR⁶R⁷ to form an intermediate of Formula XIII:

[Structures: Formula XII and Formula XIII]

Formula XII    Formula XIII b) reacting the intermediate of Formula XIII with NH₂OH (or under conditions to replace the oxygen of the carbonyl group in the ring with any X group mentioned herein (e.g. Se, S, etc.)) to form the compound of Formula V.

The compounds of Formula VI described herein can be prepared as follows:

a) reacting a compound of Formula X (R is a benzyl group) with an amine of NH₂AHC(O)R⁴ to form an intermediate of Formula XI:

[Structure: Formula X]

Formula X

[Structure: Formula XI]

Formula XI b) reacting the intermediate of Formula XI with base to yield Formula VI, whereby X is oxygen and R is a benzyl group;

c) reacting Formula VI, whereby X is oxygen and R is a benzyl group, with Lawesson's reagent, to yield Formula VI, whereby X is sulfur and R is a benzyl group;

d) reacting Formula VI, whereby X is sulfur and R is a benzyl group, with NH₂OCH₂Ar, to yield Formula VI, whereby X is N—O—CH₂Ar and R is a benzyl group; and e) reacting Formula VI, whereby X is N—O—CH₂Ar and R is a benzyl group, with H₂/Pd, to yield Formula VI, whereby X is N—O—H and R is a H.

The compounds of the present invention are useful in the treatment of HIV. Certain compounds of the present invention may exhibit reduced toxicity as compared with conventionally administered agents.

The methods and uses described herein can be specifically directed to inhibiting HIV integrase in a mammal in need thereof. Such methods and uses may prevent, treat or delay the onset of AIDS in a mammal in need thereof. The present invention also includes a compound of the present invention described herein, and/or a pharmaceutically-acceptable salt, hydrate, solvate, tautomer, optical isomer, E-isomer, Z-isomer, or combination thereof for use in, for use as a medicament for, and/or for use in the preparation of a medicament for: inhibiting HIV integrase, preventing or treating infection by HIV, or preventing, treating or delaying the onset of AIDS.

A composition can comprise the compound(s) of the present invention described herein, and/or a pharmaceutically-acceptable salt, hydrate, solvate, tautomer, optical isomer, E-isomer, Z-isomer, or combination thereof, optionally in combination with a pharmaceutically acceptable carrier or diluent. The compounds of this invention may be administered, for example, to mammals, typically humans, either alone or, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, and subcutaneous routes of administration.

The term "administration" (e.g., "administering" a compound) in reference to a compound of the invention means introducing the compound or a prodrug of the compound into the system of the mammal in need of treatment. For the purpose of inhibiting HIV integrase, preventing or treating HIV infection or preventing, treating or delaying the onset of AIDS, the compounds of the present invention can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in Remington's Pharmaceutical Sciences, 18th edition, edited by A. R. Gennaro, Mack Publishing Co., 1990.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the present invention may be used with one or more agents useful in the treatment of HIV infection or AIDS. As the compounds of the present invention can be HIV integrase inhibitors, such compounds are also useful in salvage therapy for patients whose virus has mutated and acquired resistance to other drugs. Such inhibitors target a distinct step in the retroviral life cycle and therefore, may be taken in combination with other types of HIV drugs to minimize adaptation by the virus.

For example, the compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or AIDS, such as those disclosed in Table 1 of International Patent Application No. WO 01/38332 or in the Table in International Patent Application WO 02/30930, incorporated herein by reference. Suitable HIV/AIDS antivirals for use in combination with the compounds of the present invention include, for example, HIV protease inhibitors (e.g., indinavir, atazanavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). It will be understood that the scope of combinations of the compounds of this invention with HIV/AIDS antivirals, immunomodulators, anti-infectives or vaccines is not limited to the foregoing substances or to the list in the above-referenced Tables, but includes in principle any combination with any pharmaceutical composition useful for the treatment of AIDS. The HIV/AIDS antivirals and other agents will typically be employed in these combinations in their conventional dosage ranges and regimens as reported in the art, including, for example, the dosages described in the Physicians' Desk Reference, 57th edition, Thomson PDR, 2003. The dosage ranges for a compound of the invention in these combinations are the same as those set forth above.

Other embodiments of the present invention include a pharmaceutical composition comprising an effective amount of a compound of the present invention described herein and a pharmaceutically acceptable carrier and/or diluent. The composition may further comprise an effective amount of an HIV infection/AIDS treatment agent selected from the group consisting of HIV/AIDS antiviral agents, immunomodulators, and anti-infective agents. The HIV infection/AIDS treatment agent is an antiviral selected from the group consisting of HIV protease inhibitors, non-nucleoside HIV reverse transcriptase inhibitors, and nucleoside HIV reverse transcriptase inhibitors. The HIV infection/AIDS treatment agent and the compound of the present invention can each be employed in an amount that renders the combination effective for inhibiting HIV integrase, for treating or preventing infection by HIV, or for preventing, treating or delaying the onset of AIDS.

Another embodiment includes a method for the treatment of HIV in a mammal comprising administering to the mammal an anti-HIV effective treatment amount of the compound of the present invention described herein, and/or a pharmaceutically-acceptable salt, hydrate, solvate, tautomer, optical isomer, E-isomer, Z-isomer, or combination thereof, optionally with a pharmaceutically acceptable carrier or diluent. There is also a method for salvage therapy in the treatment of HIV in a mammal comprising administering to said mammal an anti-HIV effective treatment amount of a compound of the present invention described herein, and/or a pharmaceutically-acceptable salt, hydrate, solvate, tautomer, optical isomer, E-isomer, Z-isomer, or combination thereof, optionally with a pharmaceutically acceptable carrier or diluent. The mammal is typically a human. If the compound of the present invention is co-administered with at least one other anti-HIV agent, this can be done in combination and/or in alternation with the compound.

In other embodiments, there is provided the use of an anti-HIV effective treatment amount of the compound of the present invention described herein, and/or a pharmaceutically-acceptable salt, hydrate, solvate, tautomer, optical isomer, E-isomer, Z-isomer, or combination thereof, optionally with a pharmaceutically acceptable carrier or diluent, in the manufacture of a medicament for the treatment of HIV in a mammal. There is also the use of an anti-HIV effective treatment amount of the compound of the present invention described herein, and/or a pharmaceutically-acceptable salt, hydrate, solvate, tautomer, optical isomer, E-isomer, Z-isomer, or combination thereof, optionally with a pharmaceutically acceptable carrier or diluent, in the manufacture of a medicament for salvage therapy in the treatment of HIV in a mammal.

In other embodiments, there is provided the use of an anti-HIV effective treatment amount of the compound of the present invention described herein, and/or a pharmaceutically-acceptable salt, hydrate, solvate, tautomer, optical isomer, E-isomer, Z-isomer, or combination thereof, optionally with a pharmaceutically acceptable carrier or diluent, for the treatment of HIV in a mammal. There is also the use of an anti-HIV effective treatment amount of the compound of the present invention described herein, and/or a pharmaceutically-acceptable salt, hydrate, solvate, tautomer, optical isomer, E-isomer, Z-isomer, or combination thereof, optionally with a pharmaceutically acceptable carrier or diluent, for salvage therapy in the treatment of HIV in a mammal.

With respect to the uses of the compound of the present invention described herein, and/or a pharmaceutically-acceptable salt, hydrate, solvate, tautomer, optical isomer, E-isomer, Z-isomer, or combination thereof, the mammal is typically a human. If the compound of the present invention described herein, and/or a pharmaceutically-acceptable salt, hydrate, solvate, tautomer, optical isomer, E-isomer, Z-isomer, or combination thereof is co-administered with at least one other anti-HIV agent, this can be done in combination and/or in alternation with the compound.

When introducing elements disclosed herein, the articles "a", "an", "the", and "said" are intended to mean that there are one or more of the elements.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Example 1

Synthesis of the compound of the following formula:

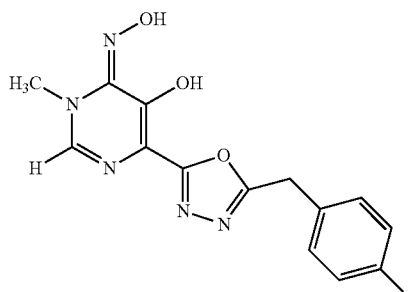

COTI-HIV1DOxime is as follows:
Synthesis of Starting Materials
Oxalic Acid Tert-Butyl Ester Methyl Ester

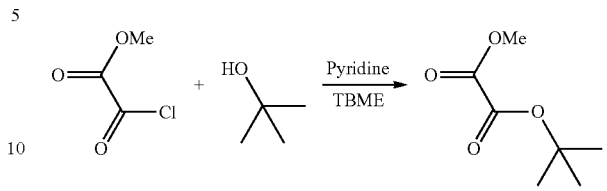

To a solution of methyl chlorooxoacetate in TBME (1 mmol/ml) was added at 0-5° C. tert-butanol (1.5 equiv.), followed by dropwise addition of pyridine (1.5 equiv.). The resulting mixture was stirred at room temperature for 20 h. Water (15 vol.) was added, the mixture was extracted with TBME twice. The combined organic extracts were washed with brine, dried over anhydrous $Na_2SO_4$ and concentrated under vacuum to give a colorless oil.
Synthesis of Oxalic Acid Tert-Butyl Ester Methyl Ester

| Starting material | Conditions | Isolated Product |
| --- | --- | --- |
| 1 g chlorooxoacetate | 1.5 eq. t-BuOH<br>1.5 eq. Pyridine<br>8 ml TBME<br>0° to rt 20 h | $^1$HNMR conforms |
| 20 g chlorooxoacetate | 1.5 eq. t-BuOH<br>1.5 eq. Pyridine<br>160 ml TBME<br>0° to rt 20 h | 22.7 g (87% yield)<br>$^1$HNMR conforms |
| 40 g chlorooxoacetate | 1.5 eq. t-BuOH<br>1.5 eq. Pyridine<br>8 ml TBME<br>0° to rt 20 h | 41.5 g (79.3% yield)<br>$^1$HNMR conforms |

Benzyloxy-Acetic Acid Methyl Ester
Benzyloxyacetyl chloride was added slowly to 10 vol of MeOH at 0-5° C. The mixture was stirred at room temperature for 20 h. MeOH was removed under vacuum to give quantitatively the desired product.

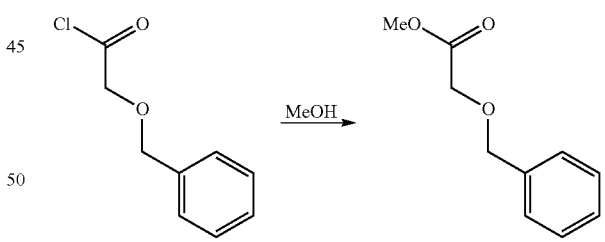

Synthesis of Benzyloxy-Acetic Acid Methyl Ester

| Starting material | Conditions | Isolated Product |
| --- | --- | --- |
| 1 g Benzyloxyacetyl chloride | 10 ml MeOH | 0.98 g (100%)<br>$^1$HNMR conforms |
| 20 g Benzyloxyacetyl chloride | 200 ml MeOH | 19.5 g (100% yield)<br>$^1$HNMR conforms |
| 25 g benzyloxyacetyl chlorid | 10 ml MeOH | 24.5 g (100%)<br>$^1$HNMR conforms |

Coupling of Oxalic Acid Tert-Butyl Ester Methyl Ester and Benzyloxyacetic Acid Methyl Ester

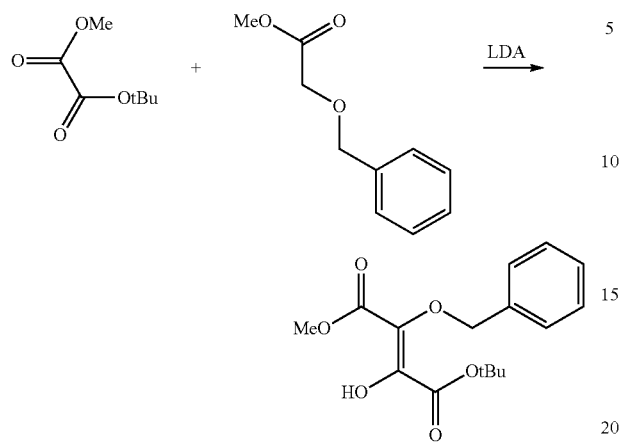

US2005/90668

Following the procedure described in U.S. Patent Publication No. 2005/0090668, a mixture of benzyloxy-acetic acid methyl ester (1 equiv.) and oxalic acid tert-butyl ester methyl ester (1.5 equiv.) in THF (12 vol.) was treated with 1.5 equiv. of LDA (prepared freshly from diisopropyl amine and n-BuLi in THF) at −78° C. for 1 h. The mixture was then warmed to room temperature for 1 h and quenched with cold HCl (1N, 11 vol.). The mixture was extracted with EtOAc (3×12 vol.), the organic extracts were washed with brine, dried over anhydrous $Na_2SO_4$ and concentrated to an oil. Chromatography of the crude product on silica gel (eluted with 15-60% EtOAc/Hexane) gave 78% of the coupled product as a colorless oil. As described in the patent, the $^1$HNMR is complex due to multiple enol tautomers and enol olefin configurations. TLC of the purified product showed a single spot. The results are summarized in the following table.

Coupling of Oxalic Acid Tert-Butyl Ester Methyl Ester and Benzyloxyacetic Acid Methyl Ester Synthesis of 5-Benzyloxy-6-oxo-1,6-dihydro-pyrimidine-4-carboxylic acid tert-butyl ester

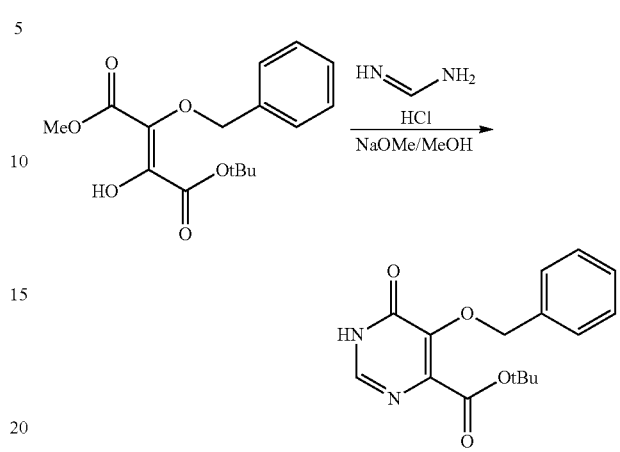

Initial exploratory work on the synthesis of 5-Benzyloxy-6-oxo-1,6-dihydro-pyrimidine-4-carboxylic acid tert-butyl ester was performed on the crude coupled product with potassium t-butoxide as base using the procedure described in U.S. Patent Publication No. 2005/0090668. A mixture of the coupled product (1 equiv.) and formamidine HCl (1.5 equiv.) in MeOH (10 vol.) was treated with 4.5 equiv. of t-BuOK (1M in t-BuOH) at 0° C. The resulting mixture was stirred at room temperature for 20 h, saturated $NH_4Cl$ was added, the mixture was extracted with EtOAc. The combined organic extracts were washed with brine, dried and concentrated to give a beige solid. Chromatography of the crude product gave 30% yield of a white solid. $^1$HNMR conforms except for small amount of unknown contaminant. Mass spec: m/z=247, 303, 605 corresponds to (M-tBu)+1, M+1 and 2M+1. The reaction was repeated in larger scale with NaOMe as base to give 30% yield of the desired product and 4% of the corresponding methyl ester. Subsequently, the yield was improved to 65.4% using NaOMe as base. The results are summarized in the following table.

| Starting material | Conditions | Isolated Product |
|---|---|---|
| 0.9 g Benzyloxyacetic acid methyl ester 1.2 g Oxalic acid tert-butyl ester methyl ester | 1.5 eq. LDA 12 vol THF −78° C. 1 h to rt 1 h | Crude yield 1.35 g (87%) TLC 1 major spot Used in the next step without purification |
| 1.8 g Benzyloxyacetic acid methyl ester 2.4 g Oxalic acid tert-butyl ester methyl ester | 1.5 eq. LDA 12 vol THF −78° C. 1 h to rt 1 h | Chromatographed on silica gel 2.4 g (78% yield) TLC 1 single spot |
| 14.2 g Benzyloxyacetic acid methyl ester 18.9 g Oxalic acid tert-butyl ester methyl ester | 1.5 eq. LDA 12 vol THF −78° C. 1 h to rt 1 h | Crude yield 23.8 g (98%) TLC 1 major spot 3.3 g used in the next step without purification. 20.5 g Chromatographed on silica gel to give 16 g product |
| 14.2 g Benzyloxyacetic acid methyl ester 18.9 g Oxalic acid tert-butyl ester methyl ester | 1.5 eq. LDA 12 vol THF −78° C. 1 h to rt 1 h | 10 g of 2-Benzyloxy-3-hydroxy-but-2-enedioic acid 4-tert-butyl ester 1-methyl ester isolated after chromatography |
| 12 g Benzyloxyacetic acid methyl ester 16 g Oxalic acid tert-butyl ester methyl ester | 1.5 eq. LDA 12 vol THF −78° C. 1 h to rt 1 h | Chromatographed on silica gel 14 g (68.3% yield) TLC 1 single spot |
| 12 g Benzyloxyacetic acid methyl ester 16 g Oxalic acid tert-butyl ester methyl ester | 1.5 eq. LDA 12 vol THF −78° C. 1 h to rt 1 h | Chromatographed on silica gel 14.5 g (70.7% yield) TLC 1 single spot |

Synthesis of 5-Benzyloxy-6-oxo-1,6-dihydro-pyrimidine-4-carboxylic acid tert-butyl ester

| Starting material | Conditions | Isolated Product |
|---|---|---|
| 885 mg 2-Benzyloxy-3-hydroxy-but-2-enedioic acid 4-tert-butyl ester 1-methyl ester<br>342 mg formamidine HCl | 12.75 ml t-BuOK (1M)<br>8 ml MeOH<br>0° C. 0.25 h to rt 20 h | Chromatographed 250 mg (30%) $^1$HNMR conforms Mass spec: m/z = 247 (M − tBu) + 1, 303 (M + 1) and 605 (2M + 1) |
| 1.78 g 2-Benzyloxy-3-hydroxy-but-2-enedioic acid 4-tert-butyl ester 1-methyl ester<br>511.8 mg formamidine HCl | 3.97 ml NaOMe (25% w/w)<br>6 ml MeOH<br>0° C. 0.25 h to rt 20 h | Chromatographed 517 mg (30%) $^1$HNMR conforms 58 mg (4%) of the methyl ester also isolated |
| 3.3 g crude 2-Benzyloxy-3-hydroxy-but-2-enedioic acid 4-tert-butyl ester 1-methyl ester<br>962 mg formamidine HCl | 7.4 ml NaOMe (25% w/w)<br>12 ml MeOH<br>0° C. 0.25 h to rt 60 h | Quench with 1N HCl, product precipitate and filtered. Filtrate extracted with EtOAc and chromatographed. Combined product swish with 20% EtOAc and filtered to give 527 mg methyl ester |
| 16 g purified 2-Benzyloxy-3-hydroxy-but-2-enedioic acid 4-tert-butyl ester 1-methyl ester<br>5.02 g formamidine HCl | 35 ml NaOMe (25% w/w)<br>60 ml MeOH<br>0° C. 0.25 h to rt 17 h | Quench with 1N HCl, extracted with EtOAc. Concentrate to a solid, swished with 40% EtOAc and filtered: 6.45 g.<br>Filtrate concentrated and chromatographed to give 2.57 g t-Bu ester and 0.73 g mixture of t-Bu and Me ester. |
| 8.4 g 2-Benzyloxy-3-hydroxy-but-2-enedioic acid 4-tert-butyl ester 1-methyl ester<br>2.92 g formamidine HCl | 18.7 ml NaOMe (25% w/w)<br>32 ml MeOH<br>0° C. 0.25 h to rt 17 h | 5 g of 5-Benzyloxy-6-oxo-1,6-dihydro-pyrimidine-4-carboxylic acid tert-butyl ester isolated plus 3.3 g ML |
| 14 g purified 2-Benzyloxy-3-hydroxy-but-2-enedioic acid 4-tert-butyl ester 1-methyl ester<br>4.4 g formamidine HCl | 32 ml NaOMe (25% w/w)<br>60 ml MeOH<br>0° C. 0.25 h to rt 17 h | Quench with 1N HCl, extracted with EtOAc. Concentrate to a solid, swished with 40% EtOAc and filtered: 7.75 g.<br>56.3% yield + M.L. |
| 14.3 g purified 2-Benzyloxy-3-hydroxy-but-2-enedioic acid 4-tert-butyl ester 1-methyl ester<br>4.4 g formamidine HCl | 32 ml NaOMe (25% w/w)<br>60 ml MeOH<br>0° C. 0.25 h to rt 17 h | Quench with 1N HCl, extracted with EtOAc. Concentrate to a solid, swished with 40% EtOAc and filtered: 9.0 g.<br>65.4% yield + M.L. |

Synthesis of 5-Benzyloxy-1-methyl-6-oxo-1,6-dihydro-pyrimidine-4-carboxylic acid tert-butyl ester

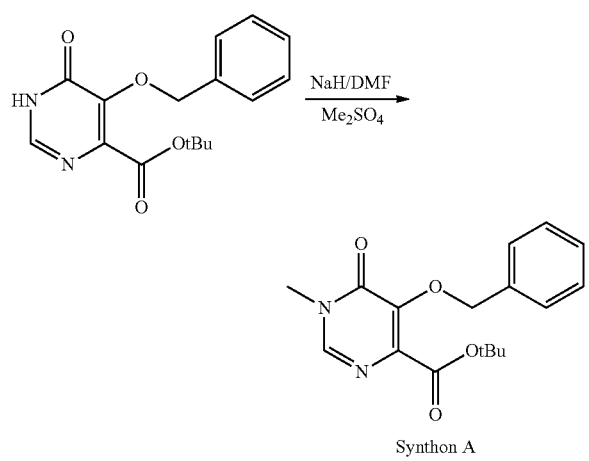

Synthon A

Using a procedure described in U.S. Patent Publication No. 2005/0090668, a solution of 5-benzyloxy-6-oxo-1,6-dihydro-pyrimidine-4-carboxylic acid tert-butyl ester was first treated with NaH (1.3 equiv.) in DMF followed by the addition of dimethylsulfate (1.3 equiv.) to give mainly the desired product after 2 h at room temperature. The reaction mixture was quenched with cold HCl (1N, 30 vol.) and extracted with EtOAc (3×30 vol.). The combined organic extracts were washed with dilute HCl and brine, dried and concentrated to an oil. Chromatography of the crude product (eluted with 40-60% EtOAc/hexane) gave 88% yield of the N-methylated compound (Synthon A).

Synthesis of 5-Benzyloxy-1-methyl-6-oxo-1,6-dihydro-pyrimidine-4-carboxylic acid tert-butyl ester

| Starting material | Conditions | Isolated Product |
|---|---|---|
| 151 mg 5-benzyloxy-6-oxo-1,6-dihydro-pyrimidine-4-carboxylic acid tert-butyl ester<br>82 mg Me$_2$SO$_4$ | 26 mg NaH (60% in oil)<br>2 ml DMF<br>0° C. 0.25 h to rt 1.5 h | TLC showed one major product. Crude $^1$HNMR conforms. Crude yield 173 mg |
| 273 mg 5-benzyloxy-6-oxo-1,6-dihydro-pyrimidine-4-carboxylic acid tert-butyl ester<br>148 mg Me$_2$SO$_4$ | 47 mg NaH (60% in oil)<br>4 ml DMF<br>0° C. 0.25 h to rt 2 h | Crude product combined with product above and chromatographed to give 392 mg (88%) yield of desired product. $^1$HNMR conforms |
| 3.03 g 5-benzyloxy-6-oxo-1,6-dihydro-pyrimidine-4-carboxylic acid tert-butyl ester<br>1.64 g Me$_2$SO$_4$ | 520 mg NaH (60% in oil)<br>30 ml DMF<br>0° C. 0.25 h to rt 1.5 h | Chromatography gave 2.15 g Synthon A (64.7%) |

Synthesis of 5-Benzyloxy-1-methyl-6-oxo-1,6-dihydro-pyrimidine-4-carboxylic acid N'-[2-(4-fluorophenyl)-acetyl]-hydrazide Synthon A was reacted with 1 equiv. of 1N sodium hydroxide to yield the 5-benzyloxy-1-methyl-6-oxo-1,6-dihydro-pyrimidine-4-carboxylic acid.

Synthesis of 5-Benzyloxy-1-methyl-6-oxo-1,6-dihydro-pyrimidine-4-carboxylic acid

| Starting material | Conditions | Isolated Product |
|---|---|---|
| 50 mg of 5-Benzyloxy-1-methyl-6-oxo-1,6-dihydro-pyrimidine-4-carboxylic acid tert-butyl ester | 1 equiv. NaOH (1N), 10 v EtOH 25° C. for 20 h | 5-Benzyloxy-1-methyl-6-oxo-1,6-dihydro-pyrimidine-4-carboxylic acid isolated |
| 1.7 g of 5-Benzyloxy-1-methyl-6-oxo-1,6-dihydro-pyrimidine-4-carboxylic acid tert-butyl ester | 1 equiv. NaOH (1N), 10 v EtOH 25° C. for 20 h | 1.34 g of 5-Benzyloxy-1-methyl-6-oxo-1,6-dihydro-pyrimidine-4-carboxylic acid isolated |
| 4.8 g of 5-Benzyloxy-1-methyl-6-oxo-1,6-dihydro-pyrimidine-4-carboxylic acid tert-butyl ester | 1 equiv. NaOH (1N), 10 v EtOH 25° C. for 20 h | 3.38 g of 5-Benzyloxy-1-methyl-6-oxo-1,6-dihydro-pyrimidine-4-carboxylic acid isolated 85.6% yield. |
| 8.3 g of 5-Benzyloxy-1-methyl-6-oxo-1,6-dihydro-pyrimidine-4-carboxylic acid tert-butyl ester | 1 equiv. NaOH (1N), 10 v EtOH 25° C. for 20 h | 6.7 g of 5-Benzyloxy-1-methyl-6-oxo-1,6-dihydro-pyrimidine-4-carboxylic acid isolated 98.2% yield. |

Synthesis of (4-Fluoro-phenyl)-acetic acid hydrazide

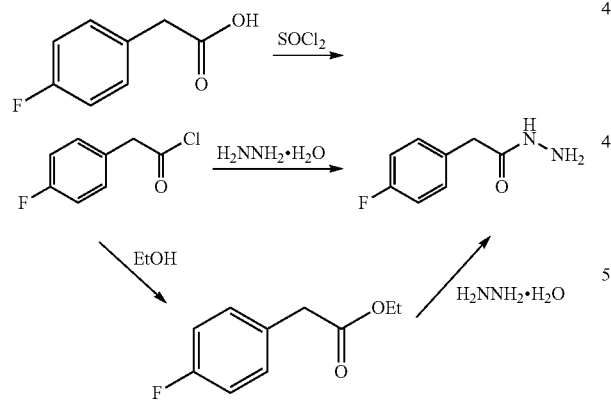

(4-Fluoro-phenyl)-acetyl chloride was readily prepared from the corresponding acid by refluxing the acid in thionyl chloride for 1 h. However, the acid chloride was too reactive. Addition of hydrazine hydrate to a solution of the acid chloride gave only the dimer. Reverse addition of acid chloride to hydrazine hydrate at 0° C. gave the desired hydrazide with some dimer. The acid chloride was then transformed to the corresponding ethyl ester. Reaction of the ethyl ester with 2 equiv. of hydrazine hydrate in refluxing EtOH gave cleanly the (4-Fluoro-phenyl)-acetic acid hydrazide in 76% yield. The results are summarized below.

Synthesis of (4-Fluoro-phenyl)-acetic acid hydrazide

| Starting material | Conditions | Isolated Product |
|---|---|---|
| 2.5 g (4-Fluoro-phenyl)-acetic acid | 6 ml SOCl$_2$ 80° C. for 1 h, evaporate to dryness | 2.78 g of (4-Fluoro-phenyl)-acetyl chloride isolated |
| 172 mg of (4-Fluoro-phenyl)-acetyl chloride | Acid chloride added to H$_2$NNH$_2$•H$_2$O in 5 ml CH$_2$Cl$_2$ at 0° C. Stir at 0° C. for 1 h, 20° C. for 0.5 h | 114 mg (4-Fluoro-phenyl)-acetic acid hydrazide isolated plus 37 mg dimer |
| 2.4 g of (4-Fluoro-phenyl)-acetyl chloride | 10 ml EtOH 20° C. for 1 h | 2.55 g (4-Fluoro-phenyl)-acetic acid ethyl ester |
| 2.55 g (4-Fluoro-phenyl)-acetic acid ethyl ester | 2 equiv. of H$_2$NNH$_2$•H$_2$O, 4 v EtOH, stir at 85° C. for 5 h | 1.8 g (4-Fluoro-phenyl)-acetic acid hydrazide isolated |
| 10 g (4-Fluoro-phenyl)-acetic acid | 18 ml SOCl$_2$ 80° C. for 1 h, evaporate to dryness | 11.88 g of (4-Fluoro-phenyl)-acetyl chloride isolated |
| 11.88 g of (4-Fluoro-phenyl)-acetyl chloride | 50 ml EtOH | 20° C. for 1 h 11.3 g (4-Fluoro-phenyl)-acetic acid ethyl ester |
| CKL-3-44 11 g (4-Fluoro-phenyl)-acetic acid ethyl ester | 2 equiv. of H$_2$NNH$_2$•H$_2$O, 4 v EtOH, stir at 85° C. for 5 h | 9.2 g (4-Fluoro-phenyl)-acetic acid hydrazide isolated |

The carboxylic acid was transformed to the corresponding acid chloride by refluxing the latter in thionyl chloride. Reaction of the acid chloride with (4-fluoro-phenyl)-acetic acid hydrazide gave almost quantitatively the desired bis-hydrazide.

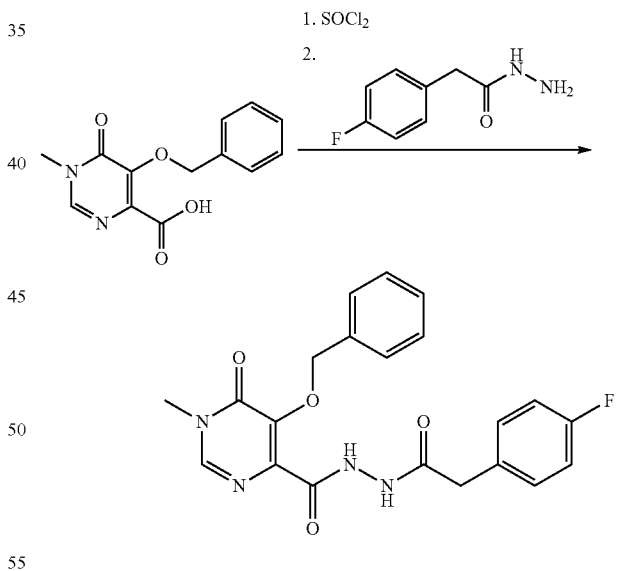

Synthesis of 5-Benzyloxy-1-methyl-6-oxo-1,6-dihydro-pyrimidine-4-carboxylic acid N'-[2-(4-fluorophenyl)-acetyl]-hydrazide

| Starting material | Conditions | Isolated Product |
|---|---|---|
| 1. 100 mg 5-Benzyloxy-1-methyl-6-oxo-1,6-dihydro-pyrimidine-4- | Reflux 1 h, concentrated under vacuum, used as is. Add acid chloride | 160 mg isolated, NMR MS conformed. |

43
-continued

| Starting material | Conditions | Isolated Product |
|---|---|---|
| carboxylic acid, 2 ml $SOCl_2$<br>2. 63.8 mg (4-Fluoro-phenyl)-acetic acid hydrazide (1.0 equiv.), 72 mg $Et_3N$ (2.0 equiv.) | solution in $CH_2Cl_2$ (1 ml) to a suspension of hydrazide in $CH_2Cl_2$ (1 ml), at 0°. Stir at rt for 1 h. | 160 mg isolated, NMR MS conformed |
| 1. 1.15 g 5-Benzyloxy-1-methyl-6-oxo-1,6-dihydro-pyrimidine-4-carboxylic acid, 10 ml $SOCl_2$<br>2. 742 mg (4-Fluoro phenyl)-acetic acid hydrazide (1.0 equiv.), 892 mg $Et_3N$ (2.0 equiv.) | Reflux 1 h, concentrated under vacuum, used as is. Add acid chloride solution in $CH_2Cl_2$ (10 ml) to a suspension of hydrazide in $CH_2Cl_2$ (10 ml), at 0°. Stir at rt for 1 h. | 1.8 g isolated (99%), NMR conformed. |
| 1. 3.3 g 5-Benzyloxy-1-methyl-6-oxo-1,6-dihydro-pyrimidine-4-carboxylic acid, 30 ml $SOCl_2$<br>2. 2.13 g (4-Fluoro-phenyl)-acetic acid hydrazide (1.0 equiv.), 3.5 mL $Et_3N$ (2.0 equiv.) | Reflux 1 h, concentrated under vacuum, used as is. Add acid chloride solution in $CH_2Cl_2$ (10 ml) to a suspension of hydrazide in $CH_2Cl_2$ (10 ml), at 0°. Stir at rt for over night. | 4.97 g isolated yield 95.6% NMR conformed. |
| 1. 6.7 g 5-Benzyloxy-1-methyl-6-oxo-1,6-dihydro-pyrimidine-4-carboxylic acid, 30 ml $SOCl_2$<br>2. 4.33 g (4-Fluoro-phenyl)-acetic acid hydrazide (1.0 equiv.), 3.5 mL $Et_3N$ (2.0 equiv.) | Reflux 1 h, concentrated under vacuum, used as is. Add acid chloride solution in $CH_2Cl_2$ (10 ml) to a suspension of hydrazide in $CH_2Cl_2$ (10 ml), at 0°. Stir at rt for over night. | 9.44 g isolated yield 89.3% NMR conformed. |

44
Synthesis of 5-Benzyloxy-6-[5-(4-fluoro-benzyl)-[1,3,4]oxadiazol-2-yl]-3-methyl-3H-pyrimidin-4-one

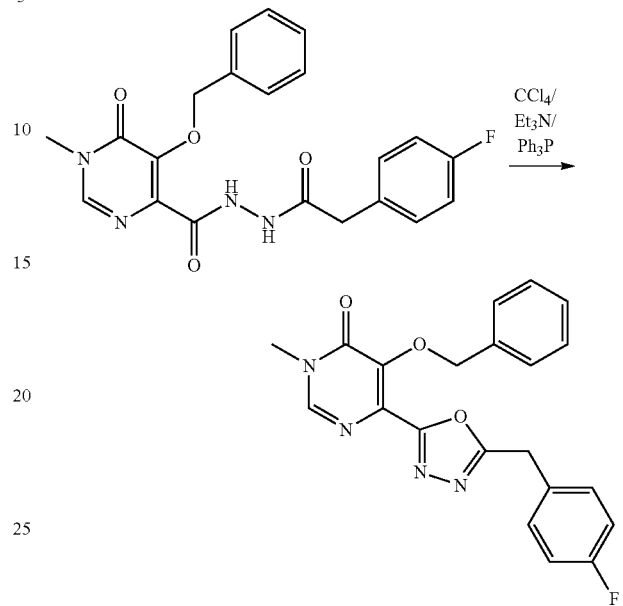

Following the procedure described in European Patent No. 1698628, 5-benzyloxy-1-methyl-6-oxo-1,6-dihydro-pyrimidine-4-carboxylic acid N'-[2-(4-fluoro-phenyl)-acetyl]-hydrazide was treated with $CCl_4$ (7 equiv.), $Ph_3P$ (3 equiv.) and $Et_3N$ (3 equiv.) in $CH_3CN$ (10 vol) at room temperature for 1.5 h. TLC showed only one product formed. The reaction mixture was diluted with EtOAc, washed with aqueous $NaHCO_3$ and brine, dried and concentrated to give a crude solid. For the 1.8 g scale reaction, chromatography (4 columns) plus recrystallization twice was needed to isolate the desired product without $Ph_3P=O$ contamination. NMR and MS confirmed the structure.

| Starting material | Conditions | Isolated Product |
|---|---|---|
| 160 mg bis hydrazide 0.262 ml $CCl_4$ (7 eq.) 0.164 mL $Et_3N$ (3 eq.) 306 mg $Ph_3P$ (3 eq.) | $Ph_3P$ was added to a suspension of bis hydrazide, $CCl_4$ and $Et_3N$ at rt. Stir for 1 h at rt. | 40 mg of cyclised oxadiazole contaminated by $Ph_3P$ isolated after chromatography (eluted with 100% EtOAc). NMR, MS conformed. |
| 1.8 g bis hydrazide 3 ml $CCl_4$ (7 eq.) 1.8 mL $Et_3N$ (3 eq.) 3.45 g $Ph_3P$ (3 eq.) | $Ph_3P$ was added to a suspension of bis hydrazide, $CCl_4$ and $Et_3N$ at rt. Stir for 1.5 h at rt. | First column chromatography gave 1.91 g of desired product contaminated by small amount of $Ph_3P=O$ and 3.5 g of $Ph_3P=O$ containing small amount of product. The $Ph_3P=O$ fraction was repurified by chromatography to give more desired product. All the impure fractions were combined and chromatographed, the product isolated was first crystallized from EtOAc and then recrystallization in toluene gave a combined yield of 1.3 g (75%) of product. |
| 4.95 g bis hydrazide 8.13 ml $CCl_4$ (7 eq.) 5.04 mL $Et_3N$ (3 eq.) 9.49 g $Ph_3P$ (3 eq.) | $Ph_3P$ was added to a suspension of bis hydrazide, $CCl_4$ and $Et_3N$ at rt. Stir over night at rt. | First column chromatography gave 1.6 g of desired product contaminated by small amount of $Ph_3P=O$ and 5.2 g of desired product with $Ph_3P=O$. |

-continued

| Starting material | Conditions | Isolated Product |
|---|---|---|
| 9.4 g bis hydrazide<br>8.13 ml CCl$_4$ (7 eq.)<br>5.04 mL Et$_3$N (3 eq.)<br>9.49 g Ph$_3$P (3 eq.) | Ph$_3$P was added to a suspension of bis hydrazide, CCl$_4$ and Et$_3$N at rt. Stir over night at rt. | Recrystallisation of 1.6 g with toluene gives 1.3 g of pure product.<br>First column chromatography gave 5.0 g of desired product contaminated by small amount of Ph$_3$P=O and 7.5 g of desired product with Ph$_3$P=O.<br>Recrystallisation of 5.0 g with toluene gives 4.1 g of pure product. |

Synthesis of 5-Benzyloxy-6-[5-(4-fluoro-benzyl)-[1,3,4]oxadiazol-2-yl]-3-methyl-3H-pyrimidine-4-thione 5-Benzyloxy-6-[5-(4-fluoro-benzyl)-[1,3,4]oxadiazol-2-yl]-3-methyl-3H-pyrimidin-4-one was treated with 0.62 equiv of Lawesson's reagent at 80-85° C. in toluene for 5-7 h. TLC showed one major product formation with some substrate still present. Chromatography (eluted with 70%-90% EtOAc/hexane) gave ~50% yield of the title compound.

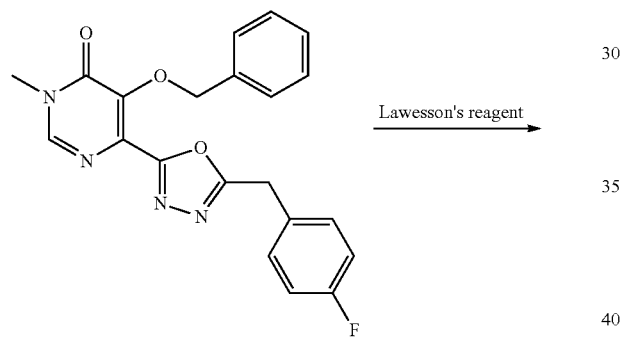

Lawesson's reagent

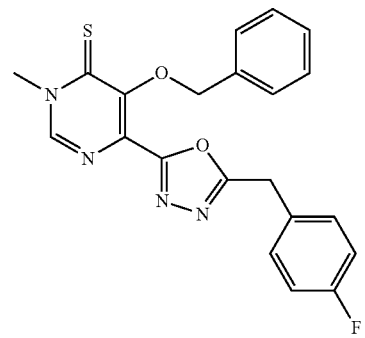

| Starting material | Conditions | Isolated Product |
|---|---|---|
| 100 mg 5-Benzyloxy-6-[5-(4-fluoro-benzyl)-[1,3,4]oxadiazol-2-yl]-3-methyl-3H-pyrimidin-4-one<br>63 mg Lawesson's reagent (0.62 eq.) | 3 ml toluene, 80-85° C. for 5 h | 50 mg of a yellow powder. NMR, MS conformed. |
| 392 mg 5-Benzyloxy-6-[5-(4-fluoro-benzyl)-[1,3,4]oxadiazol-2-yl]-3-methyl-3H-pyrimidin-4-one<br>63 mg Lawesson's reagent (0.62 eq.) | 3 ml toluene, 80-85° C. for 5 h | 50 mg of a yellow powder. NMR, MS conformed. |
| 350 mg 5-Benzyloxy-6-[5-(4-fluoro-benzyl)-[1,3,4]oxadiazol-2-yl]-3-methyl-3H-pyrimidin-4-one<br>233 mg Lawesson's reagent (0.65 eq.) | 10 ml toluene, 80-85° C. for 7 h | 269 mg (74%) of a yellow powder |
| 190 mg 5-Benzyloxy-6-[5-(4-fluoro-benzyl)-[1,3,4]oxadiazol-2-yl]-3-methyl-3H-pyrimidin-4-one<br>126 mg Lawesson's reagent (0.65 eq.) | 6 ml toluene, 80-85° C. for 14 h | 150 mg (76%) of a yellow powder. NMR, MS conformed. |
| 2.0 g 5-Benzyloxy-6-[5-(4-fluoro-benzyl)-[1,3,4]oxadiazol-2-yl]-3-methyl-3H-pyrimidin-4-one<br>1.28 g Lawesson's reagent (0.62 eq.) | 55 ml toluene, 80-85° C. for 8 h, r.t. for 16 hrs. | 1.2 g (57.7%) of a yellow powder. NMR, MS conformed. |
| 3.75 g 5-Benzyloxy-6-[5-(4-fluoro-benzyl)-[1,3,4]oxadiazol-2-yl]-3-methyl-3H-pyrimidin-4-one<br>2.51 g Lawesson's reagent (0.62 eq.) | 94 ml toluene, 80-85° C. for 8 h, r.t. for 16 hrs. | 2.75 g (70.5%) of a yellow powder. NMR, MS conformed. |

Reaction of 5-Benzyloxy-6-[5-(4-fluoro-benzyl)-[1,3,4]oxadiazol-2-yl]-3-methyl-3H-pyrimidine-4-thione with N,O-bis(trimethylsilyl)hydroxylamine in the presence of Hg(OAc)$_2$

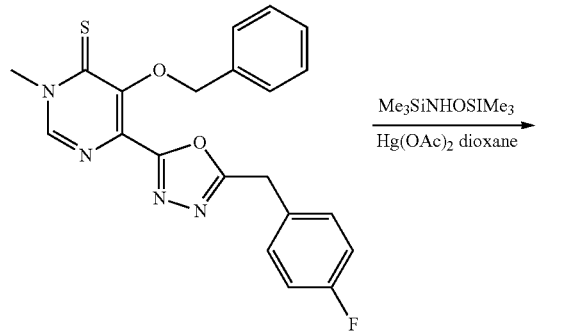

Me$_3$SiNHOSIMe$_3$
Hg(OAc)$_2$ dioxane
→

-continued

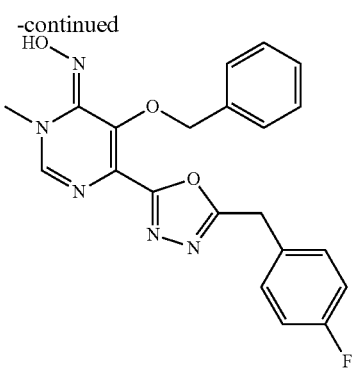

Reaction of 5-Benzyloxy-6-[5-(4-fluoro-benzyl)-[1,3,4]oxadiazol-2-yl]-3-methyl-3H-pyrimidine-4-thione with N,O-bis(trimethylsilyl)hydroxylamine in the presence of Hg(OAc)$_2$, the desired amidoxime derivative was isolated as a mixture of syn- and anti-isomers. Mass spec: m/z=408 (M+1) conforms to structure expected.

| Starting material | Conditions | Isolated Product |
| --- | --- | --- |
| 50 mg 5-benzyloxy-6-[5-(4-fluoro-benzyl)-[1,3,4]oxadiazol-2-yl]-3-methyl-3H-pyrimidine-4-thione (75% pure) 83 mg N,O-bis(trimethylsilyl)hydroxylamine (5 equiv.) 40 mg Hg(Oac)2 1.4 equiv. | 2.5 ml dioxane, 4 h rt | Small amount of expected product as mixture of isomers. MS: m/z = 408 (M + 1) |
| 400 mg 5-benzyloxy-6-[5-(4-fluoro-benzyl)-[1,3,4]oxadiazol-2-yl]-3-methyl-3H-pyrimidine-4-thione (pure) 1.05 mL N,O-bis(trimethylsilyl)hydroxylamine (5 equiv.) 400 mg Hg(Oac)2 1.4 equiv. | 20 ml dioxane, 3 h rt | Small amount of expected product. MS: m/z = 408 (M + 1) ~20 mg of pure product |
| 400 mg 5-benzyloxy-6-[5-(4-fluoro-benzyl)-[1,3,4]oxadiazol-2-yl]-3-methyl-3H-pyrimidine-4-thione (pure) 2.0 mL N,O-bis(trimethylsilyl)hydroxylamine (10 equiv.) 400 mg Hg(Oac)2 1.4 equiv. | 20 ml dioxane, 3 h rt | Small amount of expected product. MS: m/z = 408 (M + 1) ~10 mg of pure product |
| 200 mg 5-benzyloxy-6-[5-(4-fluoro-benzyl)-[1,3,4]oxadiazol-2-yl]-3-methyl-3H-pyrimidine-4-thione (pure) 0.5 mL N,O-bis(trimethylsilyl)hydroxylamine (5 equiv.) 200 mg Hg(Oac)2 1.4 equiv. | 20 ml toluene, 2 h, 90° C. same TLC | n/a |
| 200 mg 5-benzyloxy-6-[5-(4-fluoro-benzyl)-[1,3,4]oxadiazol-2-yl]-3-methyl-3H-pyrimidine-4-thione (pure) 0.5 mL N,O-bis(trimethylsilyl)hydroxylamine (5 equiv.) 200 mg Hg(Oac)2 1.4 equiv. | 20 ml THF, 2 h, r.t. same TLC | Purification of above and this one give ~50 mg of good product. |
| 2.48 g 5-benzyloxy-6-[5-(4-fluoro-benzyl)[1,3,4]oxadiazol-2-yl]-3-methyl-3H-pyrimidine-4-thione (pure) 6.48 mL N,O-bis(trimethylsilyl)hydroxylamine (5 equiv.) 2.66 g Hg(Oac)$_2$ 1.4 equiv. | 125 ml Dioxane, 1 h, r.t. same TLC | Purification by silica gives 190 mg of desire product. (7.66% yield). |

6-[5-(4-Fluoro-benzyl)-[1,3,4]oxadiazol-2-yl]-5-hydroxy-3-methyl-3H pyrimidin-4-one oxime (COTI-HIV-1DOxime)

5-Benzyloxy-6-[5-(4-fluoro-benzyl)-[1,3,4]oxadiazol-2-yl]-3-methyl-3H-pyrimidin-4-one oxime was hydrogenated at 1 atmosphere of hydrogen in the presence of equal weight of 10% Pd/C to give 68% yield of 6-[5-(4-fluoro-benzyl)-[1,3,4]oxadiazol-2-yl]-5-hydroxy-3-methyl-3H-pyrimidin-4-one oxime (COTI-HIV-1DOxime or, also referred to as COTI-HIV-1). Results are summarized below.

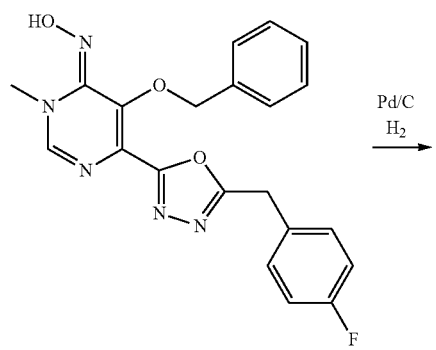

COTI-HIV-1

Synthesis of 6-[5-(4-fluoro-benzyl)-[1,3,4]oxadiazol-2-yl]-5-hydroxy-3-methyl-3H-pyrimidin-4-one oxime (COTI-HIV-1DOxime)

| Starting material | Conditions | Isolated Product |
|---|---|---|
| ~50 to 100 mg of 5-Benzyloxy-6-[5-(4-fluoro-benzyl)-[1,3,4]oxadiazol-2-yl]-3-methyl-3H-pyrimidin-4-one oxime (+/−pure) 100% w/w Pd/C 10% and 50% water. | 25 ml THF, rt 1 atm of H₂. | 28 mg COTI-HIV-1 + by-product 56 mg of +/−pure COTI-HIV-1DOxime and by product |
| 190 mg of 5-Benzyloxy-6-[5-(4-fluoro-benzyl)-[1,3,4]oxadiazol-2-yl]-3-methyl-3H-pyrimidin-4-one oxime (pure) 100% w/w Pd/C 10% and 50% water. | 25 ml THF, rt 1 atm of H₂. | The crude is purifying by silica with the above products to give 100 mg (68%) of pure desire product. (M/Z = 318) NMR ¹H conform |

Example 1A

Synthesis of the compound of the following formula:

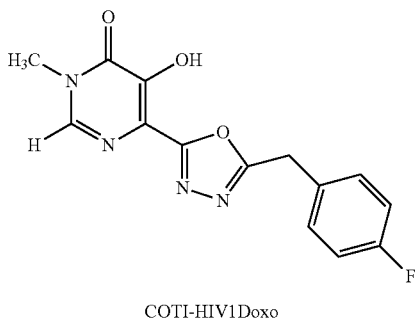 [SMILES: Cn1cnc(-c2nnc(Cc3ccc(F)cc3)o2)c(O)c1=O]

COTI-HIV1Doxo is as follows:

6-[5-(4-Fluoro-benzyl)-[1,3,4]oxadiazol-2-yl]-5-hydroxy-3-methyl-3H pyrimidin-4-one a) Preparation of 6-[5-(4-Fluoro-benzyl)-[1,3,4]oxadiazol-2-yl]-5-hydroxy-3-methyl-3H-pyrimidin-4-one by acid catalyzed debenzylation

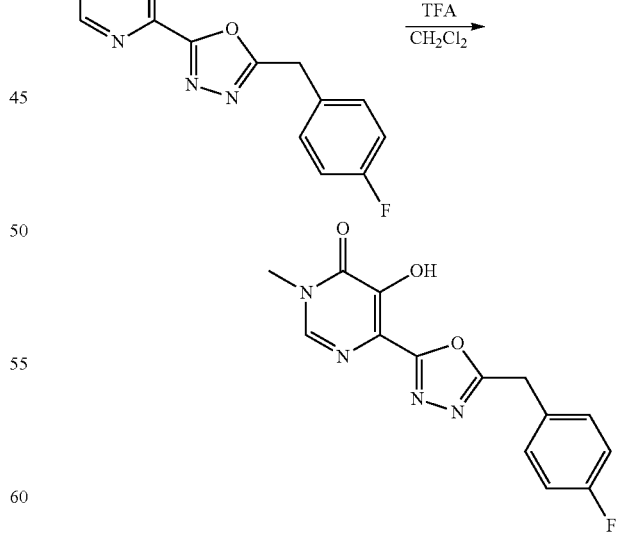

Reaction of 5-benzyloxy-6-[5-(4-fluoro-benzyl)-[1,3,4]oxadiazol-2-yl]-3-methyl-3H-pyrimidin-4-one and a 1:1 mixture of TFA/CH₂Cl₂ gave the debenzylated product in reasonable yield. Results are summarized below.

Preparation of 6-[5-(4-Fluoro-benzyl)-[1,3,4]oxadi-azol-2-yl]-5-hydroxy-3-methyl-3H-pyrimidin-4-one

| Starting material | Conditions | Isolated Product |
|---|---|---|
| 24 mg 5-benzyloxy-6-[5-(4-fluoro-benzyl)-[1,3,4]oxadiazol-2-yl]-3-methyl-3H-pyrimidin-4-one | 0.3 ml CH$_2$Cl$_2$, 0.3 ml TFA, 20 h, rt. Concentrate under vacuum, swished with 20% EtOAc/hexane | Beige solid, $^1$HNMR and MS conformed to expected product |
| 109 mg 5-benzyloxy-6-[5-(4-fluoro-benzyl)-[1,3,4]oxadiazol-2-yl]-3-methyl-3H-pyrimidin-4-one | 1 ml CH$_2$Cl$_2$, 1 ml TFA, 48 h, rt. Concentrate under vacuum, co-distill with EtOAc/heptane, swished with 30% EtOAc/hexane | 65 mg beige solid (77%), $^1$HNMR conformed. |
| 100 mg 5-benzyloxy-6-[5-(4-fluoro-benzyl)-[1,3,4]oxadiazol-2-yl]-3-methyl-3H-pyrimidin-4-one | 1 ml CH$_2$Cl$_2$, 1 ml TFA, 48 h, rt. Concentrate under vacuum, co-distill with EtOAc/heptane, swished with 30% EtOAc/hexane for 20 h | 69 mg beige solid, $^1$HNMR showed an unknown impurity. Re-purify by swishing in 4 ml pure EtOAc for 20 h to give 56 mg of pure product. $^1$HNMR conformed. | b) Preparation of 6-[5-(4-Fluoro-benzyl)-[1,3,4]oxadiazol-2-yl]-5-hydroxy-3-methyl-3H-pyrimidin-4-one by palladium catalyzed debenzylation

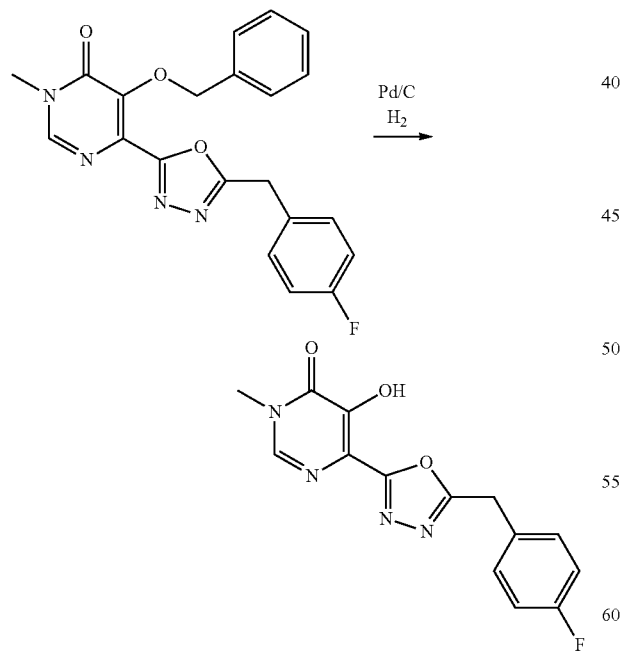

Hydrogenation of 5-Benzyloxy-6-[5-(4-fluoro-benzyl)-[1,3,4]oxadiazol-2-yl]-3-methyl-3H-pyrimidin-4-one in THF with 25% w/w of 10% Pd/C gave 67.5% of the desired product. Results are shown below.

Preparation of 6-[5-(4-Fluoro-benzyl)-[1,3,4]oxadi-azol-2-yl]-5-hydroxy-3-methyl-3H-pyrimidin-4-one by palladium catalyzed debenzylation

| Starting material | Conditions | Isolated Product |
|---|---|---|
| 1.0 g of 5-Benzyloxy-6-[5-(4-fluoro-benzyl)-[1,3,4]oxadiazol-2-yl]-3-methyl-3H-pyrimidin-4-one 250 mg mg 10% Pd/C | 200 ml THF, r.t. 1 atm 30 mins | 0.52 g of pure product (67.5%) 0.35 g of +/−pure product. |

Example 2

Synthesis of COTI-HIV28236

Synthesis of the compound of the following formula:

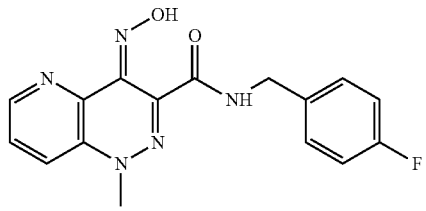

COTI-HIV28236 was conducted according to the following synthetic methodology:

Synthesis of the Common Intermediate 4c

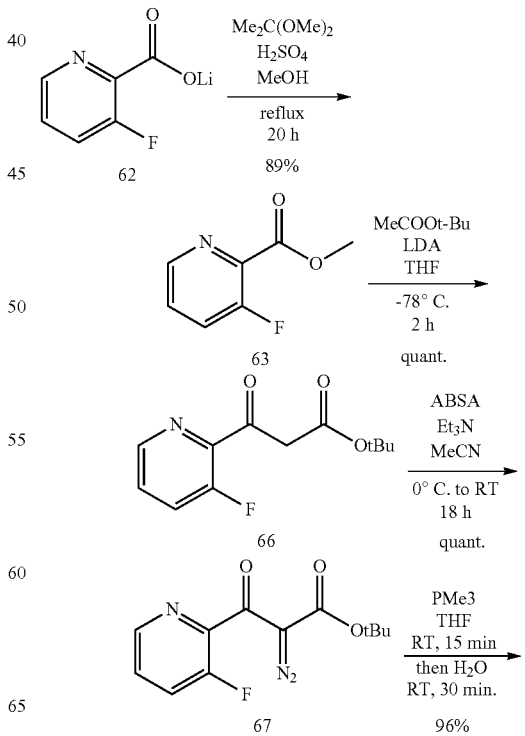

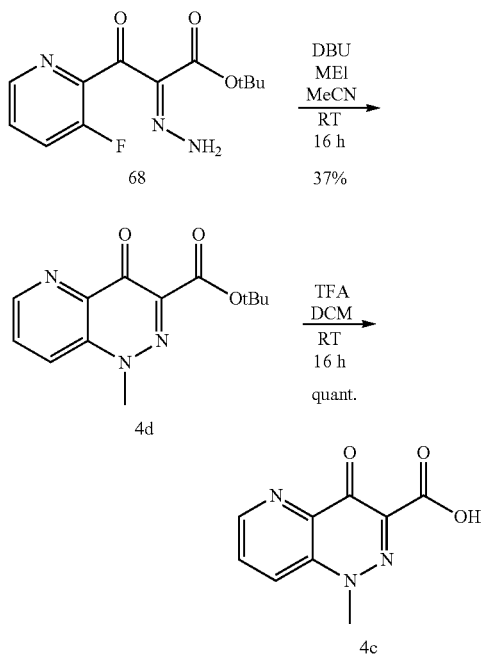

Synthesis of Compound 63:

To a suspension of lithium 3-fluoropyridine-2-carboxylate (10.1 g; 69 mmol; 1 eq.) in methanol (170 mL) were successively added 1,2-dimethoxypropane (17.0 mL; 138 mmol; 2 eq.) and concentrated sulphuric acid (18.0 mL; 345 mmol; 5 eq.). The reaction mixture became homogeneous and turned yellow after addition of sulphuric acid. The mixture was then heated at reflux for 20 hours. After cooling down to room temperature, the solvent was removed under vacuum. The oily residue was slowly poured into a mixture of ethyl acetate (200 mL) and a saturated solution of NaHCO$_3$ (400 mL). At the end of the addition, the aqueous layer was again saturated by addition of solid NaHCO$_3$. The layers were then separated and the aqueous phase was extracted with ethyl acetate (2×200 mL). The combined organic phases were dried over Na$_2$SO$_4$, filtered and evaporated to dryness to afford compound 63 as a light yellow solid (9.5 g; yield=89%).

Synthesis of Compound 66:

To a solution of LDA (1.8M in THF/heptane; 72.0 mL; 129 mmol; 2.1 eq.) in THF (60 mL) at −78° C. was added tert-butylacetate (20.0 mL; 148 mmol; 2.4 eq.). The deep red solution was stirred at −78° C. for 45 minutes and maintained at that temperature during the slow addition of a solution of compound 63 (9.5 g; 62 mmol; 1 eq.) in THF (60 mL). The reaction mixture was then stirred for an additional 2 hours and quenched at −78° C. by addition of MTBE (150 mL) and water/acetic acid (1:1; 150 mL). After warming up to room temperature, the layers were separated and the aqueous phase was extracted with MTBE (2×100 mL). The combined organic phases were washed with water (300 mL) and brine (300 mL), dried over Na$_2$SO$_4$, filtered and evaporated to dryness to afford compound 66 as an yellow oil (16.2 g; contaminated with 8.5% w/w of acetic acid; yield=100%).

Synthesis of Compound 67:

To a solution of crude compound 66 (16.2 g; 62 mmol; 1 eq.) in acetonitrile (190 mL) at 0° C. was successively added triethylamine (14.6 mL; 112 mmol; 1.8 eq.) and ABSA (16.3 g; 68 mmol; 1.1 eq.). At the end of the addition, the reaction mixture was allowed to warm up to room temperature. A white solid precipitated progressively from the orange solution. After 18 hours, the reaction mixture was filtered on a Büchner funnel. The white cake was washed with ethyl acetate (450 mL). The mother liquor was decanted and the layers were separated. The organic phase was washed with a saturated solution of NH$_4$Cl (400 mL) and brine (400 mL), dried over Na$_2$SO$_4$, filtered and evaporated to dryness. The orange oily residue was triturated in diethyl ether. After filtration of the brown solid, the evaporation of the mother liquor afforded compound 67 as an orange oil (18.9 g contaminated with 9% w/w of p-AcHN-Ph-SO$_2$NH$_2$, yield=100%).

Synthesis of Compound 68:

To a solution of crude compound 67 (18.9 g; 62 mmol; 1 eq.) in THF (125 mL) at room temperature was slowly added trimethylphosphine (1M/THF; 68.0 mL; 68 mmol; 1.1 eq.). At the end of the addition, the reaction mixture was stirred for 15 minutes and quenched by addition of water (11.0 mL; 616 mmol; 10 eq.). The mixture was stirred for an additional 15 minutes prior to the addition of silica gel (45 g). The solvent was then evaporated under vacuum and the residue, which was adsorbed on silica gel, was purified by flash chromatography on silica gel (eluent: dichloromethane/methanol, 100/0 to 96/4) to afford compound 68 as an orange oil (15.7 g; yield=96%).

Synthesis of Compound 4d:

To a solution of compound 68 (15.7 g; 59 mmol; 1 eq.) in acetonitrile (300 mL) at room temperature were successively added DBU (18.5 mL; 124 mmol; 2.1 eq.) and methyl iodide (3.8 mL; 62 mmol; 1.05 eq.). The reaction mixture became deep red. After stirring for 18 hours at room temperature, the reaction was quenched by addition of a saturated solution of NH$_4$Cl (500 mL). The resulting mixture was extracted with dichloromethane (3×500 mL) and the combined organic phases were washed with brine (1 L), dried over Na$_2$SO$_4$, filtered and evaporated to dryness. The purification of the residue by chromatography on silica gel (eluent: dichloromethane/methanol, 100/0 to 90/10) afforded two fractions containing compound 4d. After evaporation to dryness, the first one was triturated in diethyl ether to afford a first batch of pure compound 4d as a pale orange solid (2.6 g; yield=17%). The second one was dissolved in dichloromethane (500 mL) and the resulting solution was washed with a saturated solution of NH$_4$Cl (2×500 mL), dried over Na$_2$SO$_4$, filtered and evaporated to dryness to afford a second batch of pure compound 4d as a pale orange solid (3.1 g; yield=20%). The two batches were combined (yield=37%).

Synthesis of Compound 4c:

To a solution of compound 4d (3.1 g; 12 mmol; 1 eq.) in dichloromethane (110 mL) at room temperature was added trifluoroacetic acid (12.0 mL; 157 mmol; 13.3 eq.). The reaction mixture turned brown. After stirring at room temperature for 18 hours, the reaction mixture was diluted by addition of diethyl ether (150 mL). The solvent were then removed under vacuum. The beige residue was triturated in diethyl ether to afford compound 4c as a beige solid (2.4 g; yield=100%). $^1$H NMR (DMSO, ppm): 4.29 (s, 3H); 8.02 (m, 1H); 8.52 (m, 1H); 9.01 (m, 1H); and 14.32 (m, COOH).

Synthesis of COTI-HIV28236:

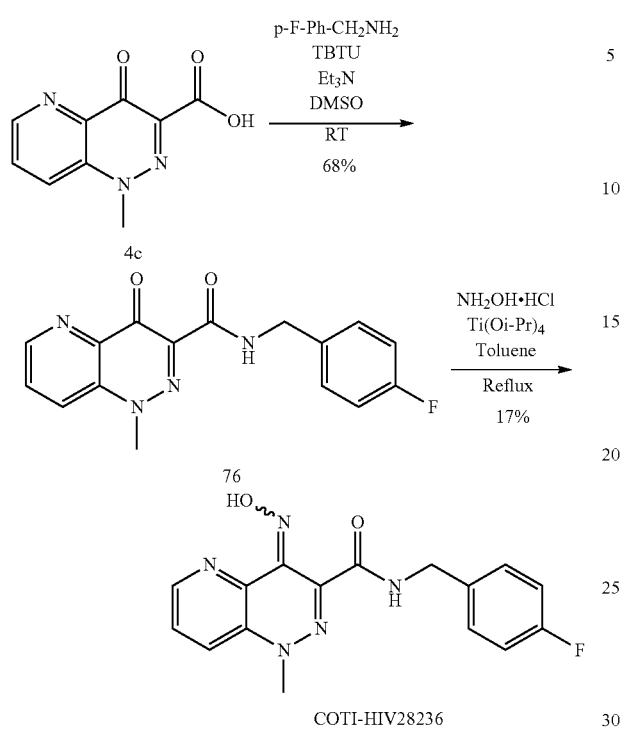

Synthesis of Compound 76:

To a solution of compound 4c (907 mg; 4.4 mmol; 1 eq.) in DMSO (6 mL) at room temperature was successively added triethylamine (2.4 mL; 17.6 mmol; 4 eq.), para-fluorobenzylamine (610 μL; 5.3 mmol; 1.2 eq.) and TBTU (1.70 g; 5.3 mmol; 1.2 eq.). After stirring the mixture at room temperature for 16 hours, the reaction was quenched by addition of a saturated solution of NH$_4$Cl (50 mL). The aqueous phase was then extracted with dichloromethane (5×100 mL). The combined organic phases were combined, dried over Na$_2$SO$_4$, filtered and evaporated to dryness. The residue was dissolved in ethyl acetate (100 mL) and the solution was washed with water (100 mL), brine (100 mL), dried over Na$_2$SO$_4$, filtered and evaporated to dryness. The residue was then triturated in diethyl ether to afford compound 76 as an yellow solid (480 mg; yield=35%). All aqueous layers were then combined and extracted with chloroform (3×250 mL). The combined chloroform phases were dried over Na$_2$SO$_4$, filtered and evaporated to dryness in the presence of silica gel (3 g). The purification by chromatography on silica gel (eluent: dichloromethane/methanol, 98/2 to 90/10) afforded compound 76 as an yellow solid (454 mg; yield=33%). The two batches were combined (yield=68%).

Synthesis of Compound COTI-HIV28236:

To a suspension of compound 76 (228 mg; 73 μmol; 1 eq.) in toluene (3.7 mL) at room temperature was added hydroxylamine hydrochloride (76 mg; 1.10 mmol; 1.5 eq.) and titanium (IV) isopropoxide (330 μL; 1.10 mmol; 1.5 eq.). The reaction mixture was refluxed for 72 hours and evaporated to dryness. The red residue is dissolved in a mixture of a saturated solution of NaHCO$_3$/ethyl acetate/methanol (5:5:1; 55 mL). After separation of the layers, the aqueous phase was extracted with ethyl acetate (3×50 mL). The combined organic phases were washed with brine (100 mL), dried over Na$_2$SO$_4$, filtered and evaporated to dryness. The purification of the residue on silica gel (eluent: dichloromethane/methanol, 100/0 to 98/2) followed by a trituration in methanol afforded compound COTI-HIV28236 as a yellow solid (42 mg; yield=17%). $^1$H NMR (CDCl$_3$, ppm): 3.82 (s, 3H); 4.61 (s, 2H); 6.99 (m, 2H); 7.34 (m, 1H); 7.44 (m, 1H); 7.55 (m, 1H), 8.24 (m, 1H), 9.82 (m, 1H) and 15.71 (m, NOH). $^{13}$C NMR (CDCl$_3$, ppm): 42.3, 43.3, 115.3, 115.6, 121.4, 127.5, 129.7, 129.8, 134.3, 135.8, 138.1, 138.7, 139.7, 160.9, 161.6, and 163.4. MS (ES+IC): m/z (M+H)$^+$328.

Example 3

Synthesis of COTI-HIV28233

Synthesis of the compound of the following formula:

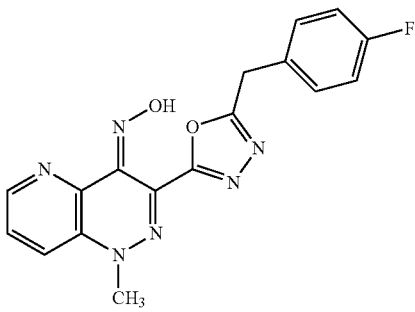

COTI-HIV28233 (COTI-HIV1oxime)

Synthesis of the compound of COTI-HIV28233 was conducted according to the following synthetic methodology. Synthesis of the common intermediate 4c is as described above with respect to Example 2.

Synthesis of COTI-HIV28233:

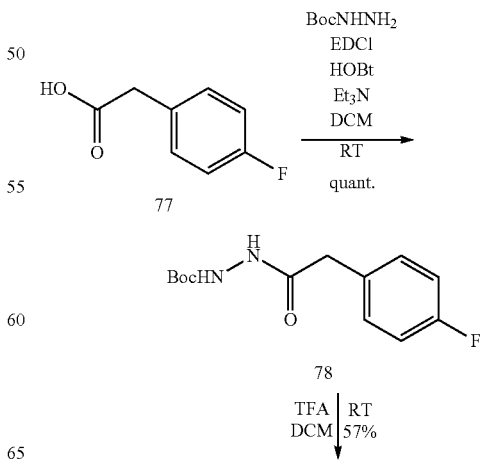

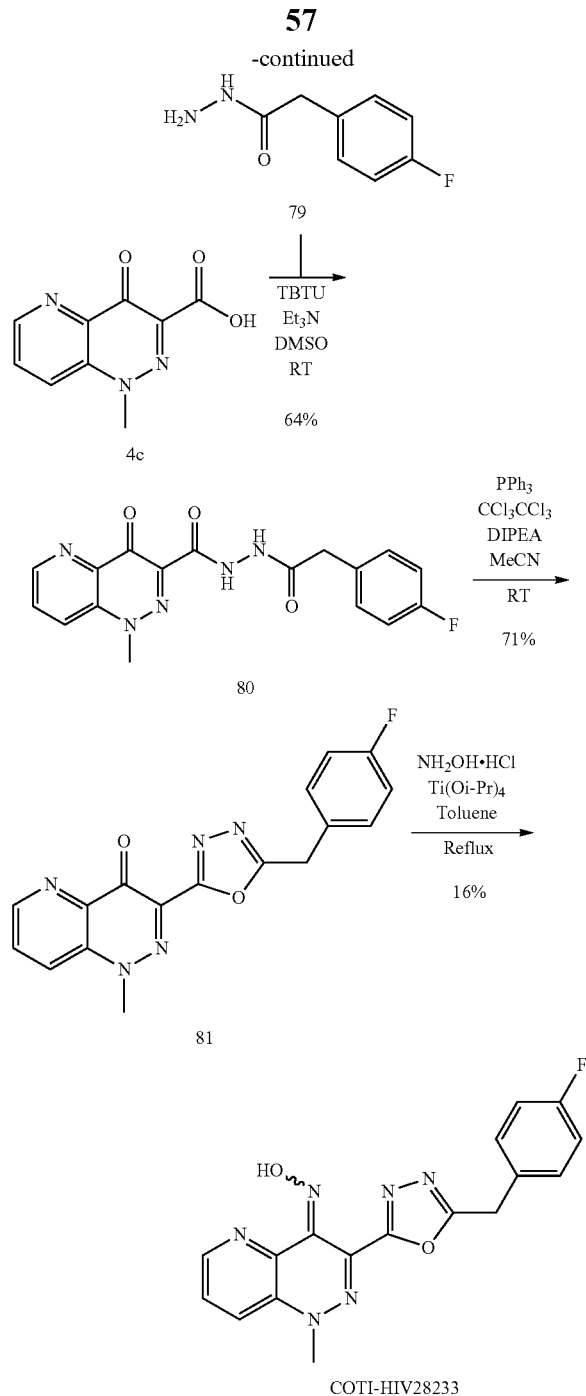

Synthesis of Compound 79:

To a solution of compound 78 (9.1 g; 33 mmol; 1 eq.) in dichloromethane (300 mL) at room temperature was slowly added trifluoroacetic acid (33.0 mL; 434 mmol; 13.2 eq.). The reaction mixture turned light brown. After stirring for 3 hours, the reaction mixture was evaporated to dryness. The colourless residue was dissolved in ethyl acetate (400 mL) and the solution was washed with a saturated solution of NaHCO$_3$ (3×500 mL), dried over Na$_2$SO$_4$, filtered and evaporated to dryness. The resulting white foam was triturated in diethyl ether to afford compound 79 as a white solid (3.2 g; yield=57%).

Synthesis of Compound 80:

To a solution of compound 4c (1.5 g; 7.3 mmol; 1 eq.) in DMSO (11 mL) at room temperature was successively added triethylamine (3.8 mL; 29 mmol; 4 eq.), compound 79 (1.5 g; 8.8 mmol; 1.2 eq.) and TBTU (2.8 g; 8.8 mmol; 1.2 eq.). The reaction mixture became homogeneous for a few minutes prior to the precipitation of a solid. After stirring for 16 hours at room temperature, the precipitate was filtered on a Büchner funnel. The cake was washed with ethyl acetate and dried to afford compound 80 as a yellow solid (1.7 g; yield=64%).

Synthesis of Compound 81:

To a suspension of compound 80 (1.7 g; 4.7 mmol; 1 eq.) in acetonitrile (33 mL) at room temperature was successively added N,N-diisopropylethylamine (4.7 mL; 28.2 mmol; 6 eq.), triphenylphosphine (2.2 g; 8.5 mmol; 1.8 eq.) and hexachloroethane (1.7 g; 7.0 mmol; 1.5 eq.). The reaction mixture became homogeneous for few minutes prior to the precipitation of a solid. After stirring for 16 hours at room temperature, the precipitate was filtered on a Büchner funnel. The cake was washed with diethyl ether to afford compound 81 as a beige solid (1.1 g; yield=71%).

Synthesis of Compound COTI-HIV28233:

To a suspension of compound 81 (236 mg; 700 µmol; 1 eq.) in toluene (3.5 mL) at room temperature was added hydroxylamine hydrochloride (73 mg; 1.05 mmol; 1.5 eq.) and titanium (IV) isopropoxide (310 µL; 1.10 mmol; 1.5 eq.). The reaction mixture was refluxed for 18 hours and evaporated to dryness. The red residue was dissolved in a mixture of a saturated solution of NaHCO$_3$/ethyl acetate/methanol (5:5:1; 55 mL). After separation of the layers, the aqueous phase was extracted with ethyl acetate (3×50 mL). The combined organic phases were washed with brine (100 mL), dried over Na$_2$SO$_4$, filtered and evaporated to dryness. The purification of the residue on silica gel (eluent: dichloromethane/methanol, 100/0 to 98/2) followed by a trituration in methanol afforded compound COTI-HIV28233 as an yellow solid (39 mg; yield=16%). $^1$H NMR (CDCl$_3$, ppm): 3.71 (s, 3H); 4.27 (s, 2H); 7.00 (m, 2H); 7.35 (m, 3H); 7.52 (m, 1H), 8.22 (m, 1H), 15.23 (m, NOH). MS (ES+IC): m/z (M+H)$^+$353.

Example 4

Synthesis of COTI-HIV28236-SA

Synthesis of the compound of COTI-HIV28236-SA can be conducted according to the following synthetic methodology:

Synthesis of Compound 78:

To a solution of compound 77 (5.0 g; 33 mmol; 1 eq.) in dichloromethane (100 mL) at room temperature was successively added triethylamine (13.0 mL; 100 mmol; 3 eq.), tert-butylcarbazate (4.8 g; 36 mmol; 1.1 eq.), EDCI (6.9 g; 36 mmol; 1.1 eq.) and HOBt (445 mg; 3.3 mmol; 0.1 eq.). After stirring the mixture for 18 hours at room temperature, the reaction was quenched by addition of a saturated solution of NH$_4$Cl (200 mL). The layers were separated and the aqueous phase was extracted with dichloromethane (3×200 mL). The combined organic phases were dried over Na$_2$SO$_4$, filtered and evaporated to dryness to afford compound 78 as a colourless oil (9.1 g; yield=100%).

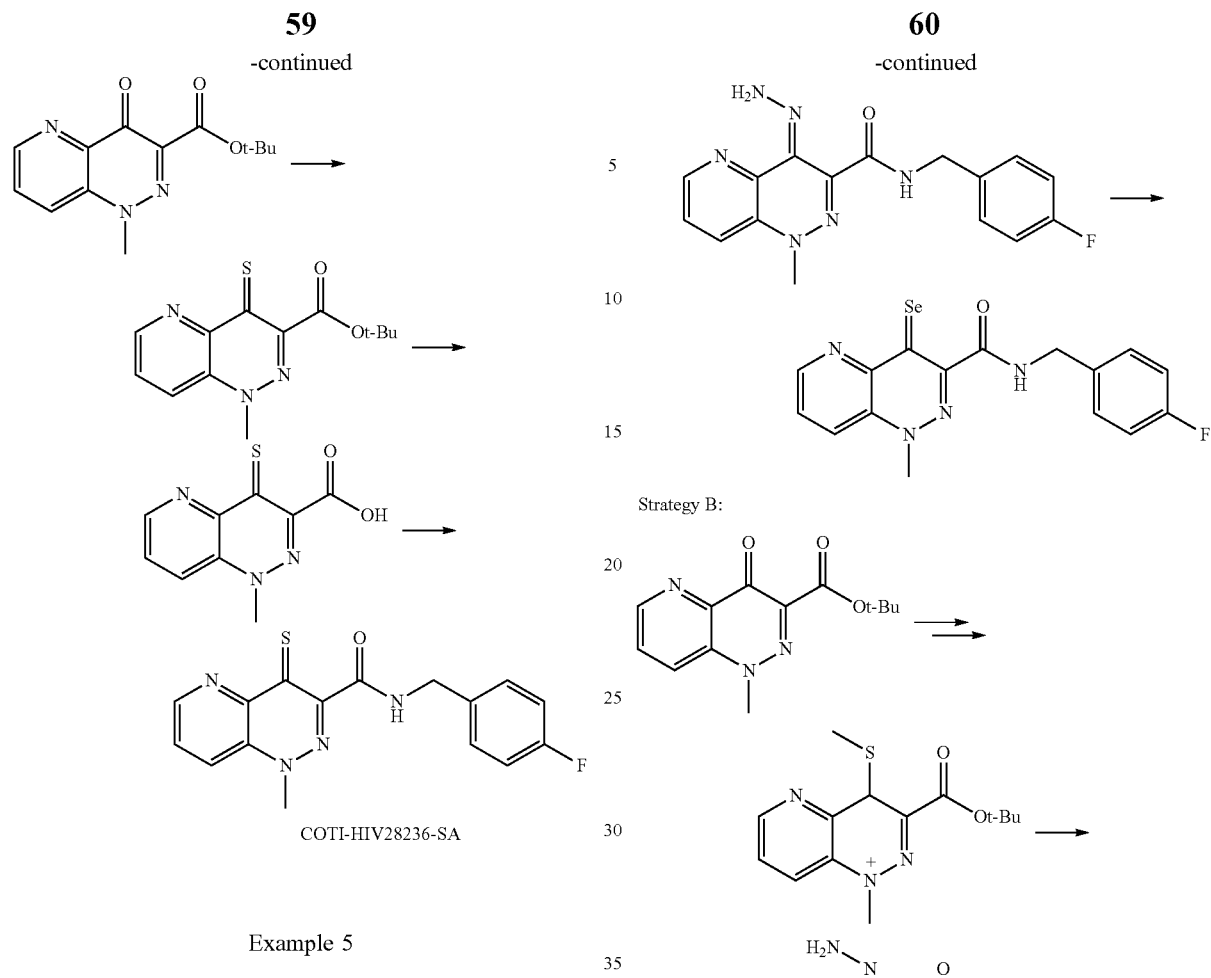
-continued
COTI-HIV28236-SA
Example 5
Synthesis of COTI-HIV28236-SeA
Synthesis of the compound of COTI-HIV28236-SeA can be conducted according to the following synthetic methodology:
Strategy A:
-continued
Strategy B:
Strategy C:

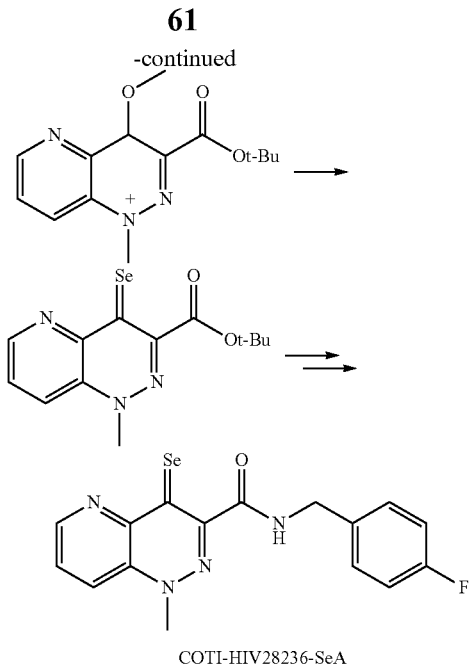

COTI-HIV28236-SeA

Example 6

Computational Assessment of Properties

A computational assessment of the properties of compounds according to the present invention was performed using the CHEMSAS® computational platform. CHEMSAS® is a robust proprietary computational platform for accelerated drug discovery, optimization and lead selection based upon a unique combination of traditional and modern pharmacology principles, statistical modeling and machine learning technologies. At the centre of the CHEMSAS® platform is a hybrid machine learning technology that may be used to: find, profile and optimize new targeted lead compounds; find novel uses for known compounds; and, solve problems with existing or potential drugs. In using the CHEMSAS® platform, first a therapeutic target was selected, in this case HIV and more particularly the critical enzyme HIV integrase. The second step involved the design of a candidate molecule library containing thousands of potential compounds through the assembly of privileged molecular fragments. Thirdly, the candidate library was profiled and optimized using a combination of validated computational models and traditional expert medicinal chemistry. In this step, the CHEMSAS® platform developed about 315 molecular descriptors for each candidate therapeutic compound. For example, molecular properties relating to a candidate compound's therapeutic efficacy, expected human toxicity, oral absorption, cumulative cellular resistance and/or kinetics were assessed. In some instances, comparative properties relating to commercially relevant benchmark compounds were also assessed. Potential lead compounds were then selected from the candidate library using a proprietary decision making tool designed to identify candidates with the optimal physical chemical properties, efficacy, ADME/Toxicity profile, etc. according to a predetermined set of design criteria. The lead compounds selected from the candidate library were then synthesized for further pre-clinical development.

The properties of certain compounds according to the present invention, specifically, those indicated in Tables 1-8 that were assessed using the CHEMSAS® computational platform are shown below. Some of the predicted properties are validated by the experimental data provided herein, while other properties have been validated elsewhere during the development of other clinical candidates. The CHEMSAS® platform therefore provides a means of determining, predicting and/or testing the properties of a compound, particularly when used to determine the properties of compounds according to the present invention. The CHEMSAS® platform is also particularly useful in comparing the properties of compounds according to the invention with prior art compounds on a relative basis in silico.

Tables 1A and 1B: Physical Chemical Properties

Tables 1A and 1B shows that the compounds are all "drug-like" with good drug like physical properties.

TABLE 1A

| MolID | Formula | MolWt | ALogP | HBndAcc |
|---|---|---|---|---|
| COTI-HIV1oxo | C17H12FN5O2 | 337.31 | 2.45 | 7 |
| COTI-HIV1thio | C17H12FN5OS | 353.38 | 3.35 | 6 |
| COTI-HIV1Se | C17H12FN5OSe | 400.27 | 2.48 | 6 |
| COTI-HIV1imine | C17H13FN6O | 336.33 | 2.51 | 7 |
| COTI-HIV1Oxime | C17H13FN6O2 | 352.33 | 2.54 | 8 |
| COTI-HIV2oxo | C16H13FN4O2 | 312.30 | 1.98 | 6 |
| COTI-HIV28236-SA | C16H13FN4OS | 328.37 | 2.88 | 5 |
| COTI-HIV28236-SeA | C16H13FN4OSe | 375.26 | 2.00 | 5 |
| COTI-HIV2imine | C16H14FN5O | 311.32 | 2.03 | 6 |
| COTI-HIV28236 | C16H14FN5O2 | 327.32 | 2.06 | 7 |
| COTI-HIV1DOxime | C14H12FN5O3 | 317.28 | 1.15 | 8 |
| COTI-HIV1Doxo | C14H11FN4O3 | 302.26 | 0.54 | 7 |
| COTI-HIV1Dthio | C14H11FN4O2S | 318.33 | 1.96 | 6 |
| COTI-HIV1Dcyano | C15H11FN6O2 | 326.29 | 1.35 | 8 |
| COTI-HIV1Dimino | C14H12FN5O2 | 301.28 | 1.12 | 7 |
| COTI-HIV2DOxime | C13H13FN4O3 | 292.27 | 0.68 | 7 |
| COTI-HIV2Doxo | C13H12FN3O3 | 277.25 | 0.07 | 6 |
| COTI-HIV2Dthio | C13H12FN3O2S | 293.32 | 1.49 | 5 |
| COTI-HIV2Dcyano | C14H12FN5O2 | 301.28 | 0.89 | 7 |
| COTI-HIV2Dimino | C13H13FN4O2 | 276.27 | 0.65 | 6 |

TABLE 1B

| MolID | Formula | HBndDon | RotBnds | TPSA |
|---|---|---|---|---|
| COTI-HIV1oxo | C17H12FN5O2 | 0 | 3 | 78.31 |
| COTI-HIV1thio | C17H12FN5OS | 0 | 3 | 61.01 |
| COTI-HIV1Se | C17H12FN5OSe | 0 | 3 | 61.01 |
| COTI-HIV1imine | C17H13FN6O | 1 | 3 | 84.10 |
| COTI-HIV1Oxime | C17H13FN6O2 | 1 | 4 | 93.15 |
| COTI-HIV2oxo | C16H13FN4O2 | 1 | 4 | 73.35 |
| COTI-HIV28236-SA | C16H13FN4OS | 1 | 4 | 56.05 |
| COTI-HIV28236-SeA | C16H13FN4OSe | 1 | 4 | 56.05 |
| COTI-HIV2imine | C16H14FN5O | 2 | 4 | 79.14 |
| COTI-HIV28236 | C16H14FN5O2 | 2 | 5 | 88.19 |
| COTI-HIV1DOxime | C14H12FN5O3 | 2 | 5 | 102.71 |
| COTI-HIV1Doxo | C14H11FN4O3 | 1 | 4 | 87.87 |
| COTI-HIV1Dthio | C14H11FN4O2S | 1 | 4 | 70.57 |
| COTI-HIV1Dcyano | C15H11FN6O2 | 1 | 5 | 104.83 |
| COTI-HIV1Dimino | C14H12FN5O2 | 2 | 4 | 93.66 |
| COTI-HIV2DOxime | C13H13FN4O3 | 3 | 6 | 97.74 |
| COTI-HIV2Doxo | C13H12FN3O3 | 2 | 5 | 82.90 |
| COTI-HIV2Dthio | C13H12FN3O2S | 2 | 5 | 65.60 |
| COTI-HIV2Dcyano | C14H12FN5O2 | 2 | 6 | 99.86 |
| COTI-HIV2Dimino | C13H13FN4O2 | 3 | 5 | 88.69 |

Legend for Table 1:
MolWt stands for Molecular Weight measured in Daltons and is a size descriptor;
A Log P is calculated lipophilicity/solubility estimates;
HBndDon stands for Hydrogen Bond Donor and refers to the number of atoms able to donate electrons to potentially form Hydrogen bonds;

HBndAcc stands for Hydrogen Bond Acceptor and refers to the number of atoms able to accept electrons to potentially form Hydrogen bonds;
TPSA stands for Topological Polar Surface Area and is a measure of Molecular Surface Charge/Polarity; and
RotBnds stands for Rotatable Bonds which is a count of freely rotatable single bonds in the molecule.

Table 2: Solubility Properties
Table 2 shows that all of the compounds are expected to have acceptable solubility values for drug-like compounds.

TABLE 2A

| MolID | Formula | LogD(pH 7.4) | LogSw |
|---|---|---|---|
| COTI-HIV1oxo | C17H12FN5O2 | 2.52 | −3.94 |
| COTI-HIV1thio | C17H12FN5OS | 2.60 | −4.35 |
| COTI-HIV1Se | C17H12FN5OSe | 2.15 | −4.22 |
| COTI-HIV1imine | C17H13FN6O | 1.79 | −3.89 |
| COTI-HIV1Oxime | C17H13FN6O2 | 2.03 | −3.94 |
| COTI-HIV2oxo | C16H13FN4O2 | 2.66 | −3.46 |
| COTI-HIV28236-SA | C16H13FN4OS | 2.87 | −3.65 |
| COTI-HIV28236-SeA | C16H13FN4OSe | 1.97 | −3.55 |
| COTI-HIV2imine | C16H14FN5O | 2.00 | −3.52 |
| COTI-HIV28236 | C16H14FN5O2 | 1.93 | −3.42 |
| COTI-HIV1DOxime | C14H12FN5O3 | 1.47 | −3.44 |
| COTI-HIV1Doxo | C14H11FN4O3 | 1.57 | −3.19 |
| COTI-HIV1Dthio | C14H11FN4O2S | 1.84 | −3.75 |
| COTI-HIV1Dcyano | C15H11FN6O2 | 1.58 | −3.71 |
| COTI-HIV1Dimino | C14H12FN5O2 | 0.15 | −3.36 |
| COTI-HIV2DOxime | C13H13FN4O3 | 1.76 | −2.63 |
| COTI-HIV2Doxo | C13H12FN3O3 | 0.54 | −2.45 |
| COTI-HIV2Dthio | C13H12FN3O2S | 1.17 | −3.04 |
| COTI-HIV2Dcyano | C14H12FN5O2 | 1.88 | −2.73 |
| COTI-HIV2Dimino | C13H13FN4O2 | −1.05 | −2.59 |

Legend for Table 2:
Log D(7.4) is a measure of relative solubility in octanol vs water at a specific pH, in this case pH=7.4; and
Log Sw is the logarithm of the calculated solubility in pure water usually measured at 25° C.

Table 3: Efficacy (Log IC50)
Referring to Table 3, compounds with a high value for Prob_Log IC50<−6 (meaning a value that is greater than 0.70, preferably greater than 0.80, more preferably greater than 0.90) are predicted to have a high likelihood of sub-micromolar activity against HIV Integrase. Similarly, Prob_Log IC50<−7 represents the probability that the IC50 is less than or equal to 100 nM. In-silico comparative data is also shown for compounds described in PCT Publication No. WO2003/062204: Compound A; PCT Publication No. WO 2004/101512: Compound B; and Laquinimod™. These compounds are as follows:

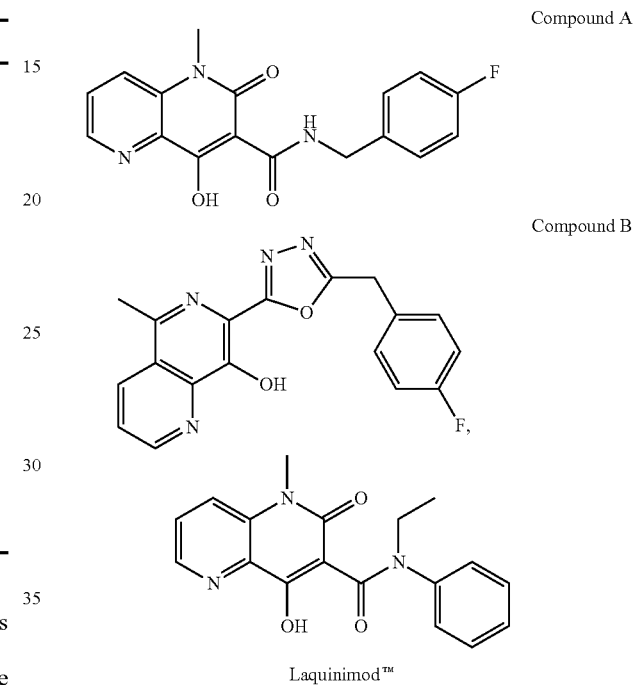

Compound A

Compound B

Laquinimod™

TABLE 3

| MolID | Formula | Prob_LogIC50 <− 6 | Prob_LogIC50 <− 7 |
|---|---|---|---|
| COTI-HIV1oxo | C17H12FN5O2 | 0.911 | 0.000 |
| COTI-HIV1thio | C17H12FN5OS | 0.202 | 0.000 |
| COTI-HIV1Se | C17H12FN5OSe | 0.000 | 0.000 |
| COTI-HIV1imine | C17H13FN6O | 0.944 | 0.934 |
| COTI-HIV1Oxime | C17H13FN6O2 | 0.935 | 0.912 |
| COTI-HIV2oxo | C16H13FN4O2 | 0.986 | 0.000 |
| COTI-HIV28236-SA | C16H13FN4OS | 0.018 | 0.000 |
| COTI-HIV28236-SeA | C16H13FN4OSe | 0.000 | 0.000 |
| COTI-HIV2imine | C16H14FN5O | 0.938 | 0.000 |
| COTI-HIV28236 | C16H14FN5O2 | 0.965 | 0.973 |
| COTI-HIV1DOxime | C14H12FN5O3 | 0.989 | 0.947 |
| COTI-HIV1Doxo | C14H11FN4O3 | 0.996 | 0.957 |
| COTI-HIV1Dthio | C14H11FN4O2S | 0.776 | 0.000 |
| COTI-HIV1Dcyano | C15H11FN6O2 | 0.829 | 0.011 |
| COTI-HIV1Dimino | C14H12FN5O2 | 0.979 | 0.895 |
| COTI-HIV2DOxime | C13H13FN4O3 | 0.996 | 0.581 |
| COTI-HIV2Doxo | C13H12FN3O3 | 0.995 | 0.994 |
| COTI-HIV2Dthio | C13H12FN3O2S | 0.203 | 0.000 |
| COTI-HIV2Dcyano | C14H12FN5O2 | 0.980 | 0.001 |
| COTI-HIV2Dimino | C13H13FN4O2 | 0.985 | 0.955 |
| Compound A | C17H14N3O3 | 0.999 | 0.996 |
| Compound B | C18H13FN4O2 | 0.946 | 0.076 |
| Laquinimod ™ | C18H17N3O3 | 0.897 | 0.000 |

Legend for Table 3:

Prob_Log IC50<−6 is the probability that the IC50 value of the compound (i.e. the amount required to reduce the initial concentration by 50%) will be less than $10^{-6}$ (i.e. sub-micromolar activity against the chosen target).

Prob_Log IC50<−7 is the probability that the IC50 value of the compound (i.e. the amount required to reduce the initial concentration by 50%) will be less than $10^{-7}$ (i.e. less than or equal to 100 nM activity against the chosen target).

Tables 4A and 4B: Oral Absorption and BBB Penetration

Referring to Tables 4A and 4B, compounds with a high P_OrlAvail>30% are likely to have acceptable oral absorption. Compounds with a high P_Clr<30 ml/min/kg are expected to have an acceptable clearance rate and are therefore expected to remain in circulation longer than those with a low P_Clr<30 ml/min/kg. All compounds were predicted to be acceptable in both attributes. EST_PPB % is the estimated percentage plasma protein binding of the compound. Estimates of greater than 95% plasma protein binding would be considered to be highly protein bound. P_BBBPenetration is an estimate of the probability that the drug will penetrate the blood brain barrier and enter the central nervous system (CNS). Predicted values of greater than 0.7 P_ indicate that the drug is likely to pass the blood brain barrier and enter the central nervous system (CNS).

TABLE 4A

| MolID | Formula | P_OrlAvail > 30% | P_Clr < 30 ml/min/kg |
|---|---|---|---|
| COTI-HIV1oxo | C17H12FN5O2 | 0.970 | 0.961 |
| COTI-HIV1thio | C17H12FN5OS | 0.954 | 0.925 |
| COTI-HIV1Se | C17H12FN5OSe | 0.980 | 0.906 |
| COTI-HIV1imine | C17H13FN6O | 0.970 | 0.934 |
| COTI-HIV1Oxime | C17H13FN6O2 | 0.933 | 0.917 |
| COTI-HIV2oxo | C16H13FN4O2 | 0.971 | 0.981 |
| COTI-HIV28236-SA | C16H13FN4OS | 0.968 | 0.980 |
| COTI-HIV28236-SeA | C16H13FN4OSe | 0.975 | 0.980 |
| COTI-HIV2imine | C16H14FN5O | 0.973 | 0.967 |
| COTI-HIV28236 | C16H14FN5O2 | 0.966 | 0.957 |
| COTI-HIV1DOxime | C14H12FN5O3 | 0.992 | 0.966 |
| COTI-HIV1Doxo | C14H11FN4O3 | 0.992 | 0.984 |
| COTI-HIV1Dthio | C14H11FN4O2S | 0.993 | 0.984 |
| COTI-HIV1Dcyano | C15H11FN6O2 | 0.992 | 0.928 |
| COTI-HIV1Dimino | C14H12FN5O2 | 0.992 | 0.966 |
| COTI-HIV2DOxime | C13H13FN4O3 | 0.950 | 0.976 |
| COTI-HIV2Doxo | C13H12FN3O3 | 0.940 | 0.994 |
| COTI-HIV2Dthio | C13H12FN3O2S | 0.959 | 0.994 |
| COTI-HIV2Dcyano | C14H12FN5O2 | 0.960 | 0.952 |
| COTI-HIV2Dimino | C13H13FN4O2 | 0.955 | 0.986 |

TABLE 4B

| MolID | Formula | EST_PPB % | P_BBBPenetration |
|---|---|---|---|
| COTI-HIV1oxo | C17H12FN5O2 | 94.10 | 0.605 |
| COTI-HIV1thio | C17H12FN5OS | 95.83 | 0.817 |
| COTI-HIV1Se | C17H12FN5OSe | 95.42 | 0.863 |
| COTI-HIV1imine | C17H13FN6O | 86.83 | 0.777 |
| COTI-HIV1Oxime | C17H13FN6O2 | 93.92 | 0.640 |
| COTI-HIV2oxo | C16H13FN4O2 | 48.00 | 0.694 |
| COTI-HIV28236-SA | C16H13FN4OS | 89.71 | 0.887 |
| COTI-HIV28236-SeA | C16H13FN4OSe | 86.05 | 0.984 |
| COTI-HIV2imine | C16H14FN5O | 50.21 | 0.713 |
| COTI-HIV28236 | C16H14FN5O2 | 51.05 | 0.275 |
| COTI-HIV1DOxime | C14H12FN5O3 | 94.53 | 0.927 |
| COTI-HIV1Doxo | C14H11FN4O3 | 65.97 | 0.966 |
| COTI-HIV1Dthio | C14H11FN4O2S | 94.37 | 0.842 |
| COTI-HIV1Dcyano | C15H11FN6O2 | 93.61 | 0.946 |
| COTI-HIV1Dimino | C14H12FN5O2 | 91.38 | 0.971 |
| COTI-HIV2DOxime | C13H13FN4O3 | 53.38 | 0.928 |
| COTI-HIV2Doxo | C13H12FN3O3 | 50.40 | 0.920 |
| COTI-HIV2Dthio | C13H12FN3O2S | 71.37 | 0.134 |
| COTI-HIV2Dcyano | C14H12FN5O2 | 58.95 | 0.915 |
| COTI-HIV2Dimino | C13H13FN4O2 | 50.41 | 0.895 |

Legend for Table 4:

P_OrlAvail>30% is the probability that the oral availability of the compound will be greater than 30%.

P_Clr<30 ml/min/kg is the probability that the compound will be cleared from circulation at a rate of less than 30 ml/min/kg.

EST_PPB % is the estimated percentage plasma protein binding of the compound.

P_BBBPenetration is an estimate of the probability that the drug will penetrate the blood brain barrier and enter the central nervous system (CNS).

TABLE 5

Metabolic Stability (Percent remaining at 60 minutes and calculated half life in hours)

| MolID | Formula | Est_T½(Hrs) |
|---|---|---|
| COTI-HIV1oxo | C17H12FN5O2 | 12.5 |
| COTI-HIV1thio | C17H12FN5OS | 12.1 |
| COTI-HIV1Se | C17H12FN5OSe | 14.5 |
| COTI-HIV1imine | C17H13FN6O | 16.0 |
| COTI-HIV1Oxime | C17H13FN6O2 | 13.3 |
| COTI-HIV2oxo | C16H13FN4O2 | 5.6 |
| COTI-HIV28236-SA | C16H13FN4OS | 8.2 |
| COTI-HIV28236-SeA | C16H13FN4OSe | 7.2 |
| COTI-HIV2imine | C16H14FN5O | 6.4 |
| COTI-HIV28236 | C16H14FN5O2 | 6.1 |
| COTI-HIV1DOxime | C14H12FN5O3 | 8.5 |
| COTI-HIV1Doxo | C14H11FN4O3 | 7.0 |
| COTI-HIV1Dthio | C14H11FN4O2S | 12.8 |
| COTI-HIV1Dcyano | C15H11FN6O2 | 16.5 |
| COTI-HIV1Dimino | C14H12FN5O2 | 8.2 |
| COTI-HIV2DOxime | C13H13FN4O3 | 7.0 |
| COTI-HIV2Doxo | C13H12FN3O3 | 6.0 |
| COTI-HIV2Dthio | C13H12FN3O2S | 6.7 |
| COTI-HIV2Dcyano | C14H12FN5O2 | 8.4 |
| COTI-HIV2Dimino | C13H13FN4O2 | 6.7 |

Table 5 shows that in vitro metabolic stability is expected to be adequate for all compounds. The compounds with a high Est_T½ (Hrs) are expected to take longer to be reduced to one half of their initial concentration than those with a low Est_T½ (Hrs). All predicted half lives were considered to be acceptable.

Legend for Table 5:

Est_T½ (hrs) is a calculated estimate of the half life of the drug measured in hours.

TABLE 6

Probability of Toxicity

| MolID | Formula | AcuteLD50 (oral) | HepToxProb |
|---|---|---|---|
| COTI-HIV1oxo | C17H12FN5O2 | 698.32 | 0.131 |
| COTI-HIV1thio | C17H12FN5OS | 1063.08 | 0.109 |
| COTI-HIV1Se | C17H12FN5OSe | 760.55 | 0.155 |

TABLE 6-continued

Probability of Toxicity

| MolID | Formula | AcuteLD50 (oral) | HepToxProb |
|---|---|---|---|
| COTI-HIV1imine | C17H13FN6O | 682.51 | 0.106 |
| COTI-HIV1Oxime | C17H13FN6O2 | 790.04 | 0.077 |
| COTI-HIV2oxo | C16H13FN4O2 | 1276.26 | 0.022 |
| COTI-HIV28236-SA | C16H13FN4OS | 1157.14 | 0.028 |
| COTI-HIV28236-SeA | C16H13FN4OSe | 839.67 | 0.023 |
| COTI-HIV2imine | C16H14FN5O | 1101.07 | 0.033 |
| COTI-HIV28236 | C16H14FN5O2 | 2362.44 | 0.070 |
| COTI-HIV1DOxime | C14H12FN5O3 | 1226.94 | 0.147 |
| COTI-HIV1Doxo | C14H11FN4O3 | 1805.56 | 0.059 |
| COTI-HIV1Dthio | C14H11FN4O2S | 1256.64 | 0.091 |
| COTI-HIV1Dcyano | C15H11FN6O2 | 1148.98 | 0.311 |
| COTI-HIV1Dimino | C14H12FN5O2 | 1356.28 | 0.048 |
| COTI-HIV2DOxime | C13H13FN4O3 | 1985.67 | 0.017 |
| COTI-HIV2Doxo | C13H12FN3O3 | 658.87 | 0.322 |
| COTI-HIV2Dthio | C13H12FN3O2S | 953.29 | 0.040 |
| COTI-HIV2Dcyano | C14H12FN5O2 | 1417.21 | 0.115 |
| COTI-HIV2Dimino | C13H13FN4O2 | 1202.51 | 0.011 |

The low values provided in Table 6 for HepToxProb show that none of the compounds are expected to cause any Hepatic Toxicity. The compounds with a low AcuteLD50 (oral) are potentially more toxic than those with a high AcuteLD50 (oral). It takes more of a compound with a high AcuteLD50 (oral) to cause death in 50% of the rats to which it is administered, therefore such compounds are less toxic than those with a low AcuteLD50 (oral). Compounds with an LD50 of greater than 500 mg/kg are predicted to have acceptable toxicity for further development.

Legend for Table 6:

AcuteLD50 (oral) is the calculated point estimate of the dose of the drug in mg/kg that would cause death in 50% of healthy test lab rats when the drug is given orally.

HepToxProb is the average calculated probability from an ensemble of models that the drug in question will cause any liver toxicity.

TABLE 7

Animal and Human Toxicity Predictions

| MolID | Formula | hMRTD (mg/kg/day) | VentTach | hERG (IC50 > 10 umol) |
|---|---|---|---|---|
| COTI-HIV1oxo | C17H12FN5O2 | 1.29 | 0.018 | 0.934 |
| COTI-HIV1thio | C17H12FN5OS | 0.87 | 0.469 | 0.907 |
| COTI-HIV1Se | C17H12FN5OSe | 1.23 | 0.526 | 0.771 |
| COTI-HIV1imine | C17H13FN6O | 1.18 | 0.008 | 0.835 |
| COTI-HIV1Oxime | C17H13FN6O2 | 1.64 | 0.012 | 0.814 |
| COTI-HIV2oxo | C16H13FN4O2 | 1.85 | 0.013 | 0.988 |
| COTI-HIV28236-SA | C16H13FN4OS | 2.46 | 0.086 | 0.932 |
| COTI-HIV28236-SeA | C16H13FN4OSe | 2.16 | 0.040 | 0.896 |
| COTI-HIV2imine | C16H14FN5O | 1.56 | 0.031 | 0.959 |
| COTI-HIV28236 | C16H14FN5O2 | 2.15 | 0.009 | 0.969 |
| COTI-HIV1DOxime | C14H12FN5O3 | 7.62 | 0.002 | 0.978 |
| COTI-HIV1Doxo | C14H11FN4O3 | 7.81 | 0.003 | 0.993 |
| COTI-HIV1Dthio | C14H11FN4O2S | 1.01 | 0.007 | 0.981 |
| COTI-HIV1Dcyano | C15H11FN6O2 | 4.01 | 0.009 | 0.928 |
| COTI-HIV1Dimino | C14H12FN5O2 | 5.04 | 0.006 | 0.987 |
| COTI-HIV2DOxime | C13H13FN4O3 | 14.49 | 0.003 | 0.998 |
| COTI-HIV2Doxo | C13H12FN3O3 | 12.39 | 0.002 | 1.000 |
| COTI-HIV2Dthio | C13H12FN3O2S | 7.62 | 0.007 | 0.995 |
| COTI-HIV2Dcyano | C14H12FN5O2 | 6.34 | 0.009 | 0.994 |
| COTI-HIV2Dimino | C13H13FN4O2 | 7.15 | 0.003 | 0.998 |

The expected maximum recommended therapeutic daily dose in humans is provided in the column labeled hMRTD and is measured in mg/kg/d. hERG (IC50>10 umol) is the probability that the IC50 value (i.e. the amount required to produce a 50% decrease in initial concentration) for hERG will be greater than 10 umol. A high value indicates that it is likely that the compound will have little hERG channel activity. All of the compounds met the acceptance criterion of the probability being greater than 0.70. A high predicted hERG 1050 value is associated with a low probability of ventricular tachycardia (VentTach).

Legend for Table 7:

hMRTD is the calculated maximum recommended therapeutic daily dose of the drug in milligrams per kg per day for the average 60 Kg human adult; VentTach is the probability that the drug would produce ventricular trachycardia, which is a potentially lethal cardiac rhythm disturbance. hERG (IC50>10 umol) is the probability that the IC50 value (i.e. the amount required to produce a 50% decrease in initial concentration) for hERG will be greater than 10 umol. A high value indicates that it is likely that the compound will have little activity against hERG.

TABLE 8

Predicted Bio-pharmaceutical Classification (BCS)

| MolID | Formula | P_Class 1 | P_Class 2 | P_Class 3 | P_Class 4 |
|---|---|---|---|---|---|
| COTI-HIV1oxo | C17H12FN5O2 | 0.000 | 0.994 | 0.000 | 0.005 |
| COTI-HIV1thio | C17H12FN5OS | 0.010 | 0.983 | 0.000 | 0.006 |
| COTI-HIV1Se | C17H12FN5OSe | 0.000 | 0.993 | 0.000 | 0.006 |
| COTI-HIV1imine | C17H13FN6O | 0.005 | 0.986 | 0.000 | 0.009 |
| COTI-HIV1Oxime | C17H13FN6O2 | 0.008 | 0.983 | 0.000 | 0.009 |
| COTI-HIV2oxo | C16H13FN4O2 | 0.000 | 0.079 | 0.000 | 0.921 |
| COTI-HIV28236-SA | C16H13FN4OS | 0.000 | 0.741 | 0.000 | 0.259 |
| COTI-HIV28236-SeA | C16H13FN4OSe | 0.010 | 0.537 | 0.008 | 0.445 |
| COTI-HIV2imine | C16H14FN5O | 0.001 | 0.316 | 0.003 | 0.680 |
| COTI-HIV28236 | C16H14FN5O2 | 0.000 | 0.831 | 0.000 | 0.169 |
| COTI-HIV1DOxime | C14H12FN5O3 | 0.000 | 0.197 | 0.000 | 0.803 |

TABLE 8-continued

Predicted Bio-pharmaceutical Classification (BCS)

| MolID | Formula | P_Class 1 | P_Class 2 | P_Class 3 | P_Class 4 |
|---|---|---|---|---|---|
| COTI-HIV1Doxo | C14H11FN4O3 | 0.000 | 0.523 | 0.000 | 0.476 |
| COTI-HIV1Dthio | C14H11FN4O2S | 0.000 | 0.995 | 0.000 | 0.004 |
| COTI-HIV1Dcyano | C15H11FN6O2 | 0.003 | 0.991 | 0.000 | 0.007 |
| COTI-HIV1Dimino | C14H12FN5O2 | 0.000 | 0.656 | 0.000 | 0.343 |
| COTI-HIV2DOxime | C13H13FN4O3 | 0.004 | 0.838 | 0.001 | 0.157 |
| COTI-HIV2Doxo | C13H12FN3O3 | 0.001 | 0.710 | 0.000 | 0.288 |
| COTI-HIV2Dthio | C13H12FN3O2S | 0.000 | 0.255 | 0.001 | 0.744 |
| COTI-HIV2Dcyano | C14H12FN5O2 | 0.003 | 0.774 | 0.001 | 0.222 |
| COTI-HIV2Dimino | C13H13FN4O2 | 0.002 | 0.817 | 0.001 | 0.180 |

Table 8 shows the predicted BCS for all of the structures. Referring to the Legend below, the probability of belonging to a given BCS class is provided. The majority of the compounds are predicted to be in Class 2. This implies that the compounds are predicted to have good permeability and low solubility and provides guidance for formulation and further development.

Legend for Table 8:

P_Class 1 is the probability that the compound would be in BCS Class 1 and have a high solubility and a high permeability.

P_Class 2 is the probability that the compound would be in BCS Class 2 and have a low solubility and a high permeability.

P_Class 3 is the probability that the compound would be in BCS Class 3 and have a high solubility and a low permeability.

P_Class 4 is the probability that the compound would be in BCS Class 4 and have a low solubility and a low permeability.

Example 7

HIV Integrase Assay In Vitro

The purpose of this study was to analyze the capacity of the COTI-HIV1Doxo (a COTI-HIV1 Ketone Derivative) to inhibit HIV-1 integrase in an in vitro assay. It should be noted that this compound is a precursor to all of the COTI-HIV1D-structures. The structure of COTI-HIV1Doxo is shown below:

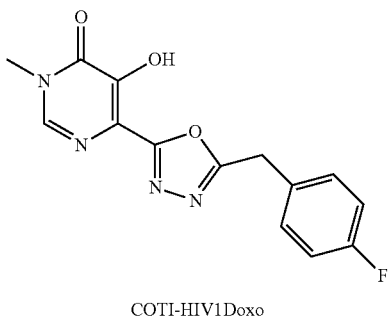 [SMILES: Cn1cnc(-c2nnc(Cc3ccc(F)cc3)o2)c(O)c1=O]

COTI-HIV1Doxo

Methods:

The capacity of the compound to inhibit HIV integrase in a cell-free system was assessed. An HIV Integrase Assay System (XpressBio Life Science Products; Thurmont, Md., www.expressbio.com) was used. In brief, double-stranded HIV-1 donor substrate (the U5 long terminal repeat) was immobilized in 96-well plates. Recombinant HIV-1 integrase protein was added, along with an oligonucleotide target substrate. The integrase cleaves the donor substrate and integrates it into the target substrate, which is now in solution phase—the integrated product (the amount is indicative of integrase activity) was detected using an antibody specific for the recombinant target/donor sequence. Inhibitors added along with the donor substrate reduced the amount of product. The degree of inhibition by the compound at each concentration tested (from 1 nM to 100 µM) was determined and, if sufficient inhibition was achieved, an IC50 of the inhibitor was determined. The capacity of a compound known to inhibit HIV integrase activity (NaN3) was assessed as a positive control. All assessed inhibitions were compared to controls treated with vehicle only (compounds dissolved in 100% DMSO, then diluted in buffer to a maximum DMSO concentration of 0.1% DMSO). Concentrations of DMSO up to 5% have no significant effect on HIV integrase activity.

An advantage of the assay is that the capacity of a test compound to directly inhibit HIV integrase can be determined, without complications arising from the effects of the test compound on cell viability that are a complicating factor when testing effects on integration in living cells. However, it should be kept in mind that indirect HIV integrase inhibition (which might possibly occur in living cells) will not be detected.

Results and Discussion:

COTI-HIV1Doxo was assayed for HIV-1 integrase activity, as described above. All measurements were made in quadruplicate (n=4) to allow statistical analysis of significance. $NaN_3$ (1.0% or 3.3%), a known HIV-1 integrase inhibitor, effectively decreased HIV-1 integrase activity in vitro, indicating the reliability of the assay (FIG. 1). COTI-HIV1Doxo inhibited HIV-1 integrase at a concentration of 100 nM (p<0.001, Student's t-test) but not at 10 nM (Rank Sum Test, p=1.000, performed after failure of an equal variance test on the raw data). All higher tested compound concentrations (up to 100 µM) significantly decreased HIV-1 integrase activity (p<0.001 in all cases). Interestingly, a low concentration of COTI-HIV-1 ketone derivative (1 nM) enhanced HIV-1 integrase activity, for unknown reasons (p<0.001).

Overall, COTI-HIV1Doxo appears to be an effective inhibitor of HIV-1 integrase in vitro with capacity to significantly reduce HIV-1 integrase activity at a nanomolar (100 nM) concentration. Complete inhibition of integrase activity was not observed, indicating that increasing COTI-HIV1Doxo concentrations did not reduce integrase function in a linear fashion. In fact, 50% reduction in HIV-1 integrase activity was not achieved until the compound concentrations were in the 10 μM range. Finally, very low concentrations of COTI-HIV-1 ketone derivative (1 nM) slightly but significantly enhanced HIV-1 integrase activity. It did so in a reproducible fashion, in 3 independent experiments. This is consistent with the computational predictions provided for Prob_Log IC50<−6 in Table 3, above.

Example 8

HIV-1 Integrase Assay of COTI-HIV-1, COTI-HIV28233, and COTI-HIV28236

The purpose of this study was to analyze the capacity of COTI-HIV-1 (COTI-HIV1DOxime), COTI-HIV28233 (COTI-HIV1oxime), and COTI-HIV28236, to inhibit HIV-1 integrase in a cell-free/in-vitro assay system.

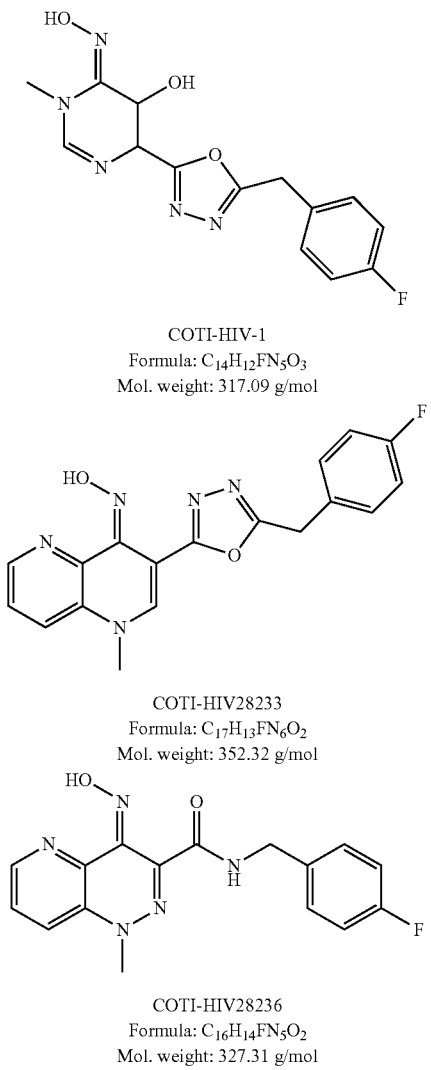

COTI-HIV-1
Formula: $C_{14}H_{12}FN_5O_3$
Mol. weight: 317.09 g/mol

COTI-HIV28233
Formula: $C_{17}H_{13}FN_6O_2$
Mol. weight: 352.32 g/mol

COTI-HIV28236
Formula: $C_{16}H_{14}FN_5O_2$
Mol. weight: 327.31 g/mol

Methods:
Compound Preparation:

COTI-HIV-1 (8 mg; MW: 317.27; Lot # JFM-16-177-FIN) COTI-HIV28233 (8 mg; Lot # ND10/CO04164D) and COTI-HIV28236 (20 mg; MW: 327.31; Lot # ND10/CO04139I) were received at room temperature in lyophilized form. Both compounds were kept in this form at room temperature prior to testing (<1 week).

Test Samples:

Integrase only negative control; No integrase negative control; Sodium azide positive control: a known HIV-1 integrase inhibitor; COTI-HIV-1 (100.000 μM, 10.000 μM, 1.000 μM, 0.100 μM, 0.010 μM, 0.001 μM); COTI-HIV28233 (100.000 μM, 10.000 μM, 1.000 μM, 0.100 μM, 0.010 μM, 0.001 μM); COTI-HIV28236 (100.000 μM, 10.000 μM, 1.000 μM, 0.100 μM, 0.010 μM, 0.001 μM)

HIV-1 Integrase Assay Kit Procedure:

The effect of each compound on HIV integrase activity was assayed using the "HIV-1 Integrase Assay Kit" version 2.0, catalogue number EZ-1700 obtained from XpressBio Life Science Products. Immediately prior to the start of the assay, both compounds were dissolved in dimethyl sulfoxide (DMSO) and used immediately in the HIV integration assay. The assay was performed according to the instructions listed by the manufacturer (XpressBio Life Science Products, Maryland, USA). In brief, the required streptavidin-coated strip wells were coated with DS oligo and placed overnight at 4° C. The plates were then incubated with integrase and followed by the addition of test articles at the desired concentration. The plates were developed using the supplied HRP antibody and TMB peroxidase substrate as per the manufacturer's instructions. The reactions were stopped with TMB stop solution and immediately read (<10 min) using a VICTOR XXX. The absorbance of each well was read at 450 nm for 0.5 sec. All measurements were performed in triplicate. Sodium azide, a known HIV-1 integrase inhibitor, was used as a positive control for inhibiting HIV integrase activity and was found to effectively decrease HIV-1 integrase activity in vitro, indicating the reliability of the assay.

Data Analysis:

The background absorbance was subtracted from the raw data of each sample to yield "background corrected" absorbance values. The mean absorbance of the test samples divided by the mean integrase control activity multiplied by the associated CV yielded the percent adjusted SD. The CV=% SD for the 100% integrase alone control.

Results and Discussion:

To determine the $IC_{50}$ of each test compound, non-linear regression analysis was used. The concentration data (x-axis) was log-transformed (FIG. 2) and analyzed using the equation log(inhibitor) vs. normalized response (Y=100/(1+10^((X−Log $IC_{50}$)))) to determine the $IC_{50}$ (Table 1). Since the data was compared to the integrase alone activity, it was presented as a percent of the control activity. Therefore, the activity observed with the integrase alone control was defined at 100% and the activity observed in the absence of integrase as 0%. Since we have a well-defined 0% and 100% and good control data, the response of the test samples were normalized to run between 0% and 100%.

Figure 2:
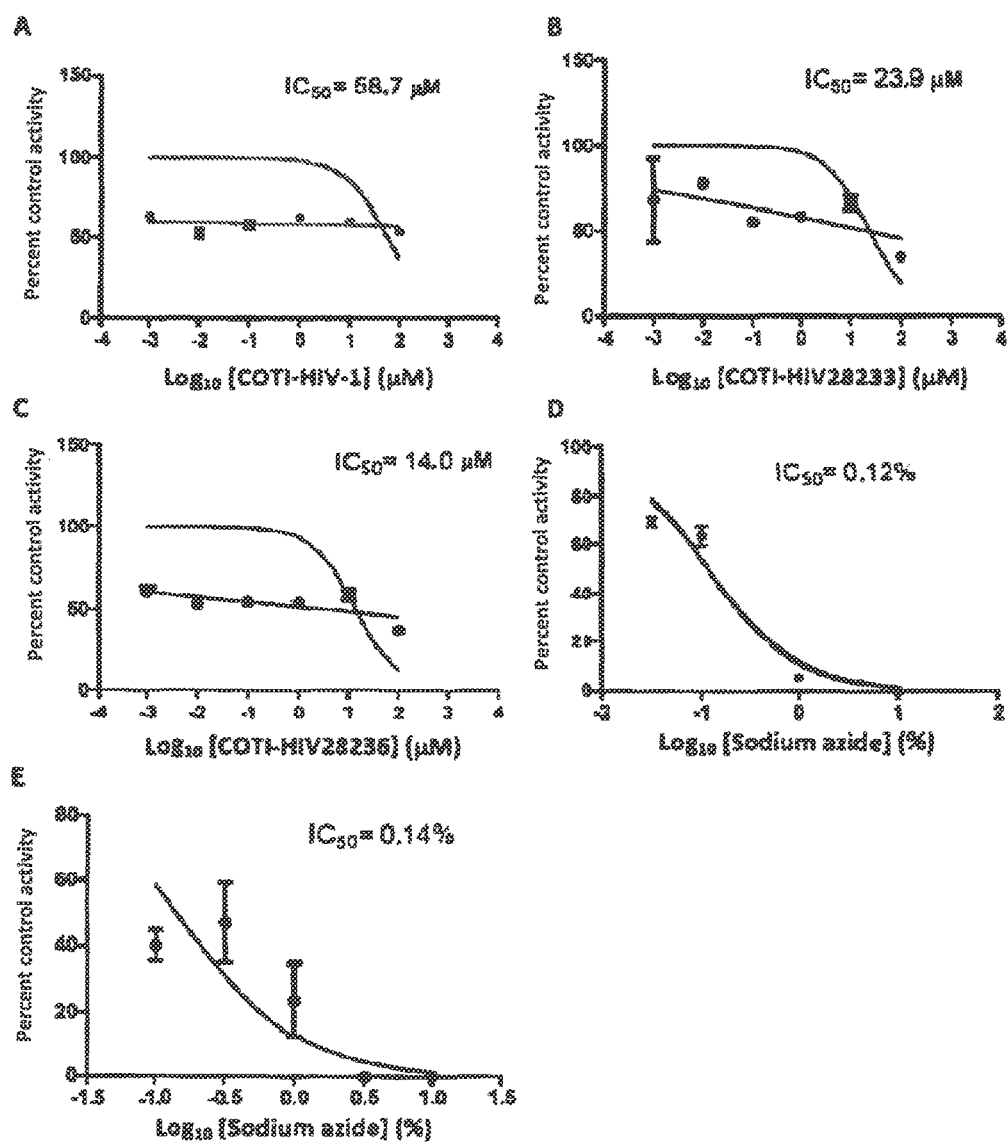
FIG. 2 shows plots of the log-transformation of drug concentrations and best-fit curve for COTI-HIV-1 (A), COTI-HIV28233 (B), COTI-HIV28236 (C), and two sodium azide controls (D & E) to allow calculation of $IC_{50}$ using non-linear regression.

FIGS. 2D and 2E show the results of the sodium azide control, which was run in parallel with the test samples. As observed, in the absence of sodium azide, the percent control activity was 100% and with increasing concentration of sodium azide, the percent control activity decreased, reaching 0% activity with 10% sodium azide. The calculated $IC_{50}$ for both sodium azide controls were similar, 0.12% and 0.14%. The data obtained from all test compounds did not form a full sigmoidal curve reaching 0% control activity (FIG. 2). Because the top and the bottom plateaus can be defined by solid control data (eg. sodium azide), the data was fitted to a normalized model in order to calculate the $IC_{50}$. This model assumes that the dose response curve has a standard slope, equal to a Hill slope of −1.0. Since 6 compound concentrations were tested in triplicate, the data was analyzed using the standard slope model, in contrast with the variable slope model. The $IC_{50}$ values for COTI-HIV-1, COTI-HIV28233 and COTI-HIV28236 were 58.7 µM, 23.9 µM and 14.0 µM (Table 9). COTI-HIV-1 and COTI-HIV28236 both significantly inhibited HIV-1 integrase at all concentrations tested (P<0.03 and P<0.02 t-test, respectively). COTI-HIV28233 significantly inhibited HIV-1 integrase at 100 µM (P=0.039). Of the three compounds, COTI-HIV28233 achieved the lowest percent of the total control activity (34.82%; P=0.039) at a concentration of 100 µM.

TABLE 9

Summary of the IC50 values for COTI-HIV-1, COTI-HIV28233 and COTI-HIV28236

| Test Sample | IC50 (µM) |
| --- | --- |
| COTI-HIV-1 | 58.7 |
| COTI-HIV28233 | 23.9 |
| COTI-HIV28236 | 14.0 |

Overall, COTI-HIV-1, COTI-HIV28233 and COTI-HIV28236 appear to be effective inhibitors of HIV-1 integrase in vitro with capacity to significantly reduce HIV-1 integrase activity. COTI-HIV-1 and COTI-HIV28236 were found to significantly inhibit HIV-1 integrase activity in vitro at all concentrations tested, with the lowest concentration being 1 nM. COTI-HIV28233 was found to modestly inhibit HIV-1 integrase activity at low concentrations, but to significantly reduce activity in the range of 100 µM. The lack of attaining statistical significance at lower concentrations of COTI-HIV28233 can likely be attributed to higher standard deviations in the values obtained.

At least 50% reduction in HIV-1 integrase activity was achieved at 100 µM for both COTI-HIV28233 and COTI-HIV28236. Non-linear regression analysis of the data from COTI-HIV-1, COTI-HIV28233 and COTI-HIV28236 allowed for the calculation of their $IC_{50}$ values, which were 58.7 µM, 23.9 µM and 14.0 µM respectively. Overall, it appears as though COTI-HIV28236 was the most potent drug of the three compounds tested.

The above-described embodiments of the present invention are intended to be examples only. Alterations, modifications and variations may be effected to the particular embodiments by those of skill in the art without departing from the scope of the invention, which is defined solely by the claims appended hereto.

We claim:

1. A method for making the compound of Formula III:

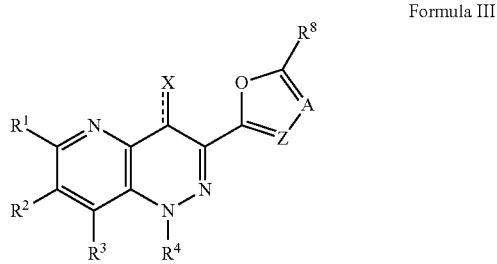

Formula III a pharmaceutically-acceptable salt, tautomer, optical isomer, E-isomer, Z-isomer, and/or combination thereof;

X is selected from Se, N—OH, NH, $NO_2$, CN, N—CN, N=O, O or S, wherein:

when X is selected from Se, N—OH, NH, N—CN, O or S, ----- is a double bond, when X is selected from $NO_2$, CN or N=O, ----- is a single bond, $R^1$, $R^2$, $R^3$, and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and Z and A are each independently selected from $CR^9$ or N, and $R^8$ and $R^9$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein the method comprises:

a) reacting a compound of Formula VII with an amine of $NH_2AHC(O)R^8$ to form an intermediate of Formula VIII:

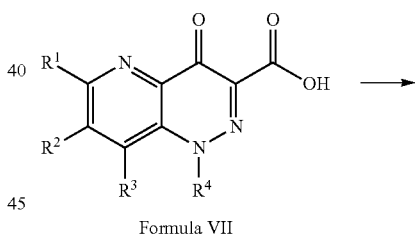

Formula VII

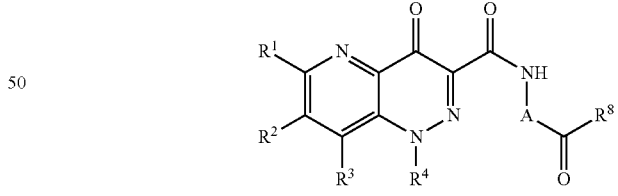

Formula VIII b) reacting the intermediate of Formula VIII with base to yield Formula III, whereby X is oxygen;

c) reacting Formula III, whereby X is oxygen, under conditions to replace the oxygen of the carbonyl group with any X group defined herein to form the compounds of Formula III.

2. The method of claim 1, wherein c) comprises reacting Formula III, whereby X is oxygen, with $NH_2OH$ to form the compound of Formula III, wherein X is N—OH.

3. A method for making the compound of Formula IV:

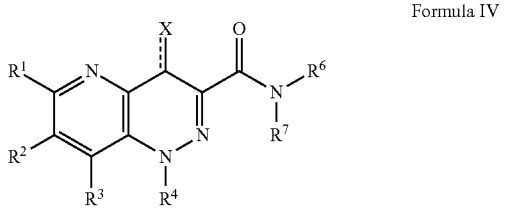

Formula IV a pharmaceutically-acceptable salt, tautomer, optical isomer, E-isomer, Z-isomer, and/or combination thereof;
X is selected from Se, N—OH, NH, $NO_2$, CN, N—CN, N=O, O or S,
wherein:
when X is Se, N—OH, NH, or N—CN, ----- is a double bond,
when X is selected from $NO_2$, CN or N=O, ----- is a single bond,
when X is O or S, ----- is a double bond,
$R^1$, $R^2$, $R^3$, and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and
wherein $R^6$ and $R^7$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group,
wherein the method comprises:
a) reacting a compound of Formula VII with an amine of $NHR^6R^7$ to form an intermediate of Formula IX:

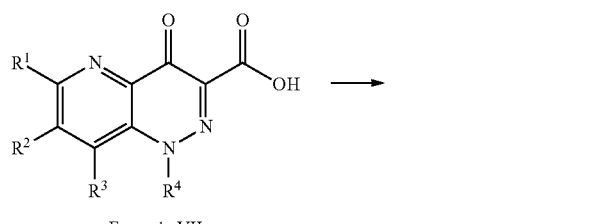

Formula VII

Formula IX b) reacting the intermediate of Formula IX under conditions to replace the oxygen of the carbonyl group in the ring with any X group defined herein to form the compound of Formula IV.

4. The method of claim 3, wherein b) comprises reacting Formula IX with $NH_2OH$ to form the compound of Formula IV, wherein X is N—OH.

5. The method of claim 1, wherein $R^1$, $R^2$, $R^3$, and $R^4$ are each independently selected from H or substituted or unsubstituted alkyl.

6. The method according to claim 1, wherein X is Se, N—OH, NH, $NO_2$, CN, N—CN, or N=O.

7. The method according to claim 1, wherein X is O or S.

8. The method according to claim 1, wherein the compound of Formula III is selected from:

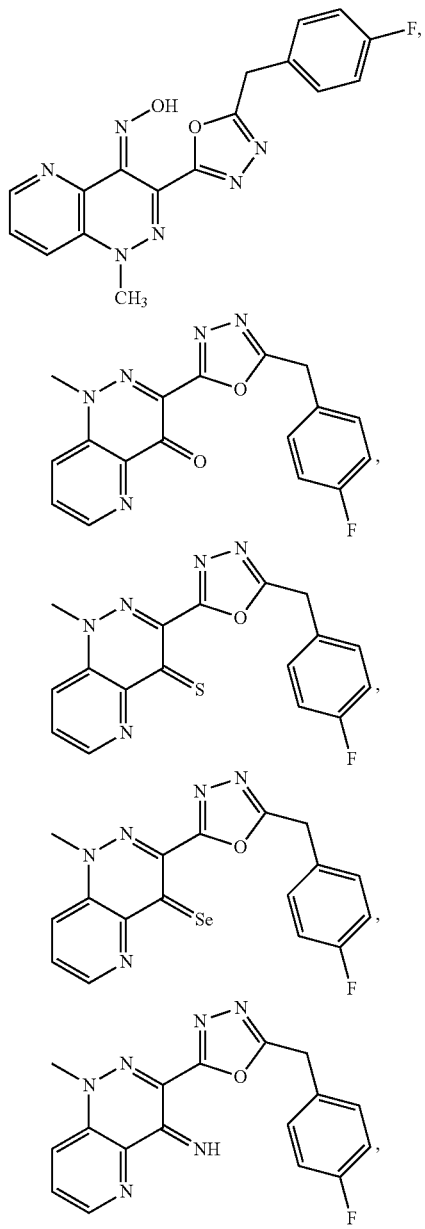

a pharmaceutically-acceptable salt, tautomer, optical isomer, E-isomer, Z-isomer, and/or combination thereof.

9. The method according to claim 1, wherein at least one of Z and A is N.

10. The method according to claim 1, wherein both Z and A are N.

11. The method according to claim 1, wherein R⁸ is a substituted or unsubstituted hydrocarbon group.

12. The method according to claim 11, wherein R⁸ is a substituted or unsubstituted alkyl group.

13. The method according to claim 1, wherein the compound of Formula III is selected from:

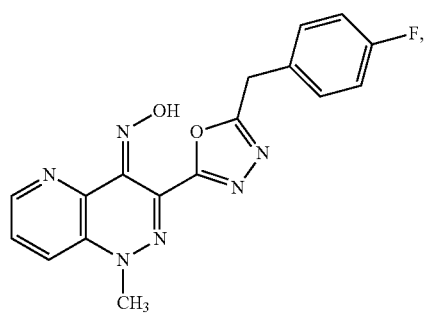 [SMILES: Cn1nc(-c2nnc(Cc3ccc(F)cc3)o2)/c(=N\O)c2ncccc21]

a pharmaceutically-acceptable salt, tautomer, optical isomer, E-isomer, Z-isomer, and/or combination thereof.

14. The method of claim 3, wherein $R^1$, $R^2$, $R^3$, and $R^4$ are each independently selected from H or substituted or unsubstituted alkyl.

15. The method according to claim 3, wherein X is Se, N—OH, NH, NO₂, CN, N—CN, or N═O.

16. The method according to claim 3, wherein $R^6$ and $R^7$ are each independently selected from H or a substituted or unsubstituted hydrocarbon group.

17. The method according to claim 16, wherein the substituted or unsubstituted hydrocarbon group is a substituted or unsubstituted alkyl group.

18. The method according to claim 17, wherein the substituted or unsubstituted alkyl group is a substituted or unsubstituted alkylaryl or a substituted or unsubstituted alkylheteroaryl.

19. The method according to claim 3, wherein X is O or S; and $R^6$ and $R^7$ are each independently selected from H or a substituted or unsubstituted alkyl group.

20. The method according to claim 3, wherein the compound of Formula IV is selected from:

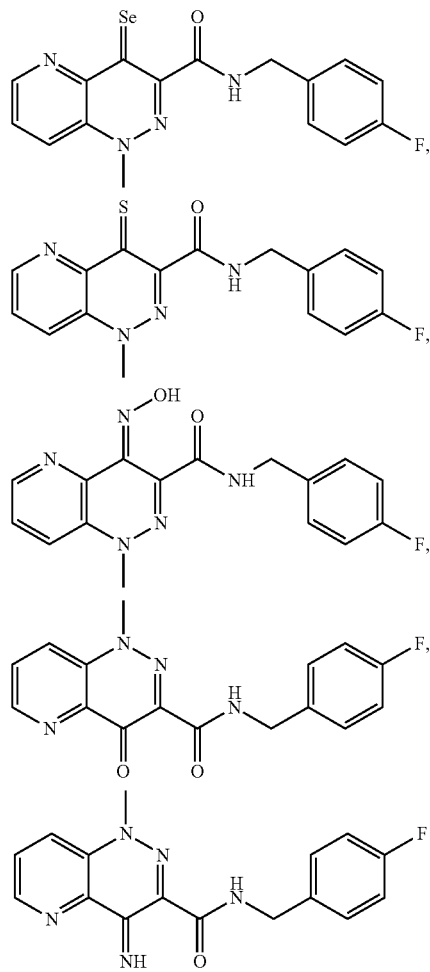

a pharmaceutically-acceptable salt, tautomer, optical isomer, E-isomer, Z-isomer, and/or combination thereof.

* * * * *